(12) United States Patent
Locke et al.

(10) Patent No.: US 11,432,967 B2
(45) Date of Patent: Sep. 6, 2022

(54) FLUID BRIDGE FOR SIMULTANEOUS APPLICATION OF NEGATIVE PRESSURE TO MULTIPLE TISSUE SITES

(71) Applicant: KCI Licensing, Inc., San Antonio, TX (US)

(72) Inventors: Christopher Brian Locke, Bournemouth (GB); Thomas Alan Edwards, Hampshire (GB)

(73) Assignee: KCI Licensing, Inc., San Antonio, TX (US)

(*) Notice: Subject to any disclaimer, the term of this patent is extended or adjusted under 35 U.S.C. 154(b) by 154 days.

(21) Appl. No.: 16/525,376

(22) Filed: Jul. 29, 2019

(65) Prior Publication Data

US 2019/0343687 A1  Nov. 14, 2019

Related U.S. Application Data

(63) Continuation-in-part of application No. 16/168,426, filed on Oct. 23, 2018.

(Continued)

(51) Int. Cl.
*A61F 13/00* (2006.01)
*A61F 13/02* (2006.01)
*A61M 1/00* (2006.01)

(52) U.S. Cl.
CPC .... *A61F 13/00068* (2013.01); *A61F 13/0216* (2013.01); *A61M 1/73* (2021.05);
(Continued)

(58) Field of Classification Search
CPC ............ A61F 13/00068; A61F 13/0216; A61F 13/0223; A61F 2013/00536;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Definition of Hollow, Merriam-Webster, https://www.merriam-webster.com/dictionary/hollow (Year: 2021).*

(Continued)

*Primary Examiner* — Philip R Wiest

(57) ABSTRACT

Disclosed embodiments may relate to devices, systems, and methods for providing negative-pressure therapy simultaneously to a plurality of tissue sites using a single negative-pressure source. For example, a fluid bridge may comprise a plurality of distal ends, each configured to interact fluidly with a tissue site. In some embodiments, each distal end may have an aperture. The bridge may also comprise a port for entry of negative pressure into the enclosed space of the bridge. In some embodiments, each distal end may comprise a one-way valve. The enclosed space of the fluid pathway between the distal ends and the port may be supported in some embodiments, to prevent collapse due to negative pressure and/or compression.

24 Claims, 25 Drawing Sheets

Related U.S. Application Data

(60) Provisional application No. 62/678,585, filed on May 31, 2018, provisional application No. 62/575,974, filed on Oct. 23, 2017.

(52) U.S. Cl.
CPC ............... *A61M 1/85* (2021.05); *A61M 1/90* (2021.05); *A61F 13/0223* (2013.01); *A61F 2013/00536* (2013.01); *A61M 1/74* (2021.05); *A61M 2205/3344* (2013.01)

(58) Field of Classification Search
CPC .............. A61M 1/0088; A61M 1/0025; A61M 1/0084; A61M 2205/3344; A61M 1/0031
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Bustad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,458,141 A | 10/1995 | Neil |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| D663,431 S | 7/2012 | Parker, III et al. |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| D686,329 S | 7/2013 | Traboulsi et al. |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| D707,830 S | 6/2014 | Klutts |
| 8,834,451 B2 | 9/2014 | Blott et al. |
| 8,926,592 B2 | 1/2015 | Blott et al. |
| 9,017,302 B2 | 4/2015 | Vitaris et al. |
| D744,659 S | 12/2015 | Bishay et al. |
| 9,198,801 B2 | 12/2015 | Weston |
| 9,211,365 B2 | 12/2015 | Weston |
| 9,289,542 B2 | 3/2016 | Blott et al. |
| 9,693,907 B2 | 7/2017 | Locke et al. |
| D806,256 S | 12/2017 | Allen et al. |
| 10,537,478 B2 * | 1/2020 | Holm ..................... B32B 27/08 |
| D885,587 S | 5/2020 | Park |
| D887,563 S | 6/2020 | Caneppele et al. |
| D890,936 S | 7/2020 | Hicken et al. |
| 10,702,419 B2 | 7/2020 | Locke et al. |
| D893,034 S | 8/2020 | Kase et al. |
| D898,925 S | 10/2020 | Kelbie et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2008/0195017 A1 | 8/2008 | Robinson et al. |

(56) References Cited

U.S. PATENT DOCUMENTS

| | | | | |
|---|---|---|---|---|
| 2010/0160877 | A1* | 6/2010 | Kagan | A61F 13/00068 604/319 |
| 2012/0308780 | A1* | 12/2012 | Rottger | A61F 13/53747 428/172 |
| 2013/0296816 | A1* | 11/2013 | Greener | A61M 1/0003 604/320 |
| 2014/0163491 | A1 | 6/2014 | Schuessler et al. | |
| 2015/0080788 | A1 | 3/2015 | Blott et al. | |
| 2015/0141941 | A1* | 5/2015 | Allen | A61F 13/00068 604/319 |
| 2015/0245950 | A1 | 9/2015 | Locke et al. | |
| 2015/0320603 | A1* | 11/2015 | Locke | A61B 17/32 604/543 |
| 2016/0120706 | A1* | 5/2016 | Collinson | A61F 13/0216 604/319 |
| 2017/0143552 | A1* | 5/2017 | Hartwell | A61F 13/0233 |
| 2017/0189236 | A1 | 7/2017 | Locke et al. | |
| 2017/0312402 | A1* | 11/2017 | McDonald | A61F 13/143 |
| 2018/0228654 | A1* | 8/2018 | Sarangapani | A61F 13/00068 |
| 2019/0117861 | A1 | 4/2019 | Locke et al. | |
| 2020/0146897 | A1 | 5/2020 | Locke et al. | |
| 2020/0353137 | A1 | 11/2020 | Long et al. | |
| 2020/0375805 | A1* | 12/2020 | Robinson | A61L 27/16 |
| 2021/0161725 | A1 | 6/2021 | Edwards et al. | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2013/175306 A2 | 11/2013 |
| WO | 2016193873 A1 | 12/2016 |

OTHER PUBLICATIONS

Definition of Stack, Cambridge English Dictionary, https://dictionary.cambridge.org/us/dictionary/english/stack (Year: 2021).*

PTFE vs. Teflon: What's the Difference? by Teflon Coat, Performance Engineered Components, https://www.industrialcoat.com/ptfe-vs-teflon-whats-difference/, Aug. 8, 2018 (Year: 2018).*

Definition of "Integral", Merriam-Webster Dictionary, https://www.merriam-webster.com/dictionary/integral, Accessed Dec. 15, 2021 (Year: 2021).*

Japanese Notice of Rejection for Corresponding Application No. 2019-006180, dated Nov. 26, 2019.

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafls; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subalmospheric Pressure Dressing Therapy to Close Lymphocutaneous Fistulas of the Groin" British Journal of Plastic Surgery (2000), 53, pp. 484-487.

George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al.; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3,1997.

Dattilo, Philip P., Jr., et al.; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al.; "Vacuum Treatment in the Surgical Management of Purulent Wounds"; Vestnik Khirurgi, Sep. 1986, pp. 18-21 and 6 page English translation thereof.

Davydov, Yu. A., et al.; "Vacuum Therapy in the Treatment of Purulent Lactation Mastitis"; Vestnik Khirurgi, May 14, 1986, pp. 66-70, and 9 page English translation thereof.

Yusupov. Yu.N., et al.; "Active Wound Drainage", Vestnki Khirurgi, vol. 138, Issue 4, 1987, and 7 page English translation thereof.

Davydov, Yu.A., et al.; "Bacteriological and Cytological Assessment of Vacuum Therapy for Purulent Wounds" Vestnik Khirugi, Oct. 1988, pp. 48-52, and 8 page English translation thereof.

Davydov, Yu.A., et al.; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al.; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, p. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by

(56) References Cited

OTHER PUBLICATIONS

V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and p. Pěska, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

U.S. Restriction Requirement for Corresponding U.S. Appl. No. 29/667,667, dated Apr. 27, 2021.

Partial International Search Report for Corresponding Application No. PCT/US2018/057109, dated Feb. 1, 2019.

U.S. Non-Final Rejection Corresponding to U.S. Appl. No. 16/168,426, dated Jun. 4, 2021.

U.S. Non-Final Rejection for Corresponding U.S. Appl. No. 29/667,667, dated Jun. 14, 2021.

"Teflon Properties", W.S. Hampshire, Inc., http://catalog.wshampshire.com/asset/psg_teflon_ptfe.pdf. Accessed 2021 (Year: 2021).

U.S. Non-Final Rejection Corresponding to U.S. Appl. No. 16/168,426, dated Oct. 15, 2021.

* cited by examiner

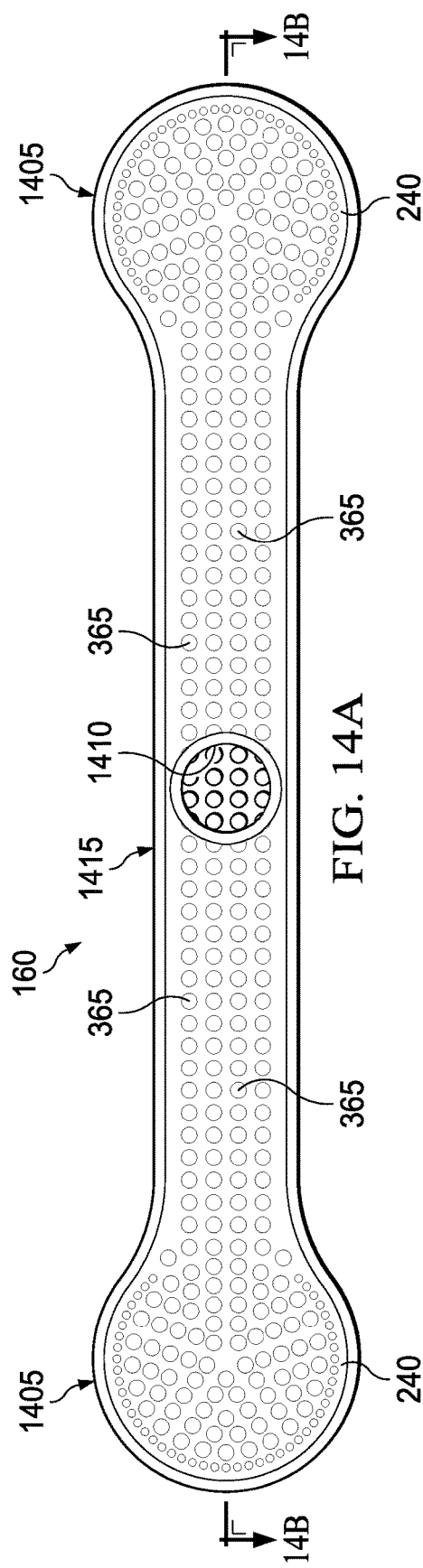
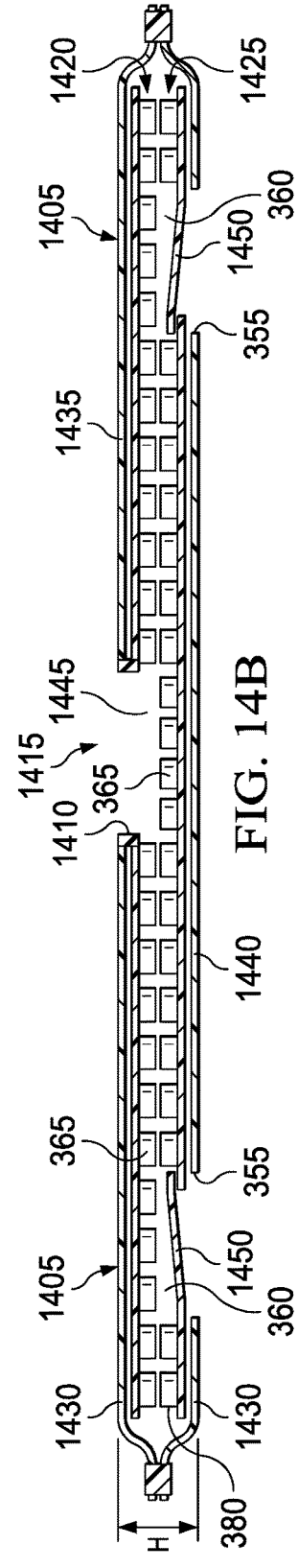
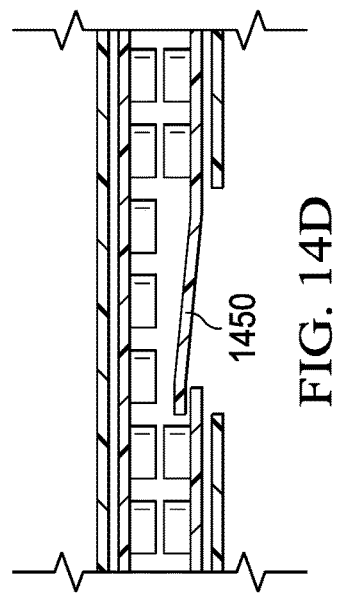
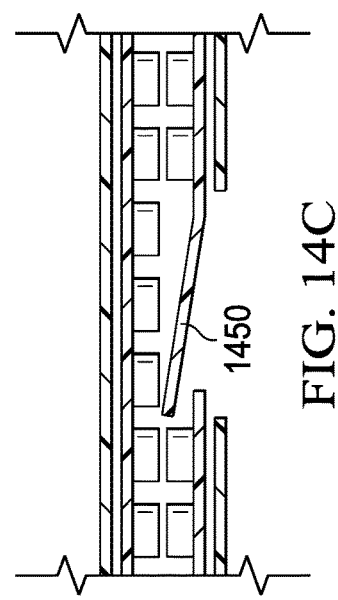

FLUID BRIDGE FOR SIMULTANEOUS APPLICATION OF NEGATIVE PRESSURE TO MULTIPLE TISSUE SITES

RELATED APPLICATIONS

This application claims the benefit, as a continuation-in-part under 35 U.S.C. § 120, of the filing of U.S. patent application Ser. No. 16/168,426, entitled "LOW PROFILE DISTRIBUTION COMPONENTS FOR WOUND THERAPY," filed Oct. 23, 2018; and claims the benefit, under 35 U.S.C. § 119(e), of the filing of U.S. Provisional Patent Application Ser. No. 62/678,585, entitled "LOW PROFILE DISTRIBUTION COMPONENTS FOR WOUND THERAPY," filed May 31, 2018; and U.S. Provisional Patent Application Ser. No. 62/575,974, entitled "LOW PROFILE DISTRIBUTION COMPONENTS FOR WOUND THERAPY," filed Oct. 23, 2017; each of which is incorporated herein by reference for all purposes.

TECHNICAL FIELD

The invention set forth in the appended claims relates generally to tissue treatment systems and more particularly, but without limitation, to low-profile distribution components for providing negative-pressure therapy and/or instillation.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound or a cavity can be washed out with a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and/or instillation therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter. Some embodiments are illustrative of an apparatus or system for delivering negative pressure simultaneously to multiple tissue sites.

For example, in some embodiments a fluid bridge may be configured to distribute negative pressure from a single source to multiple tissue sites. The fluid bridge may be configured to span multiple tissue sites, allowing exudate from the multiple tissue sites to be simultaneously drawn for negative-pressure therapy using a single negative-pressure source. Some embodiments of the fluid bridge may be specifically configured to avoid maceration of the patient's skin and/or reflux contamination between tissue sites. Some embodiments may also be configured to resist collapse when used under compression, for example if at least a portion of the fluid bridge is positioned so that the patient's body weight may lie atop it. For example, fluid bridge embodiments may comprise a thermoformed support structure within a fluid impermeable envelope to form an enclosed fluid pathway. The fluid pathway may comprise a single port configured for introduction of negative pressure into the fluid bridge and a plurality of distal ends configured to be in fluid communication with the multiple tissue sites. When negative pressure is applied to the port, fluid from the tissue sites may enter the fluid pathway through the distal ends, and then may flow from the distal ends to the port and then out of the fluid bridge.

In some embodiments, the port may be located in a central hub of the fluid bridge, with the distal ends fluidly coupled to the central hub. While some embodiments of the fluid bridge may comprise two distal ends, other embodiments may comprise three or more distal ends, each configured to allow fluid exudate from one of the tissue sites to enter the fluid pathway when under negative pressure. In some embodiments, the fluid bridge may also comprise one or more one-way valves, configured to prevent fluid from one tissue site from re-fluxing into another tissue site in a way that may cause cross-contamination between tissue sites. If a single valve is used, then the valve may be located in the fluid pathway between the port and one of the distal ends. For embodiments having a plurality of valves, some embodiments may locate a one-way valve in proximity to each distal end. For example, each one-way valve may be integral to the thermoformed support structure within the distal end. In some embodiments, each distal end may comprise an adhesive surface configured for attachment in place with respect to the tissue site, and a release liner over the adhesive which removably seals the distal ends when they are not in use.

The thermoformed support structure may be configured to allow the fluid bridge to be folded and/or compressed without significantly impacting pressure delivery or fluid removal. Some fluid bridge embodiments may use other means of support instead of a thermoformed support structure. For example, the envelope may be supported by a foam delivery manifold. Some embodiments may also include one or more regulators that can step-down the pressure within the fluid pathway to ensure that there is always a pressure gradient towards the central hub and/or port. For example, 125 mmHg negative pressure may be applied to the port in some embodiments, while the distal ends may each experience approximately −100 mmHg negative pressure due to the pressure regulators. Some embodiments may also include induced airflow, for example via a perforation in the top of each distal end, to assist in preventing blockages of the fluid pathway. In some embodiments, a bacterial filter may cover such perforations to prevent ingress of contaminants.

More generally, some embodiments may relate to delivering negative pressure to a plurality of tissue sites using a single negative-pressure source. For example, some fluid bridge apparatus embodiments may comprise: a support layer or manifold; and an envelope comprising a first surface and a second surface and encompassing the support layer, wherein the support layer supports the envelope to form an enclosed fluid pathway which comprises a plurality of distal ends in fluid communication with a central portion. In some embodiments, each distal end may comprise an aperture in the envelope, and the central portion may comprise a port in the envelope. The port may be located on the first surface of the envelope in some embodiments, and the apertures may be located on the second surface. Some fluid bridge embodiments may further comprise at least one one-way valve located between the port and one of the apertures and configured to allow fluid flow from the aperture toward the port. For example, each of the distal ends may comprise a one-way valve in proximity to the aperture and configured to allow fluid flow from the aperture towards the port. The one-way valves may be flap valves in some embodiments.

In some embodiments, the support layer may be configured within the envelope to maintain an open fluid pathway when under compression and/or to be foldable while still maintaining open fluid pathway. The fluid pathway may also be low-profile. In some embodiments, the central portion may be located in the fluid pathway between at least two of the distal ends. For example, the central portion may be located in the fluid pathway approximately halfway between two distal ends. In some embodiments, the support layer may comprises a thermoformed support structure. For example, the support layer may comprise a plurality of supports configured to support the envelope and/or to maintain an open fluid pathway when under compression. In some embodiments, the plurality of supports may be substantially co-extensive with the fluid pathway. In some embodiments, the envelope may further comprise a first layer and a second layer, the first layer and the second layer may be coupled together (e.g. about the perimeter) to form the enclosed fluid pathway between the first layer and the second layer, and the plurality of supports may be located between the first layer and the second layer.

In some embodiments, the support layer may comprise a spacer layer, with the plurality of supports extending from an inner surface of the spacer layer. In some embodiments, the plurality of supports may comprise a first plurality of supports and a second plurality of supports, and the first plurality of supports may be in stacked relationship with the second plurality of supports. The support layer of some embodiments may comprise a first spacer layer and a second spacer layer, and the plurality of supports may comprises a first plurality of supports extending inward from the first spacer layer and a second plurality of supports extending inward from the second spacer layer. In some embodiments, the plurality of supports may be arranged in rows that extend longitudinally. The fluid pathway of some fluid bridge embodiments may further comprise a recessed space in each distal end in fluid communication with the aperture. For example, each recessed space may be formed by an opening in the second spacer layer. In some embodiments, the fluid pathway may further comprises a port recessed space in fluid communication with the port. For example, the port recessed space may be formed by an opening in the first spacer layer. In some embodiments of the fluid bridge, the plurality of one-way valves may be integral to the second spacer layer. The support layer or manifold of some embodiments may not comprise a plurality of supports (such as thermoformed spacer layers), but instead may comprise a foam delivery manifold.

The enclosed fluid pathway of some embodiments may comprise a primary fluid pathway having two of the plurality of distal ends. Some embodiments of the enclosed fluid pathway may further comprise one or more branch fluid pathways, each having one of the plurality of distal ends and a proximal end in fluid communication with the primary fluid pathway. Some fluid bridge embodiments may further comprise a plurality of release liners, for example with one release liner removably covering each aperture. In some embodiments, one release liner may removably cover the port. Each of the release liners may removably seal the aperture and/or port. In some embodiments, each distal end may further comprise adhesive located in proximity to the aperture, and the release liners may removably cover the adhesives.

Some embodiments of the fluid bridge may further comprise a plurality of regulators configured to step-down pressure, with a regulator positioned between each distal end and the central portion. The envelope of some embodiments may comprise a perforation forming a calibrated flow of less than about 5 cc/min, for example located in proximity to each of the distal ends. The envelope may further comprise a bacterial filter over each calibrated flow, in some embodiments.

Some embodiments may relate to an apparatus for delivering negative pressure to a plurality of tissue sites, comprising: a support layer or manifold; and an envelope comprising a first surface and a second surface and encompassing the support layer, wherein the support layer supports the envelope to form an enclosed fluid pathway which comprises one or more distal ends in fluid communication with a central portion. The fluid pathway may comprise a port in the envelope. In some embodiments, the one or more distal end may each comprise an aperture in the envelope. In some embodiments, the support layer may further comprise a first spacer layer with a first plurality of supports extending inward and a second spacer layer with a second plurality of supports extending inward. The first plurality of supports may be in stacked relationship with the second plurality of supports, to jointly support the envelope. In some embodiments, the fluid pathway may comprise only one distal end, and the port may be located in a proximal end of the fluid pathway. In other embodiments, the fluid pathway may comprise at least two distal ends with apertures, and the port may be located in the central portion of the fluid pathway.

Some embodiments may relate to an apparatus for delivering negative pressure to a plurality of tissue sites, comprising: a support layer or manifold; and an envelope comprising a first surface and a second surface and encompassing the support layer, wherein the support layer supports the envelope to form an enclosed fluid pathway which comprises a plurality of distal ends. In some embodiments, at least two of the plurality of distal ends may each comprise an aperture in the envelope, and the fluid pathway may comprise a port in the envelope. In some embodiments, the plurality of distal ends may be in fluid communication with a central portion of the enclosed fluid pathway, and the port may be located on the central portion of the fluid pathway. The port may be located on the first surface in some embodiments, and the apertures may be located on the second surface. Some embodiments of the fluid bridge may further comprise at least one one-way valve located between the port and one of the apertures and configured to allow fluid flow from the aperture toward the port. In some embodiments, each of the distal ends may comprise an aperture, and each of the distal ends may also comprise a one-way valve in proximity to the aperture which is configured to allow fluid flow from the aperture towards the port. In alternate embodiments, the plurality of distal ends may comprises at least three distal ends, the port may be located in one of the distal ends, and one of the apertures may be located in each of the distal ends without the port. In some embodiments, the support layer may comprise a thermoformed support structure, while in other embodiments the support layer may comprise a foam delivery manifold.

Some embodiments may relate to a system for simultaneously treating a plurality of tissue sites with a single negative-pressure source, and may comprise a fluid bridge, and a negative-pressure source in fluid communication with the fluid bridge at a port. The fluid bridge may be similar to those described above, for example having two or more distal ends. The distal ends of the fluid bridge may be in fluid communication with two or more tissue sites in some embodiments. Some fluid bridge embodiments may be configured to maintain effective negative-pressure therapy when the fluid bridge is folded and/or to maintain effective negative-pressure therapy when at least a portion of the fluid bridge is under compression. Some system embodiments may further comprise a tissue interface and a cover for each tissue site. For example, each tissue interface may be configured to be in fluid communication with one of the apertures through one of the covers, and/or each cover may be configured to span and seal one of the tissue sites.

Method embodiments may also be disclosed herein, and may relate to simultaneously applying negative pressure to a plurality of tissue sites. For example, method embodiments may comprise the steps of: providing a fluid bridge; applying two or more distal ends of the fluid bridge to the plurality of tissue sites; and applying negative pressure to a port of the fluid bridge. Providing the fluid bridge may comprise providing one of the bridge embodiments described herein. Some method embodiments may further comprise adjusting the fluid bridge to position the distal ends with respect to the plurality of tissue sites. Some fluid bridge embodiments may comprise a primary fluid pathway and one or more branch fluid pathways, and adjusting the fluid bridge may comprise adjusting the length of one or more branch fluid pathways. For example, adjusting the length of the one or more branch fluid pathways may comprise folding the one or more branch fluid pathways. In some embodiments, adjusting the fluid bridge may comprise adjusting the lateral position of one or more of the distal ends by folding the one or more branch fluid pathways at an angle. In some embodiments, adjusting the fluid bridge may comprise adjusting the length of the primary fluid pathway. For example, adjusting the length of the primary fluid pathway may comprise folding the primary fluid pathway. In some embodiments, adjusting the fluid bridge may comprise adjusting the lateral position of one or more of the distal ends by folding the primary fluid pathway at an angle.

Some method embodiments may relate to forming a fluid bridge for simultaneous application of negative pressure to a plurality of tissue sites using a single negative-pressure source, the and may comprise the steps of: providing a support layer or manifold; encasing the support layer within an envelope, wherein the support layer supports the envelope to form an enclosed fluid pathway having a plurality of distal ends in fluid communication with a central portion; forming a port in a first surface of the envelope in proximity to the central portion; and forming a plurality of apertures in a second surface of the envelope in proximity to the distal ends. In some embodiments, each distal end may comprise one of the apertures. In some method embodiments, providing a support layer may comprise forming the support layer to have a primary portion (which may form the primary fluid pathway when enclosed in the envelope) and one or more branch portions (which may form the branch fluid pathways when enclosed in the envelope). In some method embodiments, providing the support layer may comprise: providing a first spacer layer with a first plurality of supports and a second spacer layer with a second plurality of supports; forming an opening in the first spacer layer; and forming a plurality of openings in the second spacer layer. The step of providing the support layer in some embodiments may further comprise stacking the first spacer layer and the second spacer layer. In some embodiments, the opening in the first spacer layer may be aligned with the port, and the plurality of openings in the second layer may each be aligned with one of the plurality of apertures. The step of providing a second spacer layer may comprise forming or applying a one-way valve for each opening in the second spacer layer, in some embodiments. For example, each one-way valve may be integrally formed in the second spacer layer, and may be configured to allow fluid flow into the fluid pathway but to prevent fluid flow out of the fluid pathway through the openings in the second spacer layer.

Objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

FIG. 14A is a plan view of another example of a bridge that may be associated with some example embodiments of the therapy system of FIG. 1, particularly embodiments allowing a single negative-pressure source to provide negative-pressure therapy to a plurality of tissue sites;

FIG. 14B is a longitudinal cross-section view of the bridge of FIG. 14A;

FIG. 14C is a schematic view of an exemplary valve from FIG. 14B in open position;

FIG. 14D is a schematic view of the exemplary valve of FIG. 14C in closed position;

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
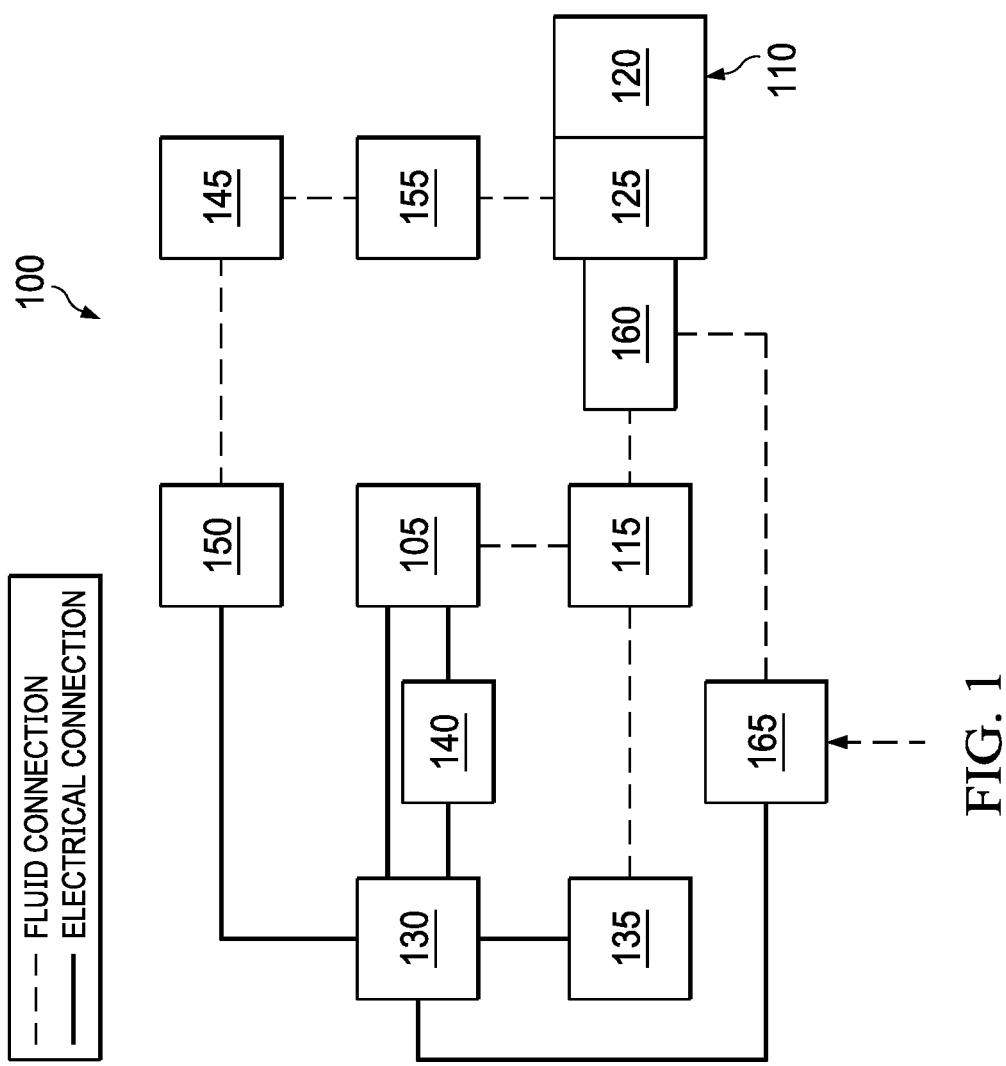
FIG. 1 is a functional block diagram of an example embodiment of a therapy system that can provide negative-pressure treatment and instillation treatment in accordance with this specification.

FIG. 1 is a simplified functional block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 105, and one or more distribution components. A distribution component is preferably detachable and may be disposable, reusable, or recyclable. A dressing, such as a dressing 110, and a fluid container, such as a container 115, are examples of distribution components that may be associated with some examples of the therapy system 100. As illustrated in the example of FIG. 1, the dressing 110 may comprise or consist essentially of a tissue interface 120, a cover 125, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. A tube, for example, is generally an elongated, flexible structure with a cylindrical lumen, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 110. For example, such a dressing interface may be a SENSAT.R.A.C.™ Pad, available from Kinetic Concepts, Inc. of San Antonio, Tex.

The therapy system 100 may also include a regulator or controller, such as a controller 130. Additionally, the therapy system 100 may include sensors to measure operating parameters and provide feedback signals to the controller 130 indicative of the operating parameters. As illustrated in FIG. 1, for example, the therapy system 100 may include a first sensor 135 and a second sensor 140 coupled to the controller 130.

The therapy system 100 may also include a source of instillation solution. For example, a solution source 145 may be fluidly coupled to the dressing 110, as illustrated in the example embodiment of FIG. 1. The solution source 145 may be fluidly coupled to a positive-pressure source, such as a positive-pressure source 150, a negative-pressure source, such as the negative-pressure source 105, or both in some embodiments. A regulator, such as an instillation regulator 155, may also be fluidly coupled to the solution source 145 and the dressing 110 to ensure proper dosage of instillation solution (e.g. saline) to a tissue site. For example, the instillation regulator 155 may comprise a piston that can be pneumatically actuated by the negative-pressure source 105 to draw instillation solution from the solution source during a negative-pressure interval and to instill the solution to a dressing during a venting interval. Additionally or alternatively, the controller 130 may be coupled to the negative-pressure source 105, the positive-pressure source 150, or both, to control dosage of instillation solution to a tissue site. In some embodiments, the instillation regulator 155 may also be fluidly coupled to the negative-pressure source 105 through the dressing 110, as illustrated in the example of FIG. 1.

In some examples, a bridge 160 may fluidly couple the dressing 110 to the negative-pressure source 105, as illustrated in FIG. 1. The therapy system 100 may also comprise a flow regulator, such as a regulator 165, fluidly coupled to a source of ambient air to provide a controlled or managed flow of ambient air. In some embodiments, the regulator 165 may be fluidly coupled to the tissue interface 120 through the bridge 160. In some embodiments, the regulator 165 may be positioned proximate to the container 115 and/or proximate a source of ambient air, where the regulator 165 is less likely to be blocked during usage.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 130, the solution source 145, and other components into a therapy unit.

In general, components of the therapy system 100 may be coupled directly or indirectly. For example, the negative-pressure source 105 may be directly coupled to the container 115 and may be indirectly coupled to the dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 130 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 105, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 105 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 130, may be a microprocessor or computer programmed to operate one or more components of the therapy system 100, such as the negative-pressure source 105. In some embodiments, for example, the controller 130 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 120, for example. The controller 130 is also preferably configured to receive one or more input signals, such as a feedback signal, and programmed to modify one or more operating parameters based on the input signals.

Sensors, such as the first sensor 135 and the second sensor 140, are generally known in the art as any apparatus operable to detect or measure a physical phenomenon or property, and generally provide a signal indicative of the phenomenon or property that is detected or measured. For example, the first sensor 135 and the second sensor 140 may be configured to measure one or more operating parameters of the therapy system 100. In some embodiments, the first sensor 135 may be a transducer configured to measure pressure in a pneumatic pathway and convert the measurement to a signal indicative of the pressure measured. In some embodiments, for example, the first sensor 135 may be a piezo-resistive strain gauge. The second sensor 140 may optionally measure operating parameters of the negative-pressure source 105, such as a voltage or current, in some embodiments. Preferably, the signals from the first sensor 135 and the second sensor 140 are suitable as an input signal to the controller 130, but some signal conditioning may be appropriate in some embodiments. For example, the signal may need to be filtered or amplified before it can be processed by the controller 130. Typically, the signal is an electrical signal, but may be represented in other forms, such as an optical signal.

The tissue interface 120 can be generally adapted to partially or fully contact a tissue site. The tissue interface 120 may take many forms, and may have many sizes, shapes, or thicknesses, depending on a variety of factors, such as the type of treatment being implemented or the nature and size of a tissue site. For example, the size and shape of the tissue interface 120 may be adapted to the contours of deep and irregular shaped tissue sites. Any or all of the surfaces of the tissue interface 120 may have an uneven, coarse, or jagged profile.

In some embodiments, the tissue interface 120 may comprise or consist essentially of a manifold. A manifold in this context may comprise or consist essentially of a means for collecting or distributing fluid across the tissue interface 120 under pressure. For example, a manifold may be adapted to receive negative pressure from a source and distribute negative pressure through multiple apertures across the tissue interface 120, which may have the effect of collecting fluid from across a tissue site and drawing the fluid toward the source. In some embodiments, the fluid path may be reversed or a secondary fluid path may be provided to facilitate delivering fluid, such as fluid from a source of instillation solution, across a tissue site.

In some illustrative embodiments, a manifold may comprise a plurality of pathways, which can be interconnected to improve distribution or collection of fluids. In some illustrative embodiments, a manifold may comprise or consist essentially of a porous material having interconnected fluid pathways. Examples of suitable porous material that can be adapted to form interconnected fluid pathways (e.g., channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

In some embodiments, the tissue interface 120 may comprise or consist essentially of reticulated foam having pore sizes and free volume that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The tensile strength of the tissue interface 120 may also vary according to needs of a prescribed therapy. For example, the tensile strength of foam may be increased for instillation of topical treatment solutions. The 25% compression load deflection of the tissue interface 120 may be at least 0.35 pounds per square inch, and the 65% compression load deflection may be at least 0.43 pounds per square inch. In some embodiments, the tensile strength of the tissue interface 120 may be at least 10 pounds per square inch. The tissue interface 120 may have a tear strength of at least 2.5 pounds per inch. In some embodiments, the tissue interface may be foam comprised of polyols, such as polyester or polyether, isocyanate, such as toluene diisocyanate, and polymerization modifiers, such as amines and tin compounds. In some examples, the tissue interface 120 may be reticulated polyurethane foam such as found in GRANUFOAM™ dressing or V.A.C. VERAFLO™ dressing, both available from Kinetic Concepts, Inc. of San Antonio, Tex.

The thickness of the tissue interface 120 may also vary according to needs of a prescribed therapy. For example, the thickness of the tissue interface may be decreased to reduce tension on peripheral tissue. The thickness of the tissue interface 120 can also affect the conformability of the tissue interface 120. In some embodiments, a thickness in a range of about 5 millimeters to 10 millimeters may be suitable.

The tissue interface 120 may be either hydrophobic or hydrophilic. In an example in which the tissue interface 120 may be hydrophilic, the tissue interface 120 may also wick fluid away from a tissue site, while continuing to distribute negative pressure to the tissue site. The wicking properties of the tissue interface 120 may draw fluid away from a tissue site by capillary flow or other wicking mechanisms. An example of a hydrophilic material that may be suitable is a polyvinyl alcohol, open-cell foam such as V.A.C. WHITEFOAM™ dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

In some embodiments, the tissue interface 120 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The tissue interface 120 may further serve as a scaffold for new cell-growth, or a scaffold material may be used in conjunction with the tissue interface 120 to promote cell growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 125 may provide a bacterial barrier and protection from physical trauma. The cover 125 may also be constructed from a material that can reduce evaporative losses and provide a fluid seal between two components or two environments, such as between a therapeutic environment and a local external environment. The cover 125 may comprise or consist of, for example, an elastomeric film or membrane that can provide a seal adequate to maintain a negative pressure at a tissue site for a given negative-pressure source. The cover 125 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 125 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 125 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis Minn.; polyurethane (PU) drape, commercially available from Avery Dennison Corporation, Pasadena, Calif.; polyether block polyamide copolymer (PEBAX), for example, from Arkema S.A., Colombes, France; and Inspire 2301 and Inpsire 2327 polyurethane films, commercially available from Expopack Advanced Coatings, Wrexham, United Kingdom. In some embodiments, the cover 125 may comprise INSPIRE 2301 having an MVTR (upright cup technique) of 2600 g/m$^2$/24 hours and a thickness of about 30 microns.

An attachment device may be used to attach the cover 125 to an attachment surface, such as undamaged epidermis, a gasket, or another cover. The attachment device may take many forms. For example, an attachment device may be a medically-acceptable, pressure-sensitive adhesive configured to bond the cover 125 to epidermis around a tissue site. In some embodiments, for example, some or all of the cover 125 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The solution source 145 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

In operation, the tissue interface 120 may be placed within, over, on, or otherwise proximate to a tissue site. If the tissue site is a wound, for example, the tissue interface 120 may partially or completely fill the wound, or it may be placed over the wound. The cover 125 may be placed over the tissue interface 120 and sealed to an attachment surface near a tissue site. For example, the cover 125 may be sealed to undamaged epidermis peripheral to a tissue site. Thus, the dressing 110 can provide a sealed therapeutic environment proximate to a tissue site, substantially isolated from the external environment, and the negative-pressure source 105 can reduce pressure in the sealed therapeutic environment. In some embodiments, the regulator 165 may control the flow of ambient air to purge fluids and exudates from the sealed therapeutic environment.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudate and other fluid flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and this descriptive convention should not be construed as a limiting convention.

Negative pressure applied across the tissue site through the tissue interface 120 in the sealed therapeutic environment can induce macro-strain and micro-strain in the tissue site. Negative pressure can also remove exudate and other fluid from a tissue site, which can be collected in container 115.

In some embodiments, the controller 130 may receive and process data from one or more sensors, such as the first sensor 135. The controller 130 may also control the operation of one or more components of the therapy system 100 to manage the pressure delivered to the tissue interface 120. In some embodiments, controller 130 may include an input for receiving a desired target pressure and may be programmed for processing data relating to the setting and inputting of the target pressure to be applied to the tissue interface 120. In some example embodiments, the target pressure may be a fixed pressure value set by an operator as the target negative pressure desired for therapy at a tissue site and then provided as input to the controller 130. The target pressure may vary from tissue site to tissue site based on the type of tissue forming a tissue site, the type of injury or wound (if any), the medical condition of the patient, and the preference of the attending physician. After selecting a desired target pressure, the controller 130 can operate the negative-pressure source 105 in one or more control modes based on the target pressure and may receive feedback from one or more sensors to maintain the target pressure at the tissue interface 120.

In some embodiments, the controller 130 may have a continuous pressure mode, in which the negative-pressure source 105 is operated to provide a constant target negative pressure for the duration of treatment or until manually deactivated. Additionally or alternatively, the controller may have an intermittent pressure mode. For example, the controller 130 can operate the negative-pressure source 105 to cycle between a target pressure and atmospheric pressure. In some examples, the target pressure may be set at a value of 135 mmHg for a specified period of time (e.g., 5 min), followed by a specified period of time (e.g., 2 min) of deactivation. The cycle can be repeated by activating the negative-pressure source 105, which can form a square wave pattern between the target pressure and atmospheric pressure.

In some example embodiments, the increase in negative pressure from ambient pressure to the target pressure may not be instantaneous. For example, the negative-pressure source 105 and the dressing 110 may have an initial rise time, which can vary depending on the type of dressing and therapy equipment being used. For example, the initial rise time for one therapy system may be in a range of about 20-30 mmHg/second and in a range of about 5-10 mmHg/second for another therapy system. If the therapy system 100 is operating in an intermittent mode, the repeating rise time may be a value substantially equal to the initial rise time.

In other examples, a target pressure can vary with time in a dynamic pressure mode. For example, the target pressure may vary in the form of a triangular waveform, varying between a negative pressure of 50 and 135 mmHg with a rise time set at a rate of +25 mmHg/min. and a descent time set at −25 mmHg/min. In other embodiments of the therapy system 100, the triangular waveform may vary between negative pressure of 25 and 135 mmHg with a rise time set at a rate of +30 mmHg/min and a descent time set at −30 mmHg/min.

In some embodiments, the controller 130 may control or determine a variable target pressure in a dynamic pressure mode, and the variable target pressure may vary between a maximum and minimum pressure value that may be set as an input prescribed by an operator as the range of desired negative pressure. The variable target pressure may also be processed and controlled by the controller 130, which can vary the target pressure according to a predetermined waveform, such as a triangular waveform, a sine waveform, or a saw-tooth waveform. In some embodiments, the waveform may be set by an operator as the predetermined or time-varying negative pressure desired for therapy.

Figure 2:
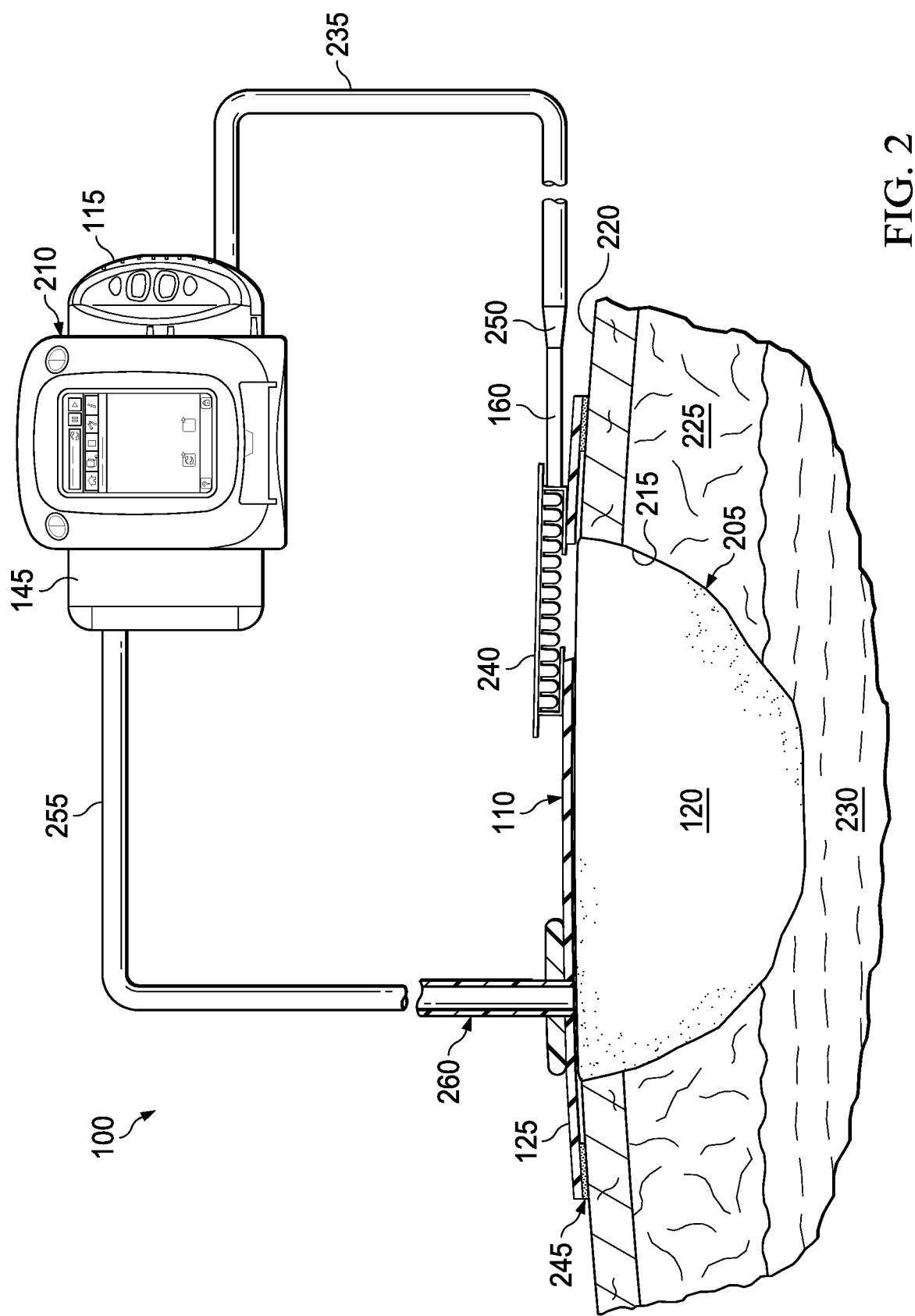
FIG. 2 is a schematic diagram of an example embodiment of the therapy system of FIG. 1 configured to apply negative pressure and treatment solutions to a tissue site.

FIG. 2 is a schematic diagram of an example embodiment of the therapy system 100 configured to apply negative pressure and treatment solutions to a tissue site 205. Some components of the therapy system 100 may be housed within or used in conjunction with other components, such as processing units, alarm indicators, memory, databases, software, display devices, or user interfaces that further facilitate therapy. For example, in some embodiments, the negative-pressure source 105 may be combined with the controller 130 and other components into a therapy unit, such as a therapy unit 210 illustrated in FIG. 2. The therapy unit 210 may be, for example, a V.A.C.ULTA™ Therapy Unit available from Kinetic Concepts, Inc. of San Antonio, Tex.

In the example of FIG. 2, the tissue site 205 is at least partially defined by a wound edge 215, which extends through an epidermal layer 220 and a dermal layer 225 and reaches into a hypodermis, or subcutaneous tissue 230. The therapy system 100 may be used to treat a wound of any depth, as well as many different types of wounds, including open wounds, incisions, or other tissue sites. Treatment of the tissue site 205 may include removal of fluids originating from the tissue site 205, such as exudates or ascites, or fluids instilled into the dressing to cleanse or treat the tissue site 205, such as antimicrobial solutions.

In the example of FIG. 2, a conduit 235 fluidly couples the container 115 to another fluid conductor, such as the bridge 160, which provides a fluid pathway between the conduit 235 and the tissue interface 120. The bridge 160 in the example of FIG. 2 is a substantially flat and flexible fluid conductor, but can also be compressed without occluding or blocking the fluid pathway between the conduit 235 and the tissue interface 120. In some embodiments, the bridge 160 may comprise or be coupled to an applicator 240 adapted to be positioned in fluid communication with the tissue interface 120 through an aperture in the cover 125. The cover 125 may be sealed to the epidermal layer 220 with an attachment device, such as an adhesive layer 245.

In some embodiments, the applicator 240 may be integral to the bridge 160. In other embodiments, the applicator 240 and the bridge 160 may be separate components that are coupled together to form a single device. In yet other embodiments, the applicator 240 and the bridge 160 may be separate components that may be used independently of each other in the therapy system 100.

The bridge 160 may have a substantially flat profile, and an adapter 250 may be configured to fluidly couple the bridge 160 to a tube or other round fluid conductor, such as the conduit 235 illustrated in the example of FIG. 2. In some embodiments, the adapter 250 may have one or more sealing valves, which can isolate the conduit 235 if separated from the bridge 160.

The example of FIG. 2 also illustrates a configuration of the therapy system 100 in which the solution source 145 is fluidly coupled to the tissue interface 120 through a conduit 255 and a dressing interface 260.

Figure 3A:
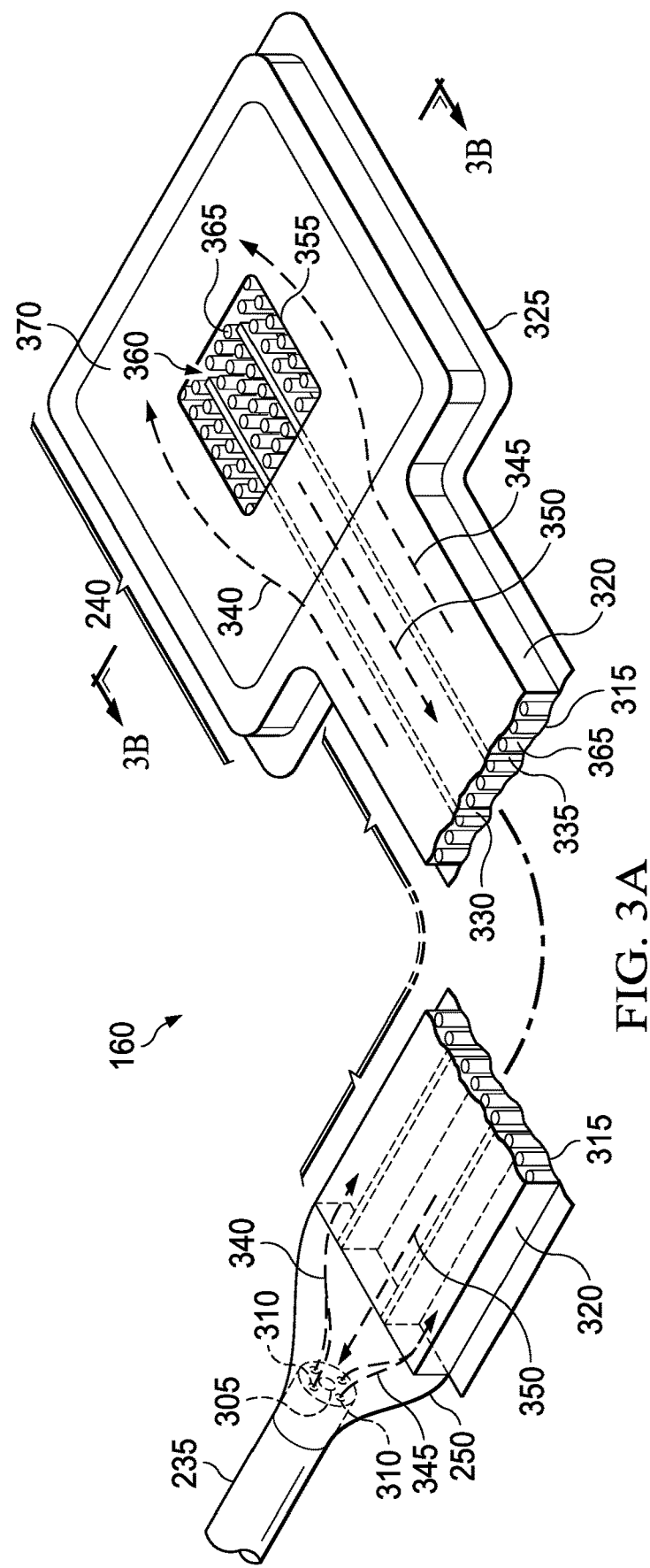
FIG. 3A is a segmented isometric bottom view of an example of a bridge that may be associated with some embodiments of the therapy system of FIG. 1.

FIG. 3A is a segmented perspective bottom view of an example of the bridge 160, illustrating additional details that may be associated with some embodiments. The bridge 160 of FIG. 3A generally has a low profile structure. FIG. 3A further illustrates features that may be associated with some embodiments of the applicator 240 of FIG. 2. The applicator 240 may be bulbous or any shape suitable for facilitating a connection to the dressing 110. The bridge 160 in the example of FIG. 3A is generally long and narrow. An adapter, such as the adapter 250, may fluidly couple the bridge 160 to a fluid conductor, such as the conduit 235. In some examples, the conduit 235 may be a multi-lumen tube in which a central lumen 305 is configured to couple the bridge 160 to a negative-pressure source, and one or more peripheral lumens 310 are configured to couple the bridge 160 to a sensor, such as the first sensor 135.

In some embodiments, the bridge 160 may comprise a liquid barrier, for example an envelope, which may be formed from two layers. In FIG. 3A, for example, a periphery of a first layer 315 may be coupled to a second layer 320 to form a fluid path between two ends of the bridge 160, including the applicator 240. The first layer 315 and the second layer 320 may both be formed from or include a polymeric film of liquid-impermeable material. In some examples, the first layer 315, the second layer 320, or both may be formed from the same material as the cover 125. The first layer 315 and the second layer 320 may be coupled around the periphery of the bridge 160 to form the sealed space by welding (RF or ultrasonic), heat sealing, or adhesive bonding, such as acrylics or cured adhesives. For example, the first layer 315 and the second layer 320 may be welded together around the periphery of the bridge 160 and may form a flange 325 around the periphery of the bridge 160 as a result of the weld.

The bridge 160 of FIG. 3A may further comprise at least one barrier or wall, such as a first wall 330, between the first layer 315 and the second layer 320. In some embodiments, the first wall 330 may extend from the end of the bridge 160 adjacent to the adapter 250 into the applicator 240 to form at least two sealed spaces or fluid pathways between the first layer 315 and the second layer 320 within the bridge 160. In some examples, the bridge 160 may further comprise a second barrier, such as a second wall 335, between the first layer 315 and the second layer 320. In some embodiments, the second wall 335 also may extend from the end of the bridge 160 adjacent to the adapter 250 into the applicator 240. In some example embodiments, the first wall 330 and the second wall 335 may comprise a polymeric film coupled to the first layer 315 and the second layer 320. In some other example embodiments, the first wall 330 and the second wall 335 may comprise a weld (RF or ultrasonic), a heat seal, an adhesive bond, or a combination of any of the foregoing. In some embodiments, the first wall 330 and the second wall 335 may form distinct fluid pathways within the sealed space between the first layer 315 and the second layer 320. In FIG. 3A, for example, the first wall 330 and the second wall 335 define in part a first pathway 340, a second pathway 345, and a third pathway 350. Each of the first pathway 340, the second pathway 345, and the third pathway 350 generally has a first end, a second end, and a longitudinal axis. In some embodiments, one or more of the fluid pathways may be fluidly coupled or configured to be fluidly coupled to the peripheral lumens 310, which can provide a pressure feedback path to a sensor, such as the first sensor 135. The third pathway 350 may be fluidly coupled to or configured to be fluidly coupled to the central lumen 305.

In some example embodiments, the first pathway 340, the second pathway 345, and the third pathway 350 may be fluidly coupled to the conduit 235 through the adapter 250. For example, the third pathway 350 may be fluidly coupled to the conduit 235 so that the third pathway 350 can deliver negative pressure to the tissue interface 120. Each of the first pathway 340 and the second pathway 345 may be fluidly coupled to a separate one of the peripheral lumens 310. In other embodiments, the first pathway 340 and the second pathway 345 both may be fluidly coupled to a common space within the adapter 250, which can be fluidly coupled to one or more of the peripheral lumens 310. In some example embodiments, the first pathway 340, the second pathway 345, and the third pathway 350 may terminate within the applicator 240. In some embodiments, the first pathway 340, the second pathway 345, and the third pathway 350 may be in fluid communication with each other within the applicator 240 for delivering and sensing negative pressure associated with the tissue interface 120.

The bridge 160 may comprise an opening or aperture, such as an aperture 355, adapted to fluidly couple the sealed space of the bridge 160 to the tissue interface 120. In FIG. 3A, for example, the aperture 355 is disposed in the applicator 240. A recessed space 360 within the bridge 160 can be adapted to be in fluid communication with the tissue interface 120 through the aperture 355 in use. In the example of FIG. 3A, the portions of first layer 315 and the second layer 320 at least partially define the recessed space 360 within the sealed space of the applicator 240. In some example embodiments, the first wall 330 and the second wall 335 may extend only partially into the recessed space 360 so that the ends of the first wall 330 and the second wall 335 are exposed by the aperture 355 as shown in the example of FIG. 3A. In some embodiments, the first pathway 340 and the second pathway 345 may be in fluid communication with the recessed space 360. The third pathway 350 may also be in fluid communication with the recessed space 360 and can be adapted to deliver negative pressure to the tissue interface 120 through the recessed space 360. In some example embodiments (not shown), the first wall 330 and the second wall 335 may extend beyond the aperture 355 so that less of the first pathway 340 and the second pathway 345 are exposed to negative pressure delivered to the tissue interface 120 to prevent or reduce occlusions and/or blockages.

The bridge 160 may further comprise a means for supporting fluid paths under pressure, for example a support layer. In some embodiments, the support layer may comprise a plurality of support features, such as a flexible projections, standoffs, nodes, cells, porous textile, porous foam, or some combination of features disposed in a fluid path. For example, the bridge 160 of FIG. 3A comprises a plurality of supports 365. Adjacent to the aperture 355, the supports 365 may be adapted to come in direct contact with the tissue interface 120 in some examples. Support features such as the supports 365 can provide a cushion to prevent the sealed spaces of the bridge 160 from collapsing as a result of external forces. In some example embodiments, the supports 365 may come in contact with the second layer 320, and in some other example embodiments, the top portion of the supports 365 may be coupled to the second layer 320. In some example embodiments, the supports 365 may be disposed only in the applicator 240, and other support features may be disposed in the bridge 160 between the applicator 240 and the conduit 235.

The bridge 160 of FIG. 3A may also comprise an affixation surface 370 surrounding the aperture 355, which can be coupled to the dressing 110 or directly to a tissue site in some examples. In some embodiments, a top drape (not shown) may be utilized to cover the applicator 240 for additional protection and support over the applicator 240 if applied to a tissue site. In some embodiments, a top drape may also be utilized to cover any adhesive that might be exposed. In some embodiments, a top drape may be similar to the cover 125. For example, a top drape may comprise or consist essentially of a polymer, such as a polyurethane film.

Figure 3B:
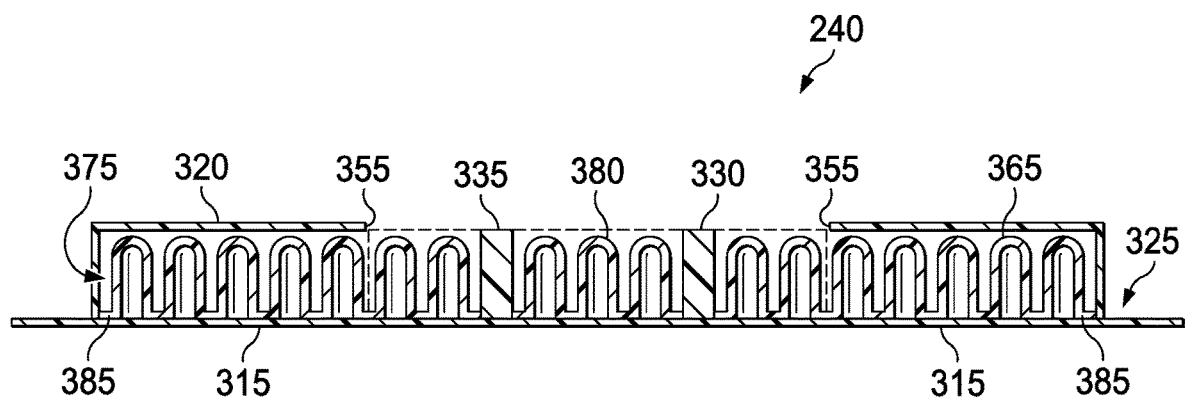
FIG. 3B is a schematic view of an applicator that may be associated with some embodiments of the bridge of FIG. 3A.

FIG. 3B is a schematic view of the applicator 240 of FIG. 3A, taken along line 3B-3B, illustrating additional details that may be associated with some embodiments. In FIG. 3B, the support layer may comprise a spacer layer 375 having the plurality of supports 365. For example, some embodiments of the support features may be formed by sealing the spacer layer 375 to the first layer 315. In the example of FIG. 3B, each of the supports 365 comprises a standoff 380 in the spacer layer 375. In some embodiments, the standoffs 380 may be formed by blisters, bubbles, cells or other raised formations that extend above or below a base 385 of the spacer layer 375, for example. In some examples, the standoffs 380 may be vacuum-formed regions of the spacer layer 375.

The base 385 may be sealed to the first layer 315, and the standoffs 380 may extend from the first layer 315 toward the aperture 355 of the second layer 320 as illustrated in FIG. 3B. At least some of the supports 365 may be configured to come in direct contact with the tissue interface 120 through the aperture 355.

In some embodiments, the base 385 may be sealed to the first layer 315 so that the first layer 315 closes the standoffs 380. For example, the base 385 may be heat-sealed to the first layer 315 while the standoffs 380 may be vacuum-formed simultaneously. In other examples, the seal may be formed by adhesion between the first layer 315 and the spacer layer 375. Alternatively, the first layer 315 and the spacer layer 375 may be adhesively bonded to each other.

In general, the supports 365 are structured so that they do not completely collapse from apposition forces resulting from the application of negative pressure and/or external forces to the bridge 160. In some examples, the first layer 315 and the spacer layer 375 may be formed from separate sheets or film brought into superposition and sealed, or they may be formed by folding a single sheet onto itself with a heat-sealable surface facing inward. Any one or more of the first layer 315, second layer 320, and the spacer layer 375 also may be a monolayer or multilayer structure, depending on the application or the desired structure of the support features.

In some example embodiments, the standoffs 380 may be substantially airtight to inhibit collapsing of the standoffs 380 under negative pressure, which could block the flow of fluid through the bridge 160. For example, in the embodiment of FIG. 3B, the standoffs 380 may be substantially airtight and have an internal pressure that is an ambient pressure. In another example embodiment, the standoffs 380 may be inflated with air or other suitable gases, such as carbon dioxide or nitrogen. The standoffs 380 may be inflated to have an internal pressure greater than the atmospheric pressure to maintain their shape and resistance to collapsing under pressure and external forces. For example, the standoffs 380 may be inflated to a pressure up to about 25 psi above the atmospheric pressure.

In some embodiments, the first layer 315, the second layer 320, and the spacer layer 375 may each have a thickness within a range of 400 to 600 microns. For example, the first layer 315, the second layer 320, and the spacer layer 375 may be formed from thermoplastic polyurethane film having a thickness of about 500 microns. In some example embodiments, each may have a thickness of about 200 μm to about 600 μm. In some embodiments, a thickness of about 500 μm or about 250 μm may be suitable.

In some embodiments, one or more of the first layer 315, the second layer 320, and the spacer layer 375 may have a different thickness. For example, the thickness of the second layer 320 may be up to 50% thinner than the thickness of the spacer layer 375. If the fabrication process comprises injection molding, portions of the spacer layer 375 defining the standoffs 380 may have a thickness between about 400 μm and about 500 μm. However, if the standoffs 380 are fabricated by drawing a film, the spacer layer 375 proximate a top portion of the standoffs 380 may have a thickness as thin as 50 μm.

After the standoffs 380 have been fabricated, the walls of the standoffs 380 may have a thickness relative to the thickness of base 385. The relative thickness may be defined by a draw ratio, such as the ratio of the average height of the standoffs 380 to the average thickness of the spacer layer 375. In some example embodiments, the standoffs 380 may have a generally tubular shape, which may have been formed from the spacer layer 375 having various thicknesses and draw ratios. In some example embodiments, the spacer layer 375 may have an average thickness of 500 μm and the standoffs 380 may have an average height in a range between about 2.0 mm and 5.0 mm. Consequently, the standoffs 380 may have a draw ratio ranging from about 4:1 to about 10:1 for heights of 2.0 and 5.0 mm, respectively. In another example embodiment, the draw ratio may range from about 5:1 to about 13:1 where the thickness of the spacer layer 375 is an average of about 400 μm. In yet other example embodiments, the draw ratio may range from about 3:1 to about 9:1 where the thickness of the spacer layer 375 is an average of about 600 μm. In some embodiments, the standoffs 380 may have an average height in a range between about 1.0 mm and 4.0 mm, depending on the thickness of the spacer layer 375. The spacer layer 375 may have varying thicknesses and flexibilities, but is substantially non-stretchable so that the standoffs 380 maintain a generally constant volume if sealed to the first layer 315. Additionally, the standoffs 380 can support a load without bursting and can recover their original shape after a load is removed.

In some example embodiments, any one or more of the first layer 315, the second layer 320, and the spacer layer 375 may be formed from a non-porous, polymeric film that may comprise any flexible material that can be manipulated to form suitable support features, including various thermoplastic materials, e.g., polyethylene homopolymer or copolymer, polypropylene homopolymer or copolymer, etc. Non-limiting examples of suitable thermoplastic polymers may include polyethylene homopolymers, such as low density polyethylene (LDPE) and high density polyethylene (HDPE), and polyethylene copolymers such as, e.g., ionomers, EVA, EMA, heterogeneous (Zeigler-Natta catalyzed) ethylene/alpha-olefin copolymers, and homogeneous (metallocene, single-cite catalyzed) ethylene/alpha-olefin copolymers. Ethylene/alpha-olefin copolymers are copolymers of ethylene with one or more comonomers selected from $C_3$ to $C_{20}$ alpha-olefins, such as 1-butene, 1-pentene, 1-hexene, 1-octene, methyl pentene and the like, in which the polymer molecules comprise long chains with relatively few side chain branches, including linear low density polyethylene (LLDPE), linear medium density polyethylene (LMDPE), very low density polyethylene (VLDPE), and ultra-low density polyethylene (ULDPE). Various other materials may also be suitable, such as polypropylene homopolymer or polypropylene copolymer (e.g., propylene/ethylene copolymer), polyesters, polystyrenes, polyamides, polycarbonates, etc.

In some embodiments, the polymeric film may possess sufficient tensile strength to resist stretching under apposition forces created by negative-pressure therapy. The tensile strength of a material is the ability of material to resist stretching as represented by a stress-strain curve where stress is the force per unit area, i.e., pascals (Pa), newtons per square meter ($N/m^2$), or pounds per square inch (psi). The ultimate tensile strength (UTS) is the maximum stress the material can withstand while being stretched before failing or breaking. Many materials display a linear elastic behavior defined by a linear stress-strain relationship often extending up to a nonlinear region represented by the yield point, i.e., the yield strength of a material. For example, high density polyethylene (HDPE) has a high tensile strength and low-density polyethylene (LDPE) has a slightly lower tensile strength, which are suitable materials for the sheets of non-porous, polymeric film as set forth above. Linear low density polyethylene (LLDPE) may also be suitable for some examples because the material stretches very little as the force is increased up to the yield point of the material. Thus, the standoffs 380 or other support features can be configured to resist collapsing (or stretching) when subjected to an external force or pressure. For example, HDPE has a UTS of about 37 MPa and may have a yield strength that ranges from about 26-33 MPa depending on the thickness of the material, while LDPE has somewhat lower values.

In some example embodiments, one or more of the first layer 315, the second layer 320, and the spacer layer 375 may comprise or consist essentially of a thermoplastic polyurethane (TPU) film that is permeable to water vapor but impermeable to liquid. The film may be in various degrees breathable and may have MVTRs that are proportional to their thickness. For example, the MVTR may be at least 300 g/m² per twenty-four hours in some embodiments. For permeable materials, the permeability generally should be low enough to maintain a desired negative pressure for the desired negative-pressure treatment.

In some example embodiments, the thermoplastic polyurethane film may be, for example, a Platilon® thermoplastic polyurethane film available from Convestro LLC, which may have a UTS of about 60 MPa and may have a yield strength of approximately 11 MPa or greater than about 10 MPa depending on the thickness of the material. Therefore, in some example embodiments, it is desirable that the non-porous, polymeric film may have a yield strength greater than about 10 MPa, depending on the type and thickness of material. A material having a lower yield strength may be too stretchable and, therefore, more susceptible to breaking with the application of small amounts of compression and/or apposition forces.

Figure 3C:
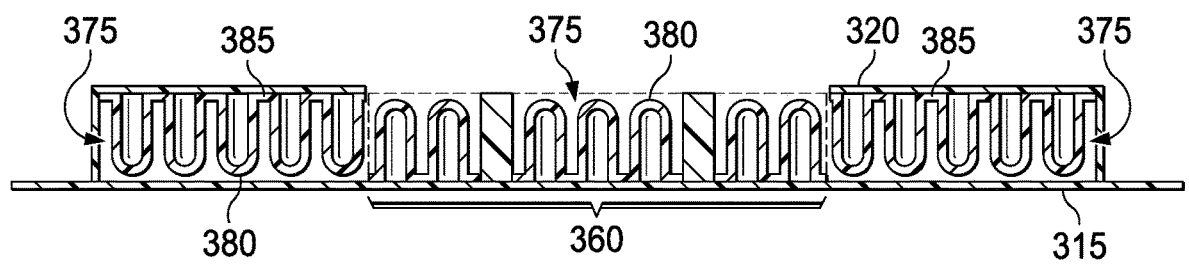
FIG. 3C is a schematic view of another example of an applicator that may be associated with some embodiments of the bridge of FIG. 3A.

FIG. 3C is a schematic view of another example of the applicator 240, illustrating details that may be associated with some embodiments. In the example of FIG. 3C, the applicator 240 has more than one spacer layer 375. At least some of the support features may be formed by sealing the base 385 of at least one of the spacer layers 375 to the second layer 320. Some of the supports 365 may extend from the second layer 320 toward the first layer 315 around the recessed space 360. In the example of FIG. 3C, all of the supports 365 around the recessed space 360 extend from the second layer 320 toward the first layer 315. At least some of the supports 365 may also extend from the first layer 315 toward the aperture 355 in the recessed space 360.

Figure 3D:
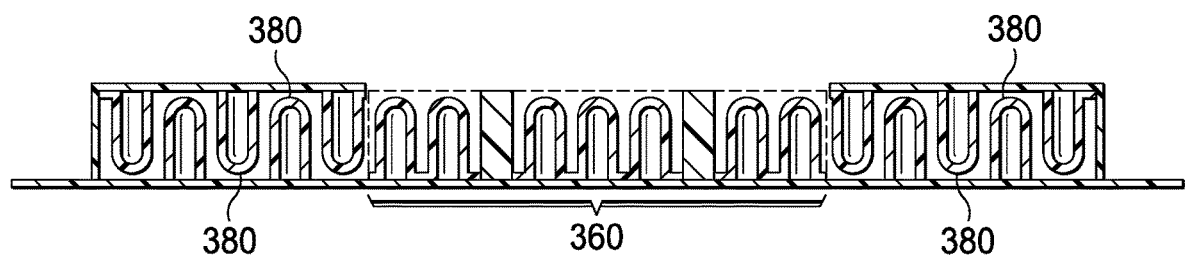
FIG. 3D is a schematic view of another example of an applicator that may be associated with some embodiments of the bridge of FIG. 3A.

FIG. 3D is a schematic view of another example of the applicator 240, illustrating additional details that may be associated with some embodiments. In the example of FIG. 3D, some of the supports 365 around the recessed space 360 extend from the second layer 320 toward the first layer 315, and some of the supports 365 around the recessed space 360 also extend from the first layer 315 toward the second layer 320. Some of the supports 365 also extend from the first layer 315 toward the aperture 355 in the recessed space 360.

Figure 4A:
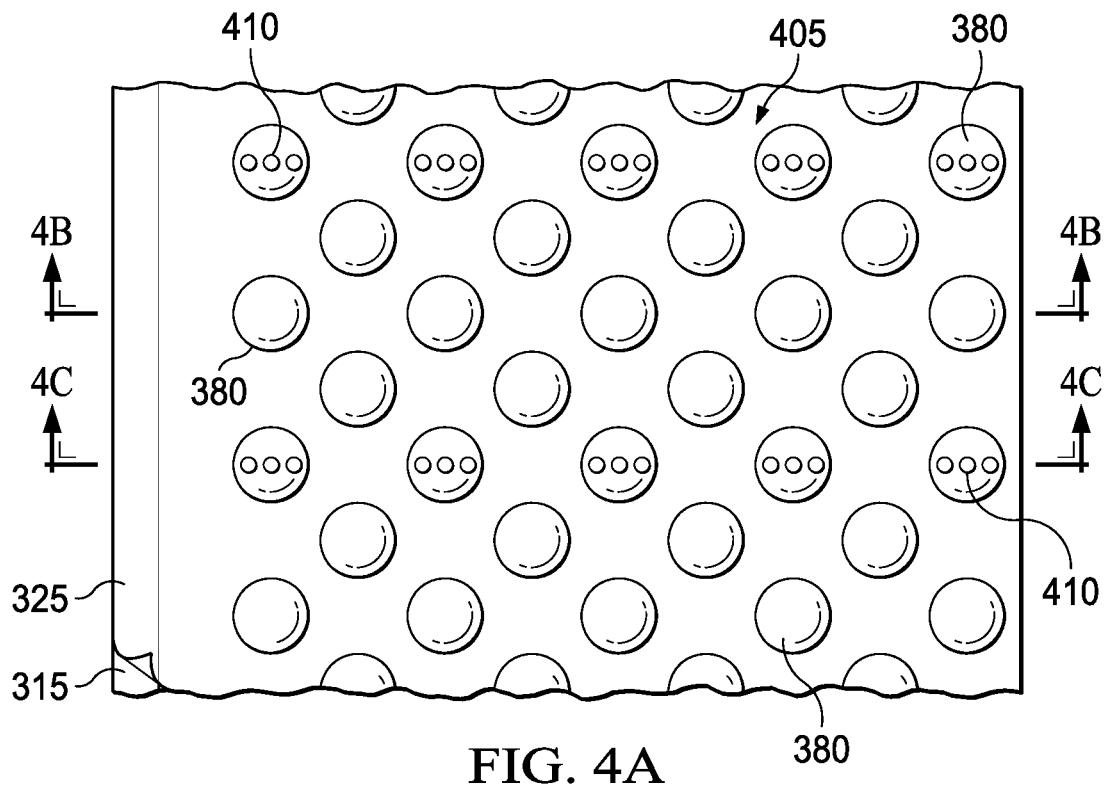
FIG. 4A is a schematic view of additional details that may be associated with various examples of support features in a bridge.

FIG. 4A is a schematic view of additional details that may be associated with various examples of support features in the bridge 160. For example, FIG. 4A illustrates a sealed region 405 between the standoffs 380. In some embodiments, the sealed region 405 may be formed by sealing portions of the spacer layer 375 to the first layer 315 or the second layer 320. In the example of FIG. 4A, the sealed region 405 may be formed by sealing the base 385 to the first layer 315 around the standoffs 380. As illustrated in the example of FIG. 4A, the standoffs 380 may have a circular edge proximate to the sealed region 405. In other embodiments, the standoffs 380 may have edges with other suitable shapes, such as rectangular, triangular, or hexagonal, or some combination of shapes. Additionally or alternatively, one or more of the standoffs 380 may be embossed with projections or nodes, such as the nodes 410 illustrated in the example of FIG. 4A.

The standoffs 380 in adjacent rows or columns may be staggered so that the standoffs 380 may be nested or packed together, as illustrated in the example of FIG. 4A. In other embodiments, the standoffs 380 may be arranged in other patterns suitable for the particular therapy being utilized. For example, the rows and columns of the standoffs 380 may be arranged in line to form an aligned, rectangular pattern so that there is more spacing between the standoffs 380. Increasing the spacing between the standoffs 380 may increase fluid flow within the fluid pathways of the bridge 160, whereas a nested arrangement may restrict fluid flow within the fluid pathways. For example, the standoffs 380 can be aligned to increase fluid flow of negative pressure being applied to a tissue interface and facilitate the removal of fluids and exudates within the recessed space 360. A nested pattern can facilitate pressure sensing within the recessed space 360 while impeding the inflow of fluids and exudates, which can reduce the possibility of blockage.

In some embodiments, distribution of the standoffs 380 may be characterized by a pitch, which can be defined by the center to center distance between each of the standoffs 380. For example, a pitch of about 1 mm to about 10 mm may be suitable for some configurations. In some embodiments, the pitch may be between about 2 mm and about 3 mm. Because the sealed region 405 can define an end of the standoffs 380, including a diameter of a circular end, and the pitch of the standoffs 380, the area of the spacer layer 375 having the standoffs 380 may also be determined as a percentage. For example, if each of the standoffs 380 has a diameter of about 1.0 mm and the pitch is about 2.0 mm, the coverage percentage is about 22% of the area of the spacer layer 375. In another example, if the diameter of each of the standoffs 380 is about 2.0 mm and the pitch is about 5.0 mm, the coverage percentage is about 14% of the area of the spacer layer 375. In yet another example, if the diameter of each of the standoffs 380 is about 1.5 mm, the pitch is about 2.0 mm, and the standoffs 380 are more tightly arranged such that there are about 28.5 standoffs in a 10 mm² section of the spacer layer 375, the coverage percentage is about 51% of the area of the spacer layer 375. Depending on the diameter, pitch, and arrangement of the standoffs 380, the coverage percentage may range between about 10% and about 60% of the surface area of the spacer layer 375. Support features having other shapes also may have a coverage percentage in generally the same range.

The size and pitch of the standoffs 380 also may be varied to effect change in the fluid flows through the fluid passageways. For example, the diameter and pitch of the standoffs 380 can be increased to increase fluid flow of negative pressure being applied to a tissue interface and facilitate the removal of fluids and exudates within the recessed space 360. The diameter, pitch, or both may be decreased to restrict fluid flow, which can reduce blockages, and facilitate pressure sensing within the recessed space 360.

Figure 4B:
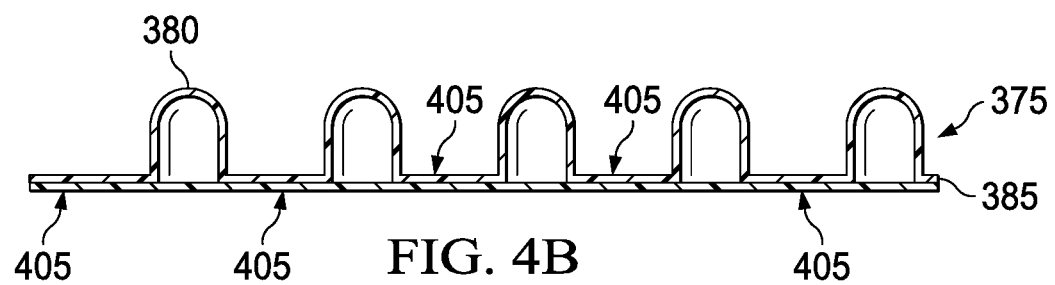
FIG. 4B is a schematic view of the support features of FIG. 4A taken along section 4B-4B, illustrating additional details that may be associated with some examples.

FIG. 4B is a schematic view of the support features of FIG. 4A taken along section 4B-4B, illustrating additional details that may be associated with some examples. In some embodiments, the standoffs 380 may have a hemispherical profile, as illustrated in the example of FIG. 4B. In other example embodiments, the standoffs 380 may be profiles that are conical, cylindrical, tubular having a flattened or hemispherical end, or geodesic. The standoffs 380 may be tubular in some embodiments, formed with generally parallel walls extending from the base 385 to a hemispherical or flat top portion of the standoffs 380. Alternatively, the walls of the standoffs 380 may taper or expand outwardly from the base 385. In some embodiments, the standoffs 380 that are generally hemispherical or tubular in shape may have a diameter between about 1.0 mm and about 10 mm. In some other embodiments, the standoffs 380 may have a diameter between about 2.0 mm and about 5.0 mm.

Figure 4C:
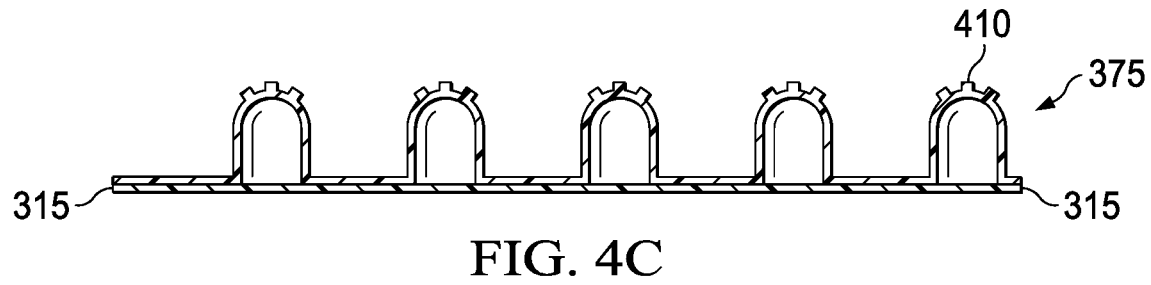
FIG. 4C is a schematic view of the example support features of FIG. 4A taken along section 4C-4C, illustrating additional details that may be associated with some embodiments.

FIG. 4C is a schematic view of the example support features of FIG. 4A taken along section 4C-4C, illustrating additional details that may be associated with some embodiments. In the example of FIG. 4C, the nodes 410 can be configured to contact the tissue interface 120 to enhance fluid flow to a tissue site. The nodes 410 may be flexible or rigid. In some embodiments, the nodes 410 may be formed from a substantially gas impermeable material, such as silicone. In other embodiments, the nodes 410 may be formed from a semi-gas permeable material. The nodes 410 may be formed from the same material as the spacer layer 375, and may be an integral part of the spacer layer 375. In some embodiments, the nodes 410 may be solid, while in other embodiments the projections may be hollow to increase flexibility. The nodes 410 may form a plurality of channels and/or voids to distribute reduced pressure and allow for fluid flow among the nodes 410. The nodes may be dimensioned to provide local load points evenly distributed at a tissue interface. The pattern and position of the nodes 410 may be uniform or non-uniform. The nodes may have different profiles, including, for example, the shape of a spike, cone, pyramid, dome, cylinder or rectangle.

Figure 5A:
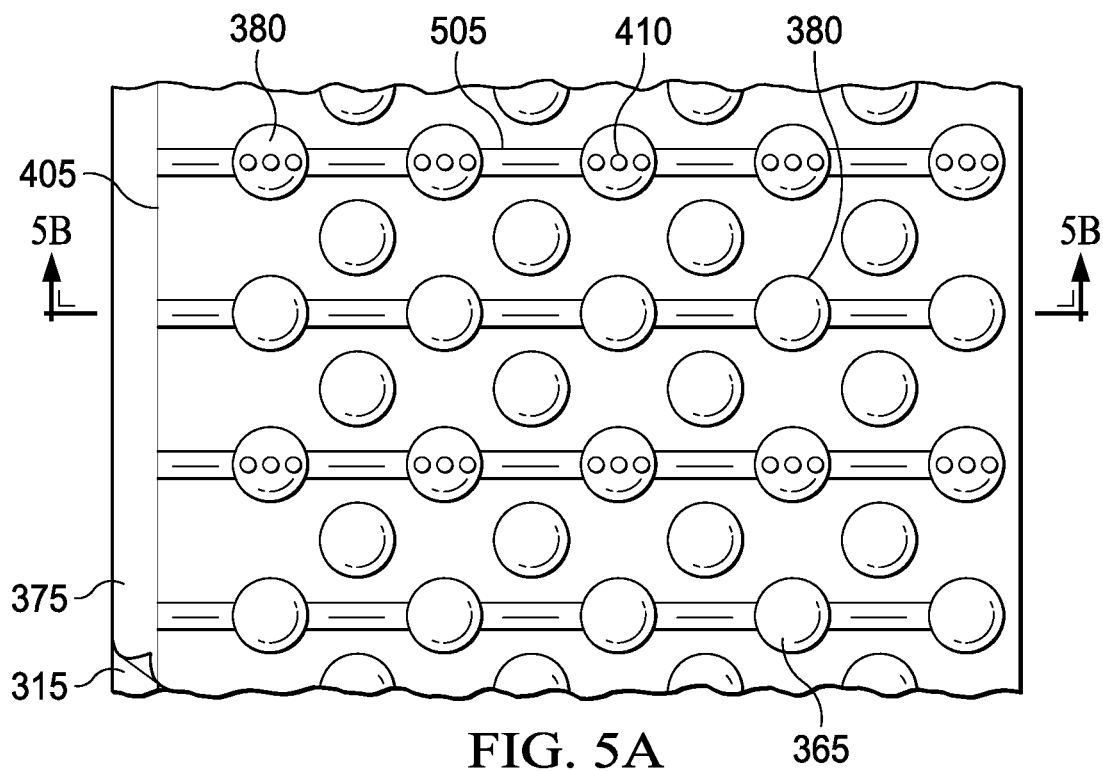
FIG. 5A is a schematic view of additional details that may be associated with some embodiments of a bridge in the therapy system of FIG. 1.

FIG. 5A is a schematic view of additional details that may be associated with some embodiments of the bridge 160. For example, in FIG. 5A one or more passageways 505 may be formed between the supports 365.

Figure 5B:
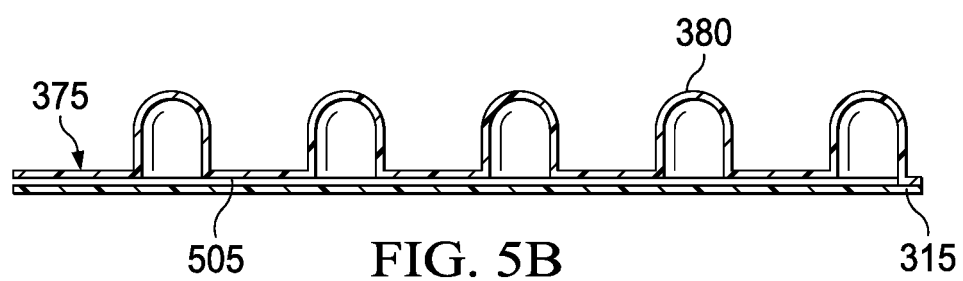
FIG. 5B is a schematic view taken along section 5B-5B of FIG. 5A, illustrating additional details that may be associated with some embodiments.

FIG. 5B is a schematic view taken along section 5B-5B of FIG. 5A, illustrating additional details that may be associated with some embodiments. For example, as seen in FIG. 5B, at least some of the standoffs 380 may be fluidly coupled through the passageways 505. The passageways 505 and the standoffs 380 can form a closed chamber. In some examples, a closed chamber may be formed by all of the standoffs 380 in a row fluidly coupled by the passageways 505 as shown in FIG. 5A and FIG. 5B. The closed chambers may be formed in alternating rows as also shown in FIG. 5A. The formation of closed chambers with the standoffs 380 can distribute apposition forces more equally.

Figure 6A:
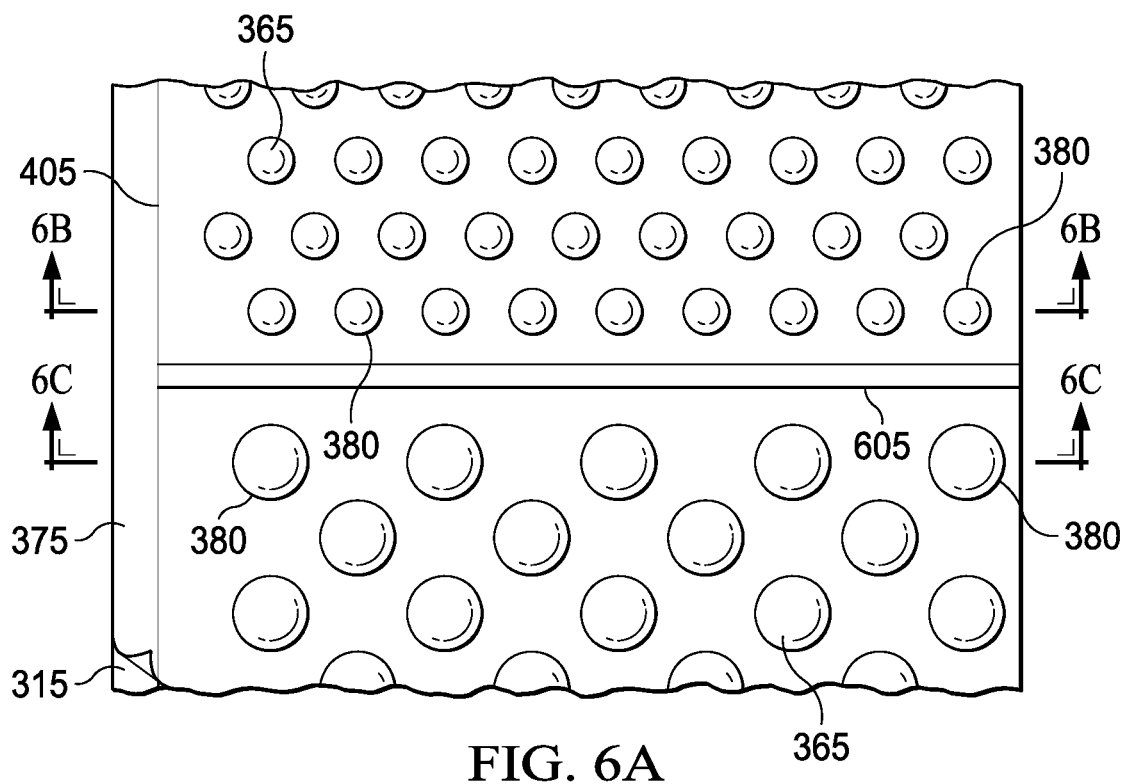
FIGS. 6A, 6B, and 6C illustrate other examples of features that may be associated with some embodiments of a bridge in the therapy system of FIG. 1.
Figure 6B:
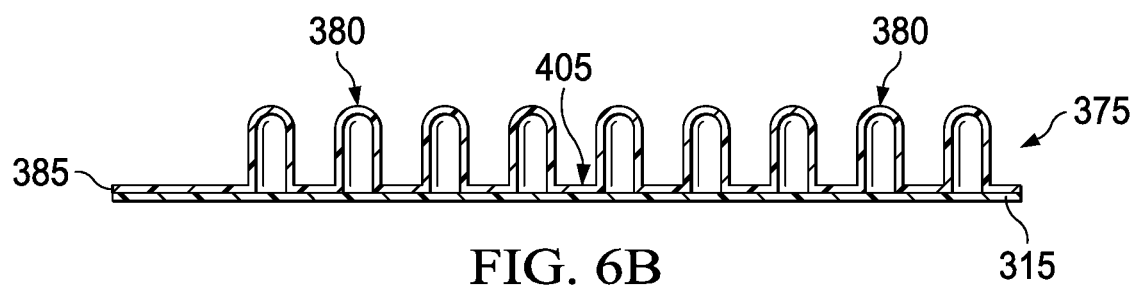
Figure 6C:
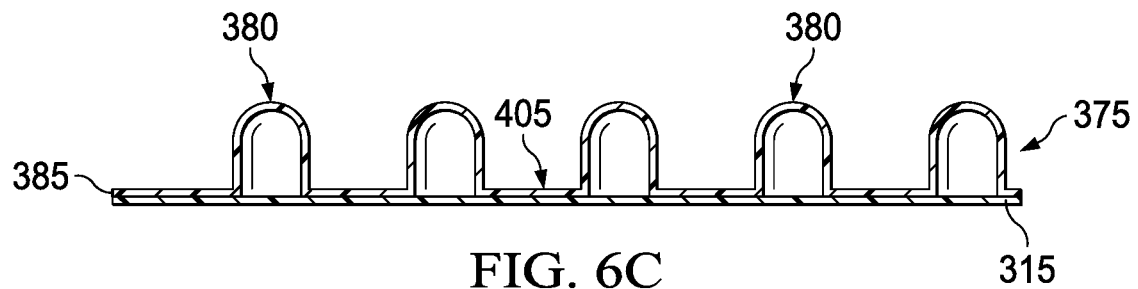

FIGS. 6A, 6B, and 6C illustrate other examples of features that may be associated with some embodiments of the bridge 160. In FIG. 6A, the first layer 315 and the spacer layer 375 define a nested arrangement of the supports 365. The example of FIG. 6A further illustrates that at least some of the supports 365 may additionally or alternatively have different sizes. For example, some of the supports 365 may have a diameter in the range between about 1 mm and about 10 mm, and some of the supports 365 may have a diameter in the range between about 1 mm and about 3 mm. In some embodiments, a wall 605 may be disposed between some of the supports 365. For example, the wall 605 in the example of FIG. 6A is disposed between the supports 365 having different sizes. The supports 365 having a larger diameter and pitch may increase fluid flow to facilitate the removal of fluids and exudates within the recessed space 360 in some embodiments. In some embodiments, the supports 365 having a smaller diameter and pitch may restrict fluid flow to facilitate pressure sensing within the recessed space 360 while impeding the inflow of fluids and exudates into the first pathway 340. The arrangement and dimensions of the supports 365 may be tailored to manage the delivery of negative pressure to the tissue interface 120 and the measurement of pressure within the recessed space 360.

Figure 7:
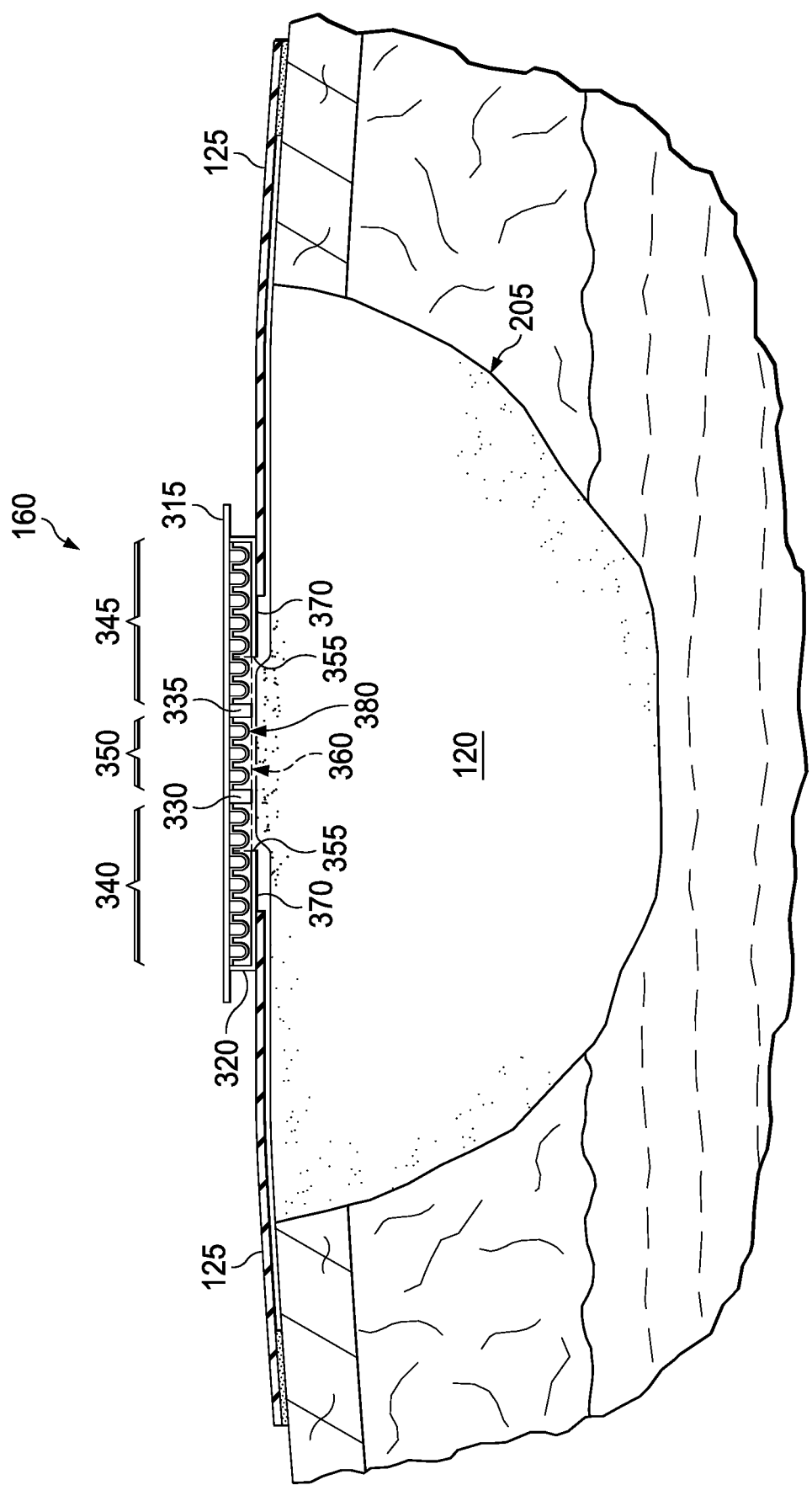
FIG. 7 is a schematic diagram of the bridge of FIG. 3A applied to a tissue site with negative pressure.

FIG. 7 is a schematic diagram of the bridge 160 of FIG. 3A applied to the tissue site 205 with negative pressure. The tissue interface 120 may be in fluid communication with the recessed space 360 through the aperture 355. The affixation surface 370 may be coupled to the cover 125 to seal and fluidly couple the recessed space 360 to the tissue interface 120. In the example of FIG. 7, the first wall 330 and the second wall 335 partially define the first pathway 340, the second pathway 345, and the third pathway 350 between the first layer 315 and the second layer 320.

Within the recessed space 360, the standoffs 380 can extend from the first layer 315 toward the tissue interface 120 and may be adapted to come in direct contact with the tissue interface 120 if negative pressure is applied to the bridge 160. Negative pressure can compress the bridge 160, and the first layer 315 and the second layer 320 can collapse toward each other because of the vacuum created within the standoffs 380. Although the standoffs 380 may change shape or flatten somewhat under negative pressure, the volume of the standoffs 380 remains substantially constant and can maintain fluid flow through the third pathway 350. The standoffs 380 can also provide a cushion to help prevent the sealed spaces of the bridge 160 from collapsing as a result of external forces. The standoffs 380 disposed in the third pathway 350 may be sized and arranged in a pattern that may increase fluid flow of negative pressure being applied to the tissue interface 120 to facilitate the removal of fluids and exudates within the recessed space 360. The standoffs 380 disposed in the first pathway 340 and the second pathway 345 may be sized and arranged in a pattern to facilitate pressure sensing within the recessed space 360 while impeding the inflow of fluids and exudates into the first pathway 340 and the second pathway 345 to reduce blockage conditions.

The standoffs 380 may have a variety of shapes, and may be sized and arranged in different patterns within the sealed space to enhance the delivery of negative pressure to the tissue interface 120 for a specific type of tissue site while optimizing pressure sensing and measurement of the negative pressure within the recessed space 360.

Figure 8:
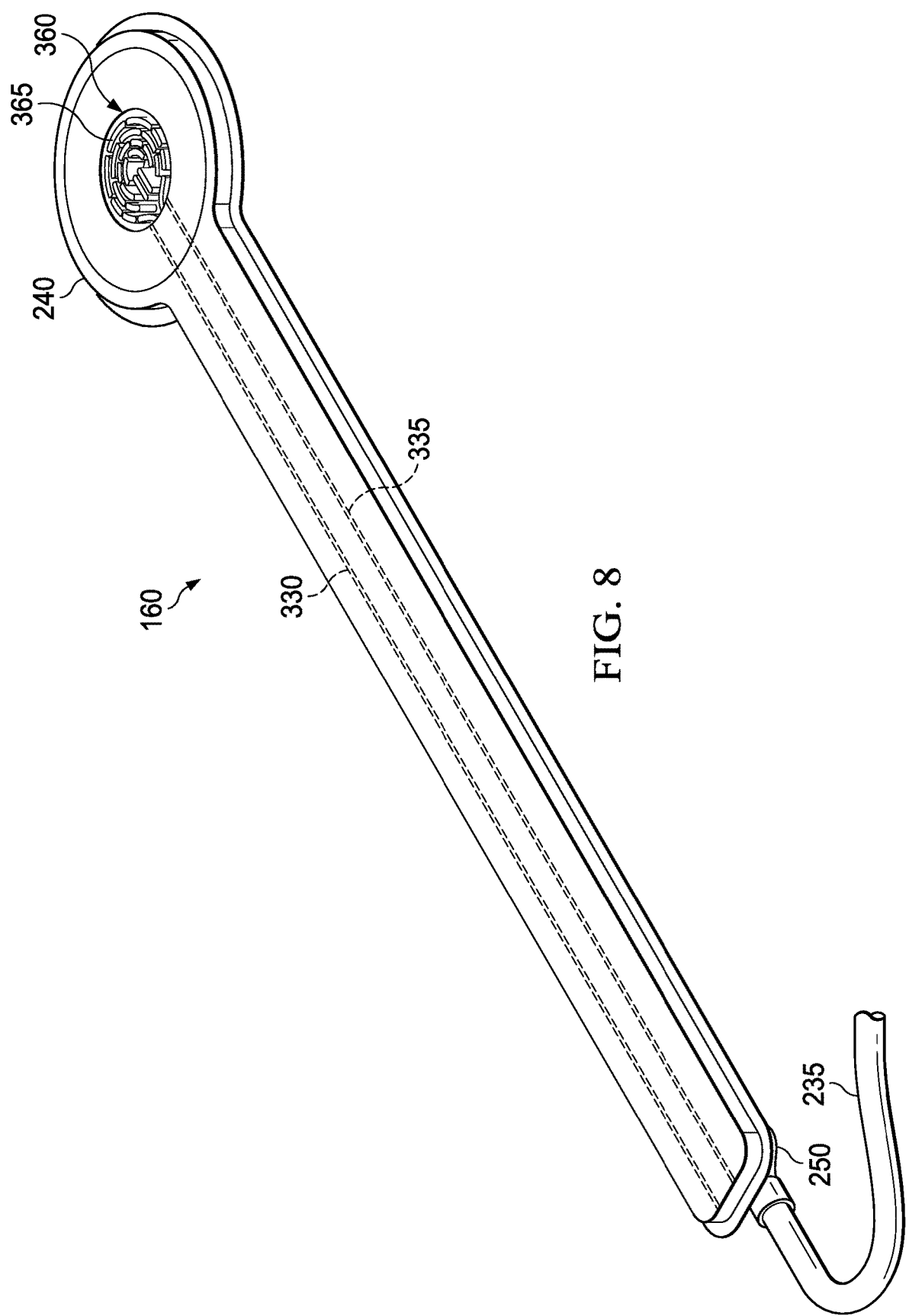
FIG. 8 is an isometric bottom view of another example of a bridge that may be associated with some embodiments of the therapy system of FIG. 1.

FIG. 8 is a perspective bottom view of another example of the bridge 160 having a low-profile structure that may be associated with some embodiments of the therapy system 100. As illustrated in the example of FIG. 8, the first wall 330 and the second wall 335 may extend lengthwise through the bridge 160 between the recessed space 360 and the adapter 250.

Figure 9A:
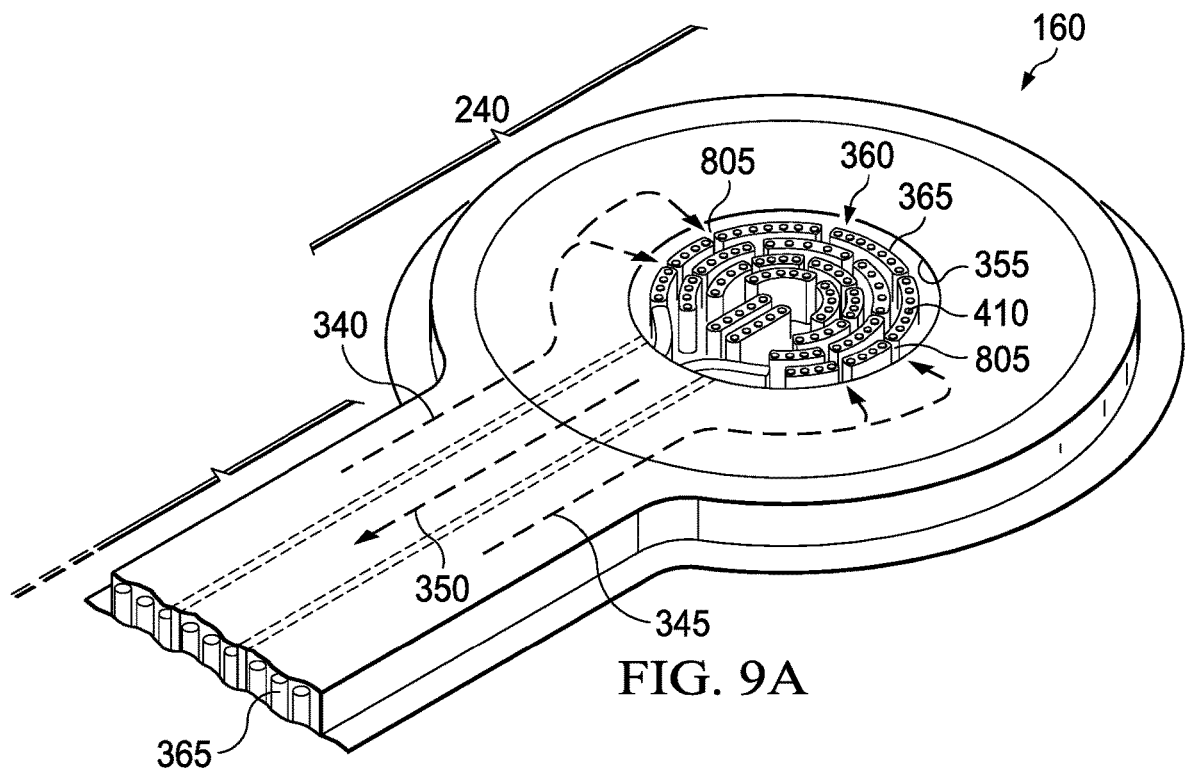
FIG. 9A and FIG. 9B are segmented isometric views of the bridge of FIG. 8.
Figure 9B:
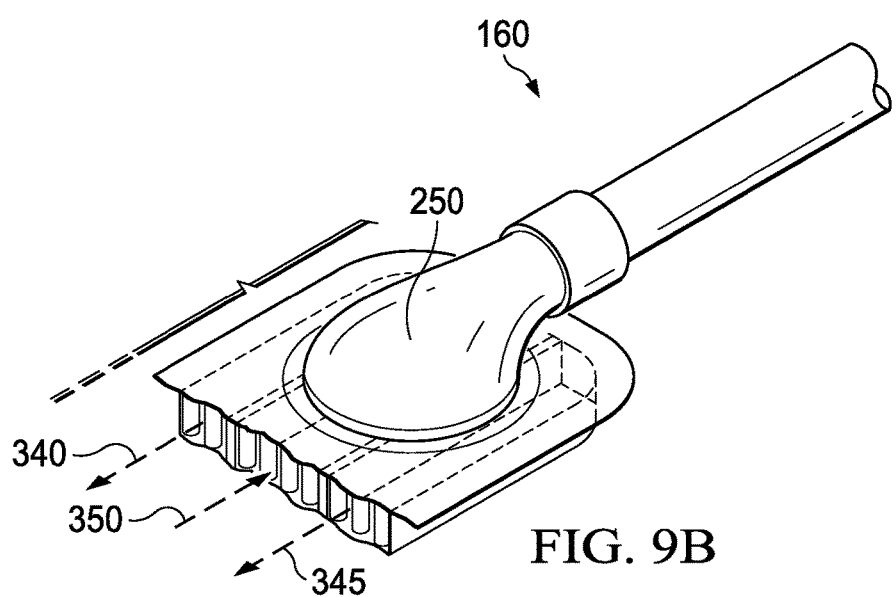

FIG. 9A and FIG. 9B are segmented perspective views of the bridge 160 of FIG. 8, illustrating additional details that may be associated with some examples. FIG. 9A is a bottom perspective view of an example of the applicator 240, illustrating a configuration having a circular profile. FIG. 9B is a top perspective view of an example of the adapter 250, which may have an elbow connector of semi-rigid material in some embodiments.

The aperture 355 of FIG. 9A is generally circular and opens to the recessed space 360. The supports 365 of FIG. 9A may have a generally elongated and arcuate profile and may be arranged in a generally concentric pattern within the recessed space 360. Some embodiments of the supports 365 may also comprise surface features, such as the nodes 410. The supports 365 disposed in the center of the recessed space 360 may be more aligned with the third pathway 350 to increase fluid flow of negative pressure being applied to the tissue interface 120 and facilitate the removal of fluids and exudates within the recessed space 360. In some embodiments, some of the supports 365 may be disposed around the aperture 355 to form a semicircular path opposite the third pathway 350, including spaces 805 between the supports 365. The semicircular alignment of the supports 365 may be positioned within the recessed space 360 to minimize contact with the flow of fluids passing through from the tissue interface 120 to the third pathway 350 if negative pressure is applied. Additionally, the spaces 805 may be sufficiently small for further restricting fluid flow into the first pathway 340 and the second pathway 345, as indicated by the dashed arrows. The spaces 805 can facilitate pressure sensing within the recessed space 360 while impeding the inflow of fluids and exudates into the first pathway 340 and the second pathway 345 to reduce the possibility of blockage. In some embodiments, a portion of the perimeter of the aperture 355 may be welded to an outer ring of the supports 365 to further restrict fluid flow to the first pathway 340 and the second pathway 345 and further impede the inflow of fluids and exudates without inhibiting pressure sensing within the recessed space 360.

Figure 10:
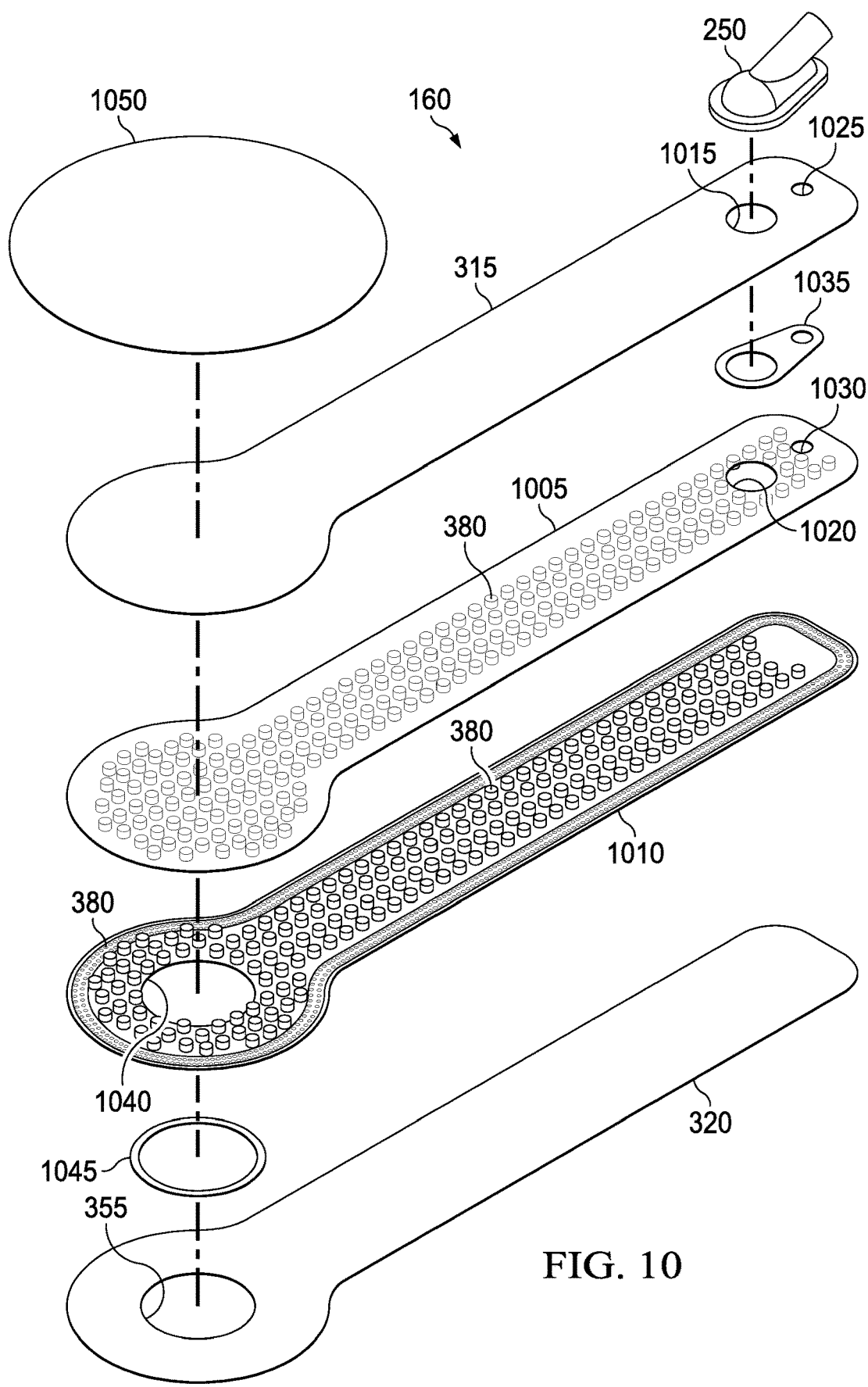
FIG. 10 is an assembly view of another example of a bridge that may be associated with some example embodiments of the therapy system of FIG. 1.

FIG. 10 is an assembly view of another example of the bridge 160 having a low-profile structure that may be associated with some example embodiments of the therapy system 100. In the example of FIG. 10, the bridge 160 comprises two spacer layers—a first spacer layer 1005 and a second spacer layer 1010—disposed between the first layer 315 and the second layer 320. In some embodiments, the first spacer layer 1005 and the second spacer layer 1010 may each be similar to spacer layer(s) 375. For example, standoffs 380 may be formed in each of the first spacer layer 1005 and the second spacer layer 1010. In the example of FIG. 10, the standoffs 380 in the first spacer layer 1005 are configured to extend toward the second spacer layer 1010, and the standoffs 380 in the second spacer layer 1010 are configured to extend toward the first spacer layer 1005. The first layer 315 may have a passage 1015, and the first spacer layer 1005 may have a passage 1020, through which fluids may flow to the adapter 250. The first layer 315 and the first spacer layer 1005 may additionally have a passage 1025 and a passage 1030, respectively, which may also be fluidly coupled to the adapter 250. The bridge 160 may further comprise a fluid exit bond 1035 to prevent leakage of fluids flowing through the passage 1015 and the passage 1020. The second spacer layer 1010 may have an aperture 1040 concentric with the aperture 355 of the second layer 320. The bridge 160 may further comprise a fluid exit bond 1045, which can prevent leakage of fluids flowing through the aperture 355 and the aperture 1040.

In some embodiments, a bridge cover 1050 may provide additional protection and support over the applicator 240 if the bridge 160 is applied to a tissue site. In some embodiments, the bridge cover 1050 may also cover any adhesive that might be exposed from applying the bridge 160 to a tissue site. In some embodiments, the bridge cover 1050 may be similar or analogous to the cover 125. For example, the bridge cover 1050 may be a polymer, such as a polyurethane film.

Figure 11A:
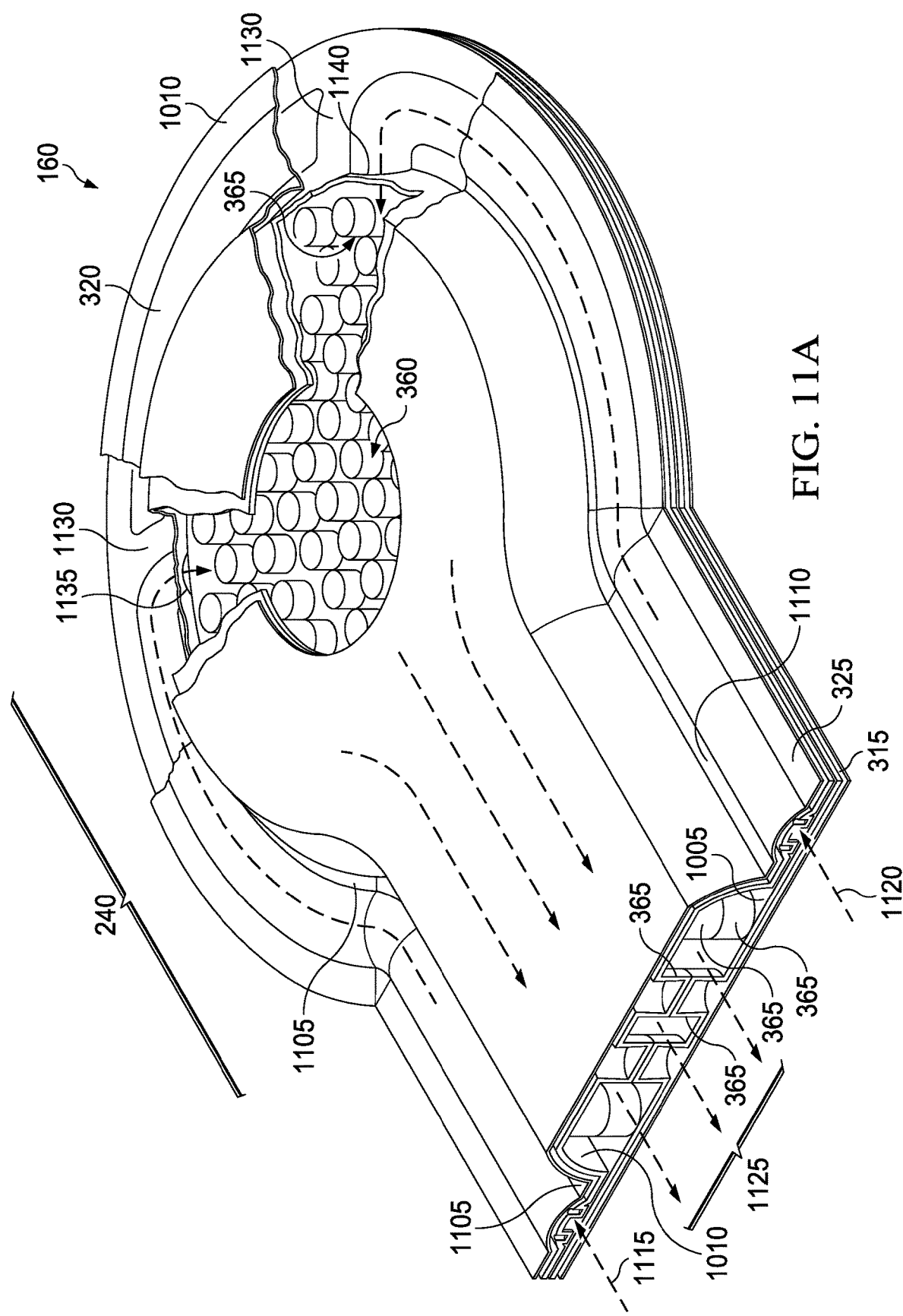
FIG. 11A is a segmented view of an assembled portion of the bridge in the example of FIG. 10, illustrating additional details that may be associated with some embodiments.

FIG. 11A is a segmented view of an assembled portion of the bridge 160 in the example of FIG. 10, illustrating additional details that may be associated with some embodiments. As illustrated in the example of FIG. 11A, the first layer 315, second layer 320, the first spacer layer 1005, and the second spacer layer 1010 may be assembled in a stacked relationship. For example, the first layer 315 may be coupled to the first spacer layer 1005, the second layer 320 may be coupled to the second spacer layer 1010, and a periphery of the first spacer layer 1005 may be coupled to a periphery of the second spacer layer 1010 to form the flange 325. The first spacer layer 1005 and the second spacer layer 1010 can be coupled to form a liquid barrier defining a fluid path along a longitudinal axis of the bridge 160.

Some embodiments of the bridge 160 may additionally comprise at least one barrier or wall, such as a first barrier 1105, interior to the flange 325. The first barrier 1105 may be formed by coupling the first spacer layer 1005 and the second spacer layer 1010. For example, the first spacer layer 1005 may be welded to the second spacer layer 1010 to form the first barrier 1105. In some embodiments, the first barrier 1105 may extend lengthwise through the bridge 160 into the applicator 240 to form at least two fluid paths between the first spacer layer 1005 and the second spacer layer 1010 within the bridge 160. In some examples, the bridge 160 may further comprise a second barrier, such as a second barrier 1110. The second barrier 1110 may be formed by coupling the first spacer layer 1005 and the second spacer layer 1010. In some embodiments, the second barrier 1110 also may extend lengthwise through the bridge 160 into the applicator 240. In some example embodiments, the first barrier 1105 and the second barrier 1110 may comprise a polymeric film coupled between the first layer 315 and the second layer 320. In some other example embodiments, the first barrier 1105 and the second barrier 1110 may comprise a weld (RF or ultrasonic), a heat seal, an adhesive bond, or a combination of any of the foregoing. The first barrier 1105 and the second barrier 1110 may be similar to the first wall 330 and the second wall 335 in some embodiments.

In some embodiments, barriers or walls interior to the flange 325 may form fluid pathways between the first spacer layer 1005 and the second spacer layer 1010. For example, in FIG. 11A, the first barrier 1105 and the second barrier 1110 cooperate with the flange 325 to form a first fluid conductor 1115, a second fluid conductor 1120, and a third fluid conductor 1125. In some applications, the first fluid conductor 1115 and the second fluid conductor 1120 may be coupled to a sensor to measure pressure, and the third fluid conductor 1125 may be coupled to a negative-pressure source. In some example embodiments, the first fluid conductor 1115 and the second fluid conductor 1120 may have a height having a value in a range between about 0.25 mm and about 3 mm. In some example embodiments, the first fluid conductor 1115 and the second fluid conductor 1120 may have a width having a value in a range between about 1 mm and about 7.5 mm. Thus, the first fluid conductor 1115 and the second fluid conductor 1120 may have a cross-sectional area having a value in a range between about 0.17 $mm^2$ and 16.77 $mm^2$. In some embodiments, the first fluid conductor 1115 and the second fluid conductor 1120 may have a cross-sectional area having a value in a range between about 0.1 $mm^2$ and 18 $mm^2$.

In some examples, each of the first barrier 1105 and the second barrier 1110 may extend an angular distance around the proximal end of the applicator 240 and cooperate with blocking walls of the flange 325, such as blocking walls 1130, to form extensions of the first fluid conductor 1115 and the second fluid conductor 1120. The extensions may be fluidly coupled to the recessed space 360. In the example of FIG. 11A, the first fluid conductor 1115 and the second fluid conductor 1120 are fluidly coupled to the recessed space 360 through passages, such as a through-hole 1135 and a through-hole 1140, respectively. In some examples, at least some of the supports may be disposed in one or both of the first fluid conductor 1115 and the second fluid conductor 1120. For example, some of the supports may be formed by the standoffs 380 disposed between the flange 325 and the first barrier 1105, and between the flange 325 and the second barrier 1110. Additionally or alternatively, the thickness of the spacer layer 1010 may be increased to provide additional structural support to the first fluid conductor 1115 and the second fluid conductor 1120. In some examples, the first fluid conductor 1115 and the second fluid conductor 1120 may comprise or be formed by tubes through or along the bridge 160. Some configurations may not have the first fluid conductor 1115 or the second fluid conductor 1120, or may have only one of the first fluid conductor 1115 and the second fluid conductor 1120.

Each of the first barrier 1105 and the second barrier 1110 can extend at least partially around the proximal end of the applicator 240 that form the first fluid conductor 1115 and the second fluid conductor 1120. For example, in some embodiments each of the first barrier 1105 and the second barrier 1110 can extend from about 45° to about 315° from the center of the third fluid conductor 1125 where the third fluid conductor 1125 is in fluid communication with the recessed space 360. In some embodiments, the angular distance may be different for each of the first fluid conductor 1115 and the second fluid conductor 1120. For example, the angular distance for each of the first fluid conductor 1115 and the second fluid conductor 1120 may be about 60° and 210°, respectively, from the third fluid conductor 1125.

In some example embodiments, the through-hole 1135 and the through-hole 1140 may be separated from each other by an angular distance of at least 90°, extending around the applicator 240 in a direction away from the third fluid conductor 1125. The spacing and disposition of the through-hole 1135 and the through-hole 1140 from each other, and from the third fluid conductor 1125, can allow the first fluid conductor 1115 and the second fluid conductor 1120 to better avoid the flow of fluids passing through from the tissue interface 120 to the third fluid conductor 1125 when negative pressure is applied. Additionally, the through-hole 1135 and the through-hole 1140 may be sufficiently small for further restricting fluid flow into the first fluid conductor 1115 and the second fluid conductor 1120. In some embodiments, the through-hole 1135 and the through-hole 1140 may have a cross-sectional area having a value in a range between about 0.17 mm$^2$ and 16.77 mm$^2$. In some embodiments, the through-hole 1135 and the through-hole 1140 may have a cross-sectional area having a value in a range between about 0.1 mm$^2$ and 18 mm$^2$ to further restrict fluid flow to the first fluid conductor 1115 and the second fluid conductor 1120 and impede the inflow of fluids and exudates without inhibiting pressure sensing within the recessed space 360.

Figure 11B:
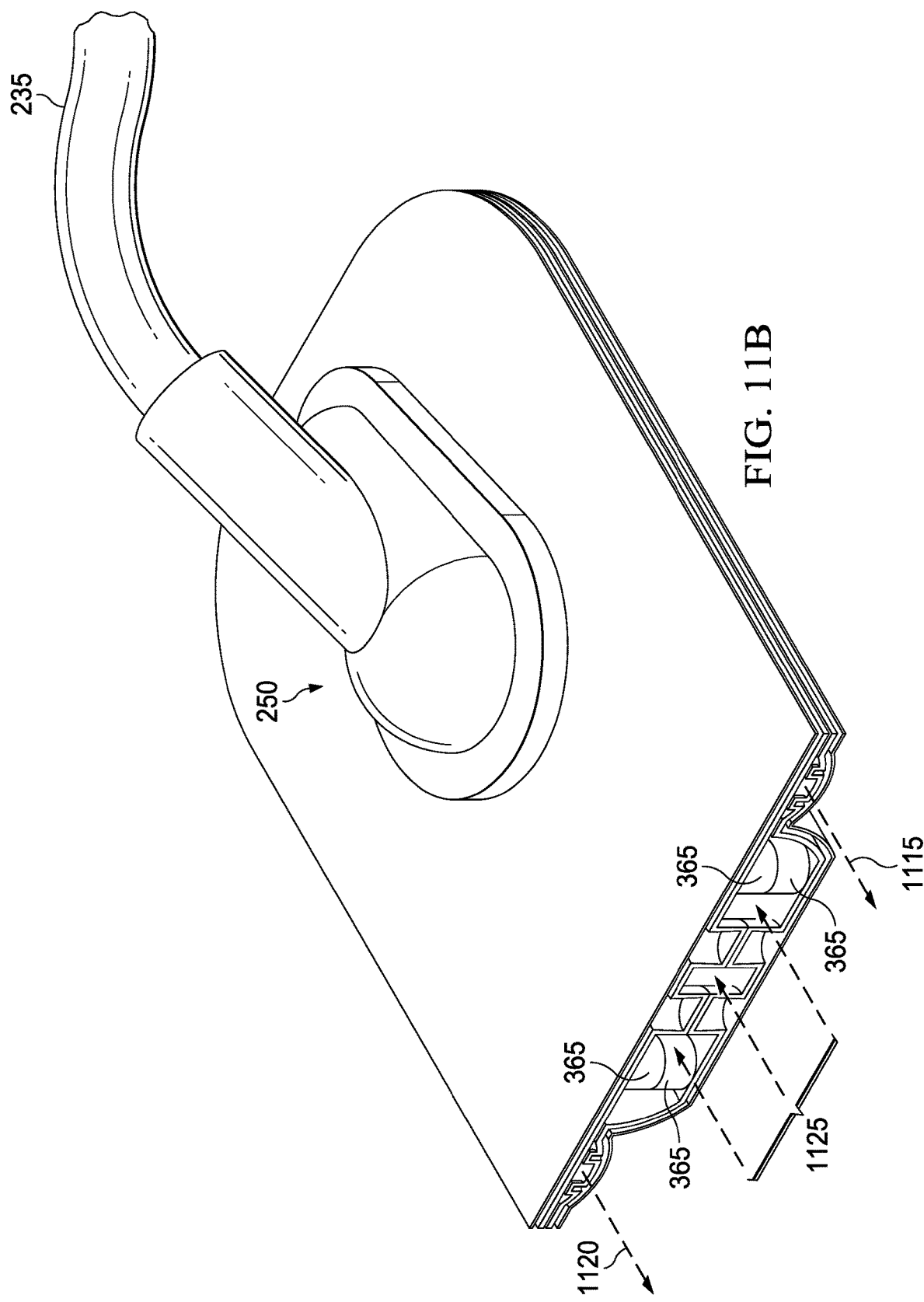
FIG. 11B is a segmented isometric view of portion of the bridge in the example of FIG. 10, illustrating additional details that may be associated with some embodiments.

FIG. 11B is a segmented perspective view of portion of the bridge 160 in the example of FIG. 10, illustrating additional details that may be associated with some embodiments. FIG. 11B further illustrates an example of the adapter 250 and the conduit 235 coupled to the bridge 160. Each of the first fluid conductor 1115 and the second fluid conductor 1120 may be fluidly coupled directly to the conduit 235 in some examples. In other examples, both of the first fluid conductor 1115 and the second fluid conductor 1120 may be fluidly coupled to a single space (not shown) within the adapter 250, which can be fluidly coupled to the conduit 235.

In the example of FIG. 11A and FIG. 11B, both the first fluid conductor 1115 and the second fluid conductor 1120 are fluidly separate from and parallel to the third fluid conductor 1125. The parallel orientation can minimize the vertical profile of the bridge 160, while still being resistant to collapsing under pressure that could block fluid flow through the fluid pathways.

Figure 12A:
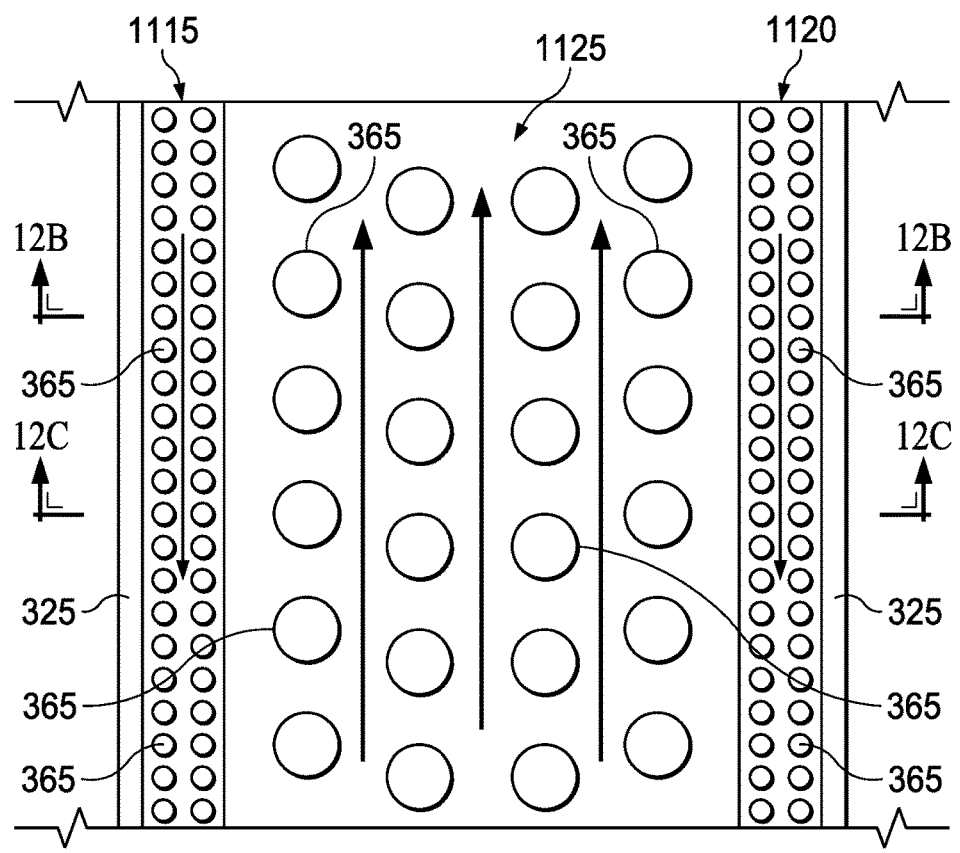
FIG. 12A is a schematic view of an example configuration of fluid pathways in the bridge of FIG. 10 as assembled, illustrating additional details that may be associated with some embodiments.
Figure 12B:
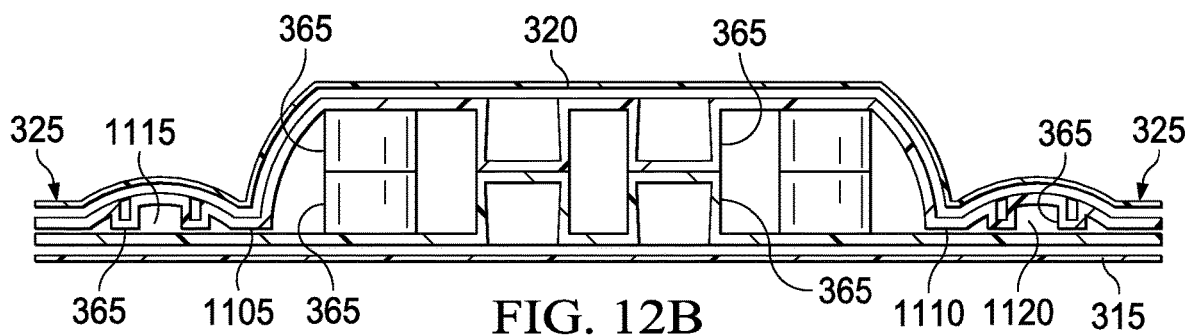
FIG. 12B is a schematic view taken along line 12B-12B of FIG. 12A.
Figure 12C:
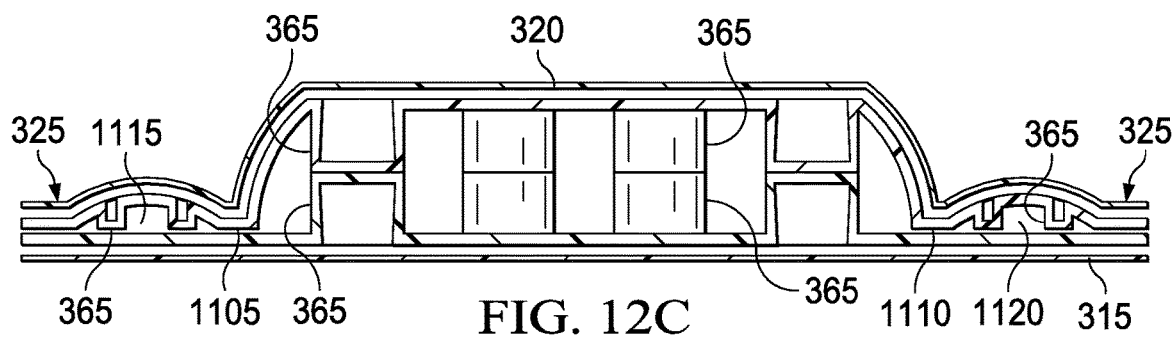
FIG. 12C is a schematic view taken along line 12C-12C of FIG. 12A.

FIG. 12A is a schematic view of an example configuration of fluid pathways in the bridge 160 of FIG. 10 as assembled, illustrating additional details that may be associated with some embodiments. FIG. 12B is a schematic view taken along line 12B-12B, and FIG. 12C is a schematic view taken along line 12C-12C. The supports 365 may have a variety of shapes, and may be sized and arranged in different patterns within the third fluid conductor 1125. For example, as illustrated in the examples of FIG. 12B and FIG. 12C, some of the supports 365 may extend from the first layer 315 and some of the supports 365 may extend from the second layer 320. In some embodiments, some of the supports 365 may be opposingly aligned. For example, at least some of the supports 365 can extend from the first layer 315 towards some of the supports 365 extending from the second layer 320, and some of the supports 365 in opposition may contact each other. In some embodiments, the bridge 160 may include more than one row of the supports 365. In the example of FIG. 12A, the bridge 160 has four rows of the supports 365, and the supports 365 forming outside rows are offset or staggered from the supports 365 forming the two inside rows. Each of the first barrier 1105 and the second barrier 1110 cooperate with the flange 325 to form the first fluid conductor 1115 and the second fluid conductor 1120. In some embodiments, some of the supports 365 may be disposed within one or both of the first fluid conductor 1115 and the second fluid conductor 1120.

The supports 365 disposed in the third fluid conductor 1125 may have a larger diameter and pitch than the supports 365 in the first fluid conductor 1115 and the second fluid conductor 1120, and may increase fluid flow to facilitate the removal of fluids and exudates within the recessed space 360. The supports 365 in the first fluid conductor 1115 and the second fluid conductor 1120 may have a noticeably smaller diameter and pitch than the supports 365 in the third fluid conductor 1125, and may restrict fluid flow to facilitate pressure sensing within the recessed space 360 while impeding the inflow of fluids and exudates into the first fluid conductor 1115 and the second fluid conductor 1120. The arrangement and dimensions of the supports 365 may be tailored to manage the delivery of negative pressure to the tissue interface 120 and the measurement of pressure within the recessed space 360.

Figure 13A:
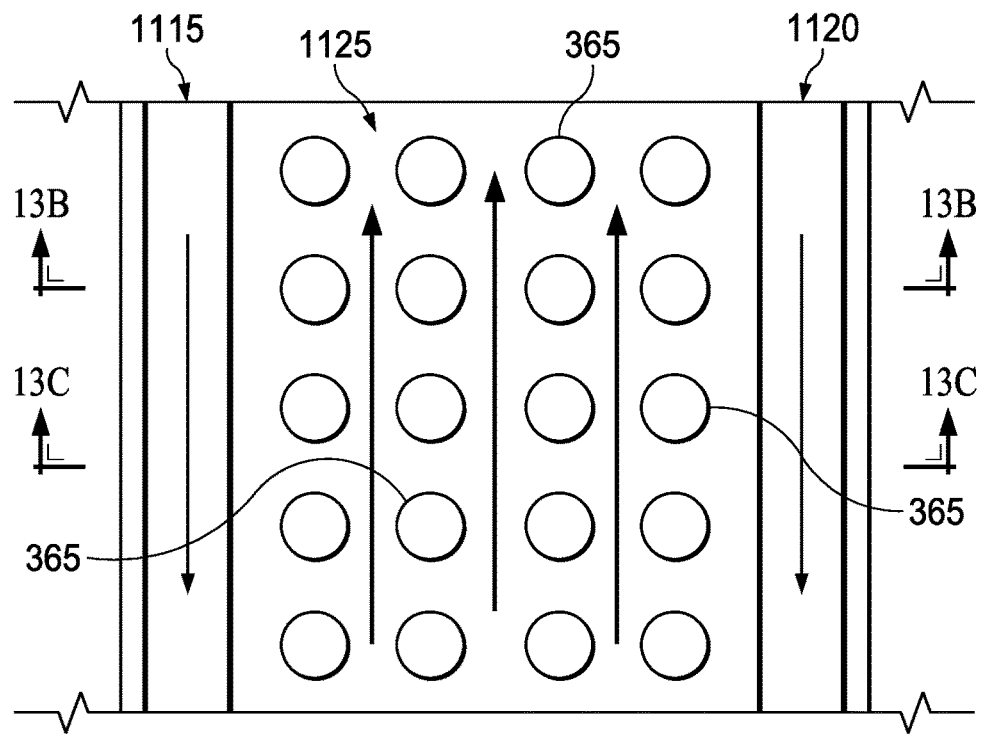
FIG. 13A is a schematic view of another example configuration of fluid pathways in the bridge of FIG. 10 as assembled, illustrating additional details that may be associated with some embodiments.
Figure 13B:
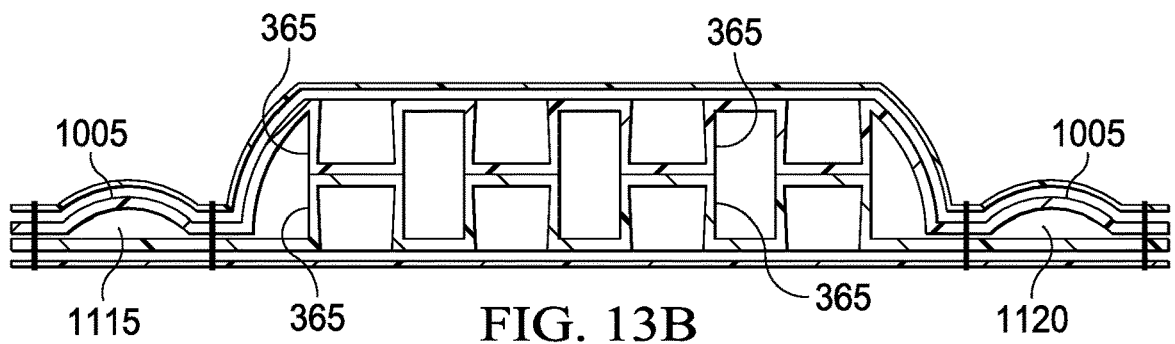
FIG. 13B is a schematic view taken along line 13B-13B of FIG. 13A.
Figure 13C:
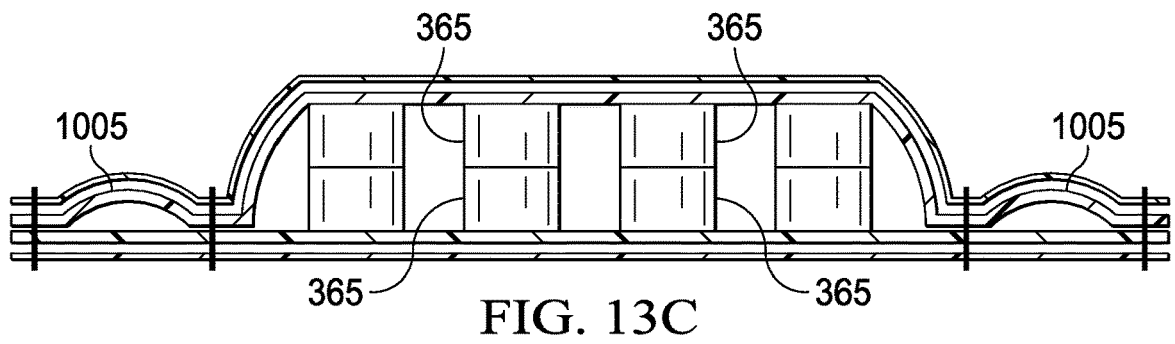
FIG. 13C is a schematic view taken along line 13C-13C of FIG. 13A.

FIG. 13A is a schematic view of another example configuration of fluid pathways in the bridge 160 of FIG. 10 as assembled, illustrating additional details that may be associated with some embodiments. FIG. 13B is a schematic view taken along line 13B-13B, and FIG. 13C is a schematic view taken along line 13C-13C. The example of FIG. 13A includes four rows of the supports 365, which are aligned both horizontally and vertically rather than being offset or staggered with each other. In some embodiments, the first fluid conductor 1115 and the second fluid conductor 1120 may be opened and supported by increasing the thickness of the first spacer layer 1005.

FIG. 14A is a plan view of another example of the bridge 160 having a low-profile structure that may be associated with some example embodiments of the therapy system 100. The bridge 160 in FIG. 14A may be configured to provide negative-pressure therapy to a plurality of tissue sites using only a single negative-pressure source. In the embodiment shown in FIG. 14A, the bridge 160 may be similar to that shown in FIG. 10, but may have at least two distal ends 1405 for simultaneous fluid communication with the plurality of tissue sites, along with a port 1410 for introduction of negative pressure (e.g. via fluid communication with a negative-pressure source). The port 1410 may be configured to fluidly couple to the negative-pressure source. As shown in FIG. 14A, some embodiments may have a single port 1410, which may allow a single negative-pressure source to provide negative-pressure therapy to multiple tissue sites. The bridge 160 may have a plurality of distal ends 1405, in some embodiments. The distal ends 1405 may be in fluid communication with a central portion 1415, forming a continuous fluid pathway. In some embodiments, the port 1410 maybe located in the central portion 1415 of the fluid pathway. In some embodiments, the central portion 1415 may be located between at least two distal ends 1405. For example, the central portion 1415 may be located halfway between two distal ends 1405. In some embodiments, the fluid pathway may be configured so that fluid may flow from each distal end towards the port (e.g. when negative pressure is applied to the port). In some embodiments, the fluid pathway may extend longitudinally from the distal ends 1405 to the central portion 1415. In FIG. 14A, there are two distal ends 1405, and the fluid pathway extends longitudinally between the two distal ends 1405 (e.g. with the central portion 1415 between the distal ends 1405). In some embodiments, one or more distal end 1405 may comprise an applicator 240. For example, each distal end may comprise an applicator 240 as in FIG. 14A.

As shown in FIG. 14A, the fluid pathway may be supported as an open pathway by the plurality of supports 365. In some embodiments, the plurality of supports 365 may be configured to support the fluid pathway substantially along its entire length and/or width. For example, the supports 365 may be co-extensive with the fluid pathway. In some embodiments, the plurality of supports 365 may be arranged in rows, and the rows may be aligned and may extend longitudinally. For example, the rows may extend the length of the bridge 160, with longitudinally extending spaces of the fluid pathway separating the rows. The row configuration of supports 365 may allow fluid flow longitudinally from one end of the fluid pathway to the other, for example when the bridge 160 is under compression. For example, in the row configuration of supports 365, the longitudinally extending spaces may provide unobstructed flow channels of the fluid pathway between the rows of supports 365.

FIG. 14B is a schematic longitudinal cross-section view of the bridge 160 of FIG. 14A, illustrating additional details that may be associated with some embodiments. FIG. 14B illustrates the plurality of supports 365 of the bridge 160, which may comprise a first plurality of supports 1420 and a second plurality of supports 1425. In some embodiments, the first plurality of support 1420 may be opposingly aligned with the second plurality of supports 1425, for example stacked to jointly support the fluid pathway. In some embodiments, the first plurality of supports 1420 and the second plurality of supports 1425 may jointly support the fluid pathway to maintain an open pathway with a height substantially equal to the height of one of the first plurality of supports 1420 and one of the second plurality of supports 1425 taken together (e.g. stacked to provide a cumulative height). The first plurality of supports 1420 and the second plurality of supports 1425 may each be aligned into longitudinally extending rows. For example, the first plurality of supports 1420 may be aligned into rows that match the rows of the second plurality of supports 1425, so that the first plurality of supports 1420 may be opposingly aligned and stacked with the second plurality of supports 1425.

In some embodiments, the bridge 160 may be configured with a low profile. For example, the bridge 160 may have a height (H) of approximately 5 millimeters. Some embodiments may have a height of less than approximately 5 millimeters, less than 6 millimeters, less than 7 millimeters or from about 5-7 millimeters. Some embodiments of the bridge 160 may have a length from approximately 200 millimeters to 500 millimeters.

In some embodiments, the plurality of supports 365 (e.g. the first plurality of supports 1420 and the second plurality of supports 1425 in FIG. 14B) may be located within the envelope 1430. The envelope 1430 may encompass the plurality of supports 365 to define the internal fluid pathway between the distal ends 1405 (e.g. an enclosed conduit). In some embodiments, the bridge 160 may be a unitary whole, pre-formed element with the plurality of supports 365 in the envelope 1430. The bridge 160 may be ready to be applied to tissue sites without the need for customization and/or in-situ construction. The envelope 1430 may be made of a material that is impermeable to liquid and/or is substantially air-tight (e.g. allowing a vacuum to be drawn through the envelope 1430). In some embodiments, the envelope 1430 may comprise at least one vapor-transfer surface that is permeable to vapor. In some embodiments, the supports 365 may structurally support the envelope 1430 to define the internal fluid pathway. The fluid pathway may fluidly couple the distal ends 1405. For example, the distal ends 1405 may be in fluid communication with the central portion 1415 to form the continuous fluid pathway. The fluid pathway may fluidly couple the apertures 355 in the distal ends 1405 to the port 1410.

The envelope 1430 may comprise a first surface 1435 (e.g. outward-facing when the bridge 160 is in place on a tissue site) and a second surface 1440 (e.g. patient-facing). The supports 365 may be disposed between the first surface 1435 and the second surface 1440 to form the fluid pathway between the distal ends 1405. In some embodiments, the envelope 1430 may comprise a first layer and a second layer, which may be coupled together about a perimeter to form an enclosed conduit or space of the fluid pathway. For example, the first layer may form the first surface 1435 of the envelope 1430, while the second layer may form the second surface 1440 of the envelope 1430. The envelope 1430 may comprise the plurality of apertures 355 and the port 1410. For example, each distal end 1405 of the envelope 1430 of FIG. 14B may comprise one of the plurality of apertures 355. The apertures 355 may be configured to interact with the tissue sites. Typically, all apertures 355 may be located on the same surface of the envelope 1430. For example, in FIG. 14B the apertures 355 may be located on the second surface 1440 of the envelope 1430. In some embodiments, the apertures 355 may only be located in the distal ends 1405 of the bridge 160. The port 1410 in FIG. 14B may be located on the first surface 1435 of the envelope 1430.

In FIG. 14B, each distal end 1405 may comprise a recessed space 360 within the fluid pathway. In some embodiments, the recessed spaces 360 may be configured to fluidly communicate with the ambient environment through the apertures 355 in the second surface 1440. In some embodiments, each recessed space 360 may be aligned with the corresponding aperture 355 in each distal end 1405 (e.g. with a common central axis). In FIG. 14B, each recessed space 360 may extend inward from the second surface 1440. Similarly, the fluid pathway may also comprise a port recessed space 1445 configured to fluidly communicate with the negative-pressure source through the port 1410. In some embodiments, the port recessed space 1445 may be configured to align with the port 1410. In FIG. 14B, the port recessed space 1445 may be located in the central portion 1415 of the fluid pathway, and may extend inward from the first surface 1435 of the envelope 1430.

In some embodiments, the fluid pathway may be pneumatically isolated from the ambient environment except through the recessed spaces 360 and/or the apertures 355 in the distal ends 1405 of the bridge 160. In some embodiments, the apertures 355 may be configured to allow fluid communication between the recessed spaces 360 and the ambient environment. In some embodiments, the fluid pathway may be in fluid communication with the ambient environment through the apertures 355.

In some embodiments, each of the supports 365 may comprise a hollow standoff 380, which may be sealed to maintain internal pressure within the plurality of hollow standoffs 380. In some embodiments, each of the plurality of supports 365 may comprise a standoff 380 and a base, with the standoff having a closed surface extending away from the base. The supports 365 may comprise a variety of shapes, for example substantially circular, hexagonal, oval, triangular, and/or square. In some embodiments, the standoffs 380 may each comprise a blister, a bubble, or a cell. In some embodiments, all of the standoffs 380 may be similarly sized and/or shaped. In some embodiments, the supports 365 may comprise a diameter from approximately two to four millimeters and/or a height from approximately two to five millimeters.

Some embodiments of the fluid pathway may be similar to the third pathway 350 of FIG. 3A and/or the third fluid conductor 1125 of FIG. 11A, while also having an aperture 355 in two or more distal ends 1405. In some embodiments, the fluid pathway may be configured to maintain an open pathway despite application of negative pressure and/or external compression loading. In some embodiments, the plurality of supports 365 are configured to maintain the fluid pathway as an open pathway, for example allowing negative pressure to be applied to a tissue site through the fluid pathway even when the fluid pathway experiences compressive loads. For example, the fluid pathway may be maintained in an open position, without collapsing in a way that may close off the fluid pathway, even if the patient is lying atop the bridge 160. In some embodiments, the plurality of supports 365 may be configured to support the fluid pathway substantially along its entire length and/or width. For example, the supports 365 may be co-extensive with the fluid pathway. In some embodiments, the supports 365 may be sealed to maintain an internal pressure. For example, the supports 365 may be maintained at a pressure at or above atmospheric pressure, which may aid in resisting compression or collapse.

In some embodiments, the fluid pathway may comprise at least one one-way valve 1450 configured to prevent reflux and/or transmission of fluid from one tissue site to another tissue site. For example, the one-way valves 1450 may be located in the fluid pathway between the port 1410 and one of the apertures 355, and may be configured to allow fluid flow from the aperture 355 towards the port 1410. In some embodiments, each distal end 1405 may comprise a one-way valve 1450. The one-way valves 1450 may be configured to allow fluid (e.g. exudate) flow inward from the apertures 355 towards the port 1410, while preventing fluid flow the opposite direction (e.g. preventing fluid flow outward from the port 1410 and/or from other distal ends). In FIG. 14B, a one-way valve may 1450 be located in proximity to each aperture 355. For example, a one-way valve 1450 may be located over each aperture 355, in the fluid pathway, and/or between each aperture 355 and the corresponding recessed space 360 in the distal end 1405. In some embodiments, the one-way valves 1450 may only be located in distal ends 1405. The one-way valves 1450 may open in response to negative pressure in the fluid pathway (e.g. when negative pressure is applied to the port 1410), allowing fluid flow from the tissue site into the fluid pathway of the bridge 160. The valves 1450 may thus prevent cross-contamination between multiple tissue sites and/or prevent fluid from flowing between tissue sites.

FIG. 14C is a schematic view of an exemplary one-way valve 1450 from FIG. 14B, illustrating additional details that may be associated with some embodiments. FIG. 14C illustrates an open one-way valve 1450, which may be a flap valve in some embodiments. When negative pressure is applied to the bridge 160, the valves 1450 may open and fluid/exudate may be removed from the tissues sites through the apertures and corresponding open valves 1450.

FIG. 14D is another schematic view of the exemplary valve 1450 from FIG. 14C, illustrating additional details that may be associated with some embodiments. FIG. 14D illustrates a closed one-way valve 1450. When there is no (or insufficient) negative-pressure in the fluid pathway, the valves 1450 may close (or remain closed) and fluid/exudate in the fluid pathway (e.g. already removed from the tissue sites during negative-pressure therapy) cannot flow back into the tissue sites.

Figure 14E:
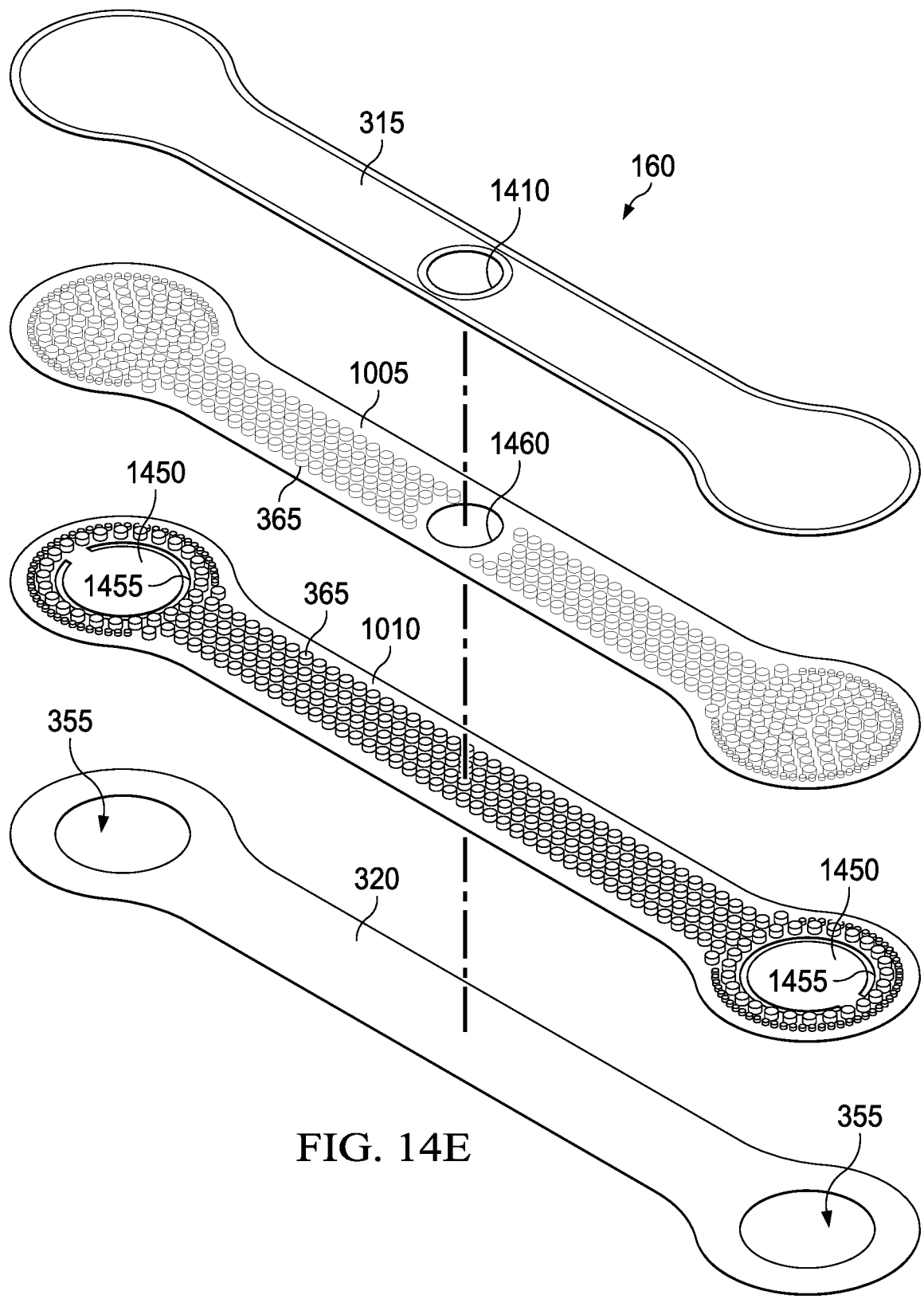
FIG. 14E is an exploded or assembly view of the bridge of FIG. 14A, illustrating exemplary layers.

FIG. 14E is an exploded or assembly view of the bridge 160 of FIG. 14A, illustrating additional details that may be associated with some embodiments. The bridge 160 in FIG. 14E may comprise the first layer 315, the first spacer layer 1005, the second spacer layer 1010, and the second layer 320. In FIG. 14E, the supports 365 of the first spacer layer 1005 and the supports 365 of the second spacer layer 1010 may extend inward towards each other. The first layer 315 may be adjacent to and in stacked relationship with the first spacer layer 1005, opposite the second spacer layer 1010. The second layer 320 may be adjacent to and in stacked relationship with the second spacer layer 1010, opposite the first spacer layer 1005. The first layer 315 and the second layer 320 may be sealed together about the perimeter, forming the enclosed fluid pathway supported by the first spacer layer 1005 and the second spacer layer 1010. In some embodiments, the first spacer layer 1005 may comprise the first plurality of supports, and the second spacer layer 1010 may comprise the second plurality of supports. For example, the first plurality of supports may extend inward from an inner surface of the first spacer layer 1005, and the second plurality of supports may extend inward from an inner surface of the second spacer layer 1010. In some embodiments, the first spacer layer 1005 and second spacer layer 1010 may be stacked. For example, the first plurality of supports of the first spacer layer 1005 may be stacked with the second plurality of supports of the second spacer layer 1010, with supporting faces substantially parallel and/or contacting. In the embodiment of FIG. 14E, there is no foam within the envelope. For example, the means of support may not comprise foam in some embodiments, but may rather comprise the plurality of thermoformed supports 365.

In some embodiments, each of the first plurality of supports of the first spacer layer 1005 may comprise a hollow standoff, and the first layer 315 may be sealed to the first spacer layer 1005 to maintain internal pressure within the plurality of hollow standoffs. Similarly, each of the second plurality of supports of the second spacer layer 1010 may comprise a hollow standoff, and the second layer 320 may be sealed to the second spacer layer 1010 to maintain internal pressure within the standoffs of the second plurality of supports. In some embodiments, the first layer 315 and/or the second layer 320 may comprise a polyurethane film from approximately 80 to 120 micron in thickness. In some embodiments, the first spacer layer 1005 and/or the second spacer layer 1010 may be thermoformed structures with integral open pathway features, such as supports 365. In some embodiments, the thermoformed structures may comprise thermoplastic polyurethane, for example thermoplastic polyurethane film from approximately 200 to 500 microns in thickness.

In FIG. 14E, the second layer 320 may comprise the apertures 355 in each distal end 1405 configured to allow fluid communication between the fluid pathway and the ambient environment. The apertures 355 may be located in at least two distal ends of the bridge 160, and in FIG. 14E the apertures 355 may be located in both (e.g. all) distal ends. In some embodiments, the first layer 315 may comprise the port 1410. For example, the port 1410 may be located in a central portion of the first layer 315, between the distal ends. Some embodiments may also comprise openings 1455 located in the second spacer layer 1010 which may be concentric with the apertures 355 of the second layer 320. For example, openings 1455 may be located in at least two distal ends of the second spacer layer 1010. The openings 1455 may allow fluid flow through the second spacer layer 1010. The openings 1455 do not comprise any supports in those open portions of the second spacer layer 1010. In some embodiments, one of the openings 1455 may be located in each distal end of the second spacer layer 1010. In some embodiments, each aperture 355 may have a corresponding opening 1455. In some embodiments, the openings 1455 may be aligned with the apertures 355. For example, the openings 1455 may each be concentric with (e.g. with a common central axis) one of the apertures 355. The openings 1455 in the second spacer layer 1010 may form the recessed spaces (e.g. the recessed spaces may each comprise one of the openings 1455). Some embodiments may also comprise the one-way valves 1450, with one of the plurality of one-way valves 1450 for each opening 1455. In some embodiments, the one-way valves 1450 may be integral to the second spacer layer 1010. For example, a portion of the second spacer layer 1010 may be cut to form the openings 1455 with a flap valve 1450 for each opening 1455. Alternatively, a one-way valve 1450 may be attached spanning each opening 1455 in the second spacer layer 1010.

Some embodiments may comprise an opening 1460 in the first spacer layer 1005 which may be aligned (e.g. concentric with) the port 1410 of the first layer 315. In some embodiments, the opening 1460 may be located in the central portion of the first spacer layer 1005. The opening 1460 may allow fluid flow through the first spacer layer 1005. The opening 1460 does not comprise any supports in that open portion of the first spacer layer 1005. The opening 1460 may form the port recessed space (e.g. the port recessed space may comprise the opening 1460). In some embodiments, the first layer 315 and the second layer 320 may be coupled to form the envelope with the enclosed space of the fluid pathway between the first layer 315 and the second layer 320. In some embodiments, the first layer 315 and the second layer 320 may each be formed of a film. Other embodiments may form the fluid pathway as an open pathway using only a single spacer layer. Other embodiments may form the fluid pathway by sealing the first spacer layer 1005 to the second spacer layer 1010 about the perimeter, for example without the need for any exterior film layers (e.g. with the envelope formed by sealing the spacer layers together about their perimeter, without the need for any additional outer layers). Other embodiments may form the fluid pathway between the first layer 315 and the second layer 320, while having the plurality of supports located therebetween without any spacer layer. For example, longitudinal tubular supports might be located between the first layer 315 and the second layer 320 in some alternate embodiments.

During negative-pressure therapy, fluid may be removed through the longitudinally extending rows between the plurality of supports 365. This may be true whether or not external compression is applied to the bridge 160. During negative-pressure therapy in some embodiments, the first plurality of supports may be drawn towards the second plurality of supports, so that the supporting faces substantially contact. For example, some supporting faces of supports 365 may directly contact opposing support faces.

Figure 15:
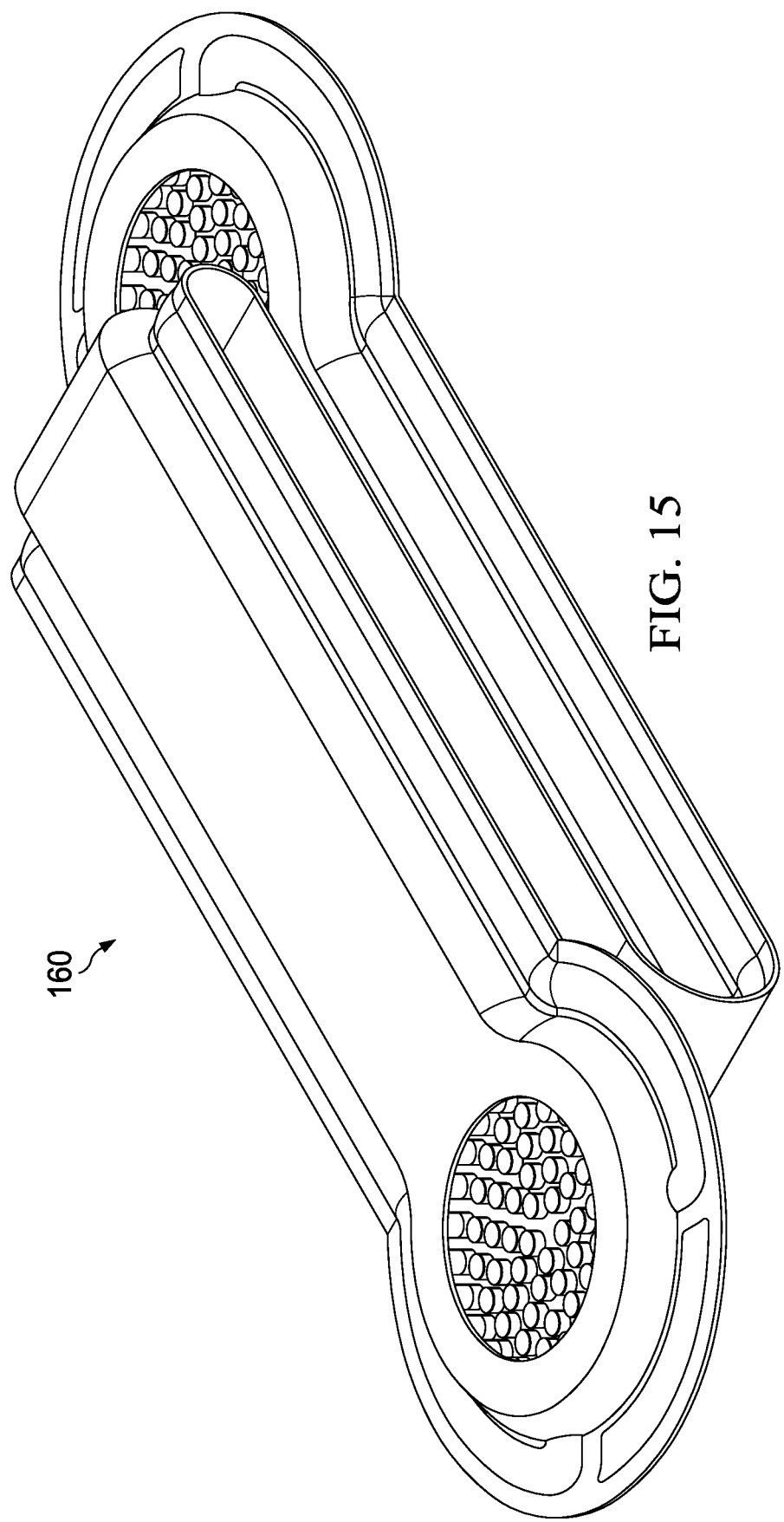
FIG. 15 is an isometric view of the bridge of FIG. 14A folded.

FIG. 15 is an isometric view of the bridge 160 of FIG. 14A when folded, illustrating additional details associated with some embodiments. The fluid bridge 160 may be configured to allow folding, for example with the bridge 160 being sufficiently flexible to allow folding. In some embodiments, the bridge 160 may also be configured so that, when folded, the fluid pathway remains open for negative-pressure therapy. For example, folding the bridge 160 may not substantially restrict fluid flow therethrough. In some embodiments, the plurality of supports may maintain sufficiently open fluid pathway to allow effective negative-pressure therapy. In some embodiments, the fluid bridge 160 (or a portion thereof) may be folded to adjust the distal ends based on the relative locations of the plurality of tissue sites to be treated. For example, the bridge 160 (or portions thereof) may be folded to adjust the length of the bridge 160 between distal ends and/or the angular location of the distal ends. In some embodiments, the folds may comprise accordion folds.

Figure 16:
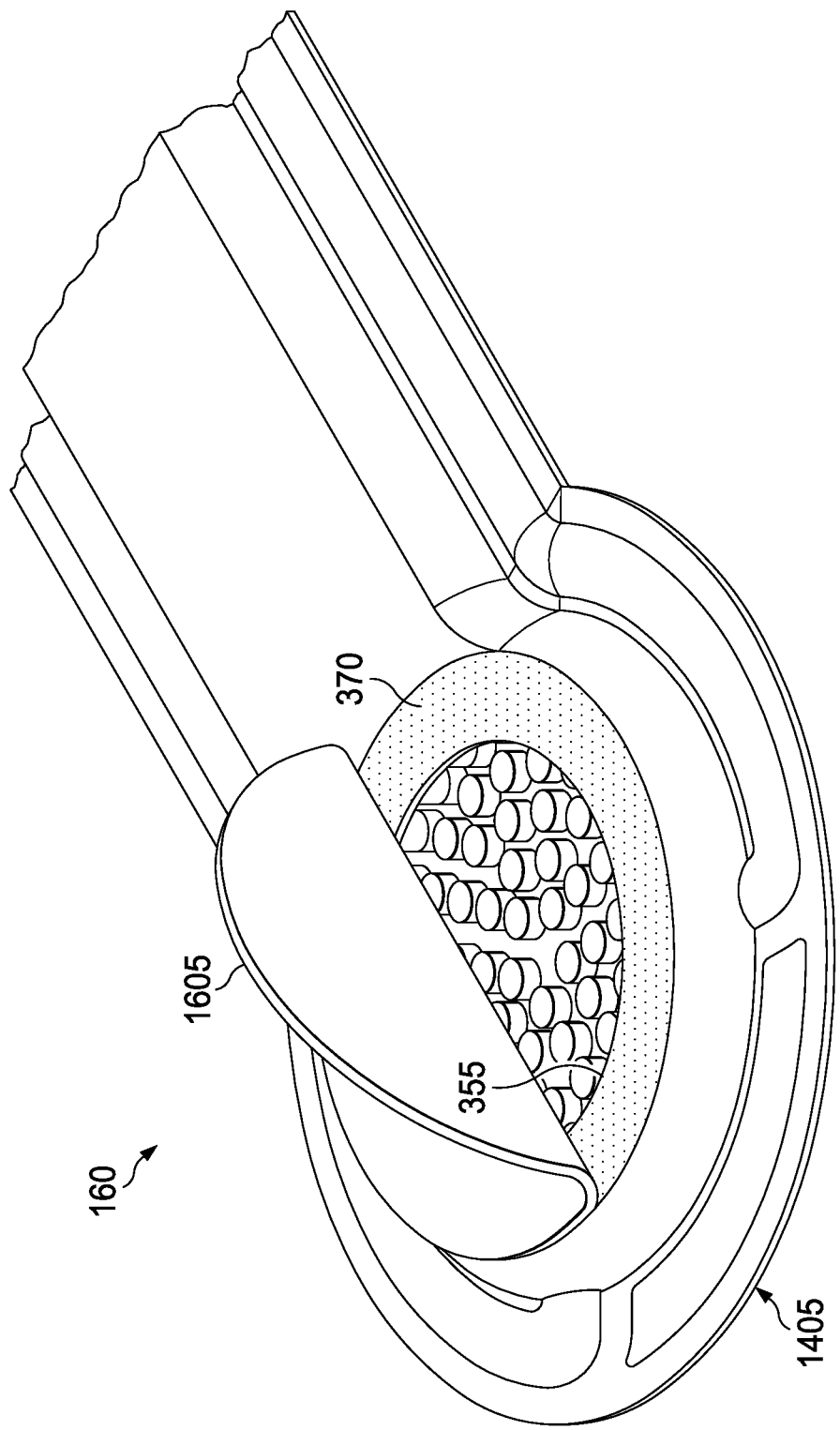
FIG. 16 is an isometric view of an exemplary distal end of the bridge of FIG. 14A.

FIG. 16 is an isometric view of an exemplary distal end 1405 of the bridge 160 of FIG. 14A, illustrating additional details associated with some embodiments. In FIG. 16, an adhesive may be located on the second surface in proximity to the apertures 355. For example, a ring of adhesive may be located about each aperture 355, forming the affixation surface 370 on the distal ends 1405. In some embodiments, the adhesive may be one or more of the following: a medically acceptable, pressure-sensitive adhesive, a paste, a hydrocolloid, and a hydrogel. In some embodiments, a release liner 1605 may be located adjacent to the second surface, for example with the adhesive ring located between the second surface and the release liner 1605. The release liner 1605 may cover the affixation surface 370 prior to application of the distal end 1405 to a tissue site, and may be configured to be removed in order to expose the adhesive. In some embodiments, a plurality of release liners 1605 may removably or releasably cover each aperture 355. In some embodiments, one of the release liners 1605 may cover the port. In some embodiments, the release liners 1605 may form a seal (e.g. on the exterior surface of the envelope, for example temporarily sealing the apertures and/or the port).

In some embodiments, the envelope may optionally comprise a perforation forming a calibrated flow. For example, each distal end may comprise a calibrated flow in the first surface. The calibrated flow may help induce airflow to assist in preventing blockages and/or may assist with pressure sensing to identify potential blockages. In some embodiments, each of the calibrated flows may be less than about 5 cc/min located in proximity to each of the distal ends. In some embodiments, the envelope may further comprise a bacterial filter over each calibrated flow, which may prevent ingress of contaminants.

In some embodiments, the bridge may optionally further comprise a plurality of regulators in the fluid pathway configured to step-down pressure. For example, a regulator may be positioned between each distal end and the central portion and/or port. The plurality of regulators may be configured to ensure that there is a pressure gradient between the port and the distal ends. For example, if the port is located in the central portion of the fluid pathway, the central portion may experience more negative-pressure than the distal ends. In some embodiments, the central portion may experience 125 mmHg negative pressure, while the distal ends experience 100 mmHg negative pressure.

Some embodiments of the bridge may optionally have one or more pressure sensing pathways that each extends from an aperture to the port. The one or more pressure sensing pathways may each be pneumatically isolated from the fluid pathway, except at the distal ends. For example, a barrier may extend between the inner surface of the first layer and the inner surface of the second layer to form each pressure sensing pathway within the enclosed space of the envelope. The barrier may pneumatically isolate the pressure sensing pathway from the fluid pathway except through the recessed space in the distal end. In some embodiments, the pressure sensing pathway may be similar to the first pathway 340 or the second pathway 345 in FIG. 3A or the first fluid conductor 1115 or second fluid conductor 1120 in FIG. 11A. In some embodiments, the port may further be configured to fluidly couple the pressure sensing pathway to a pressure sensor.

Figure 17:
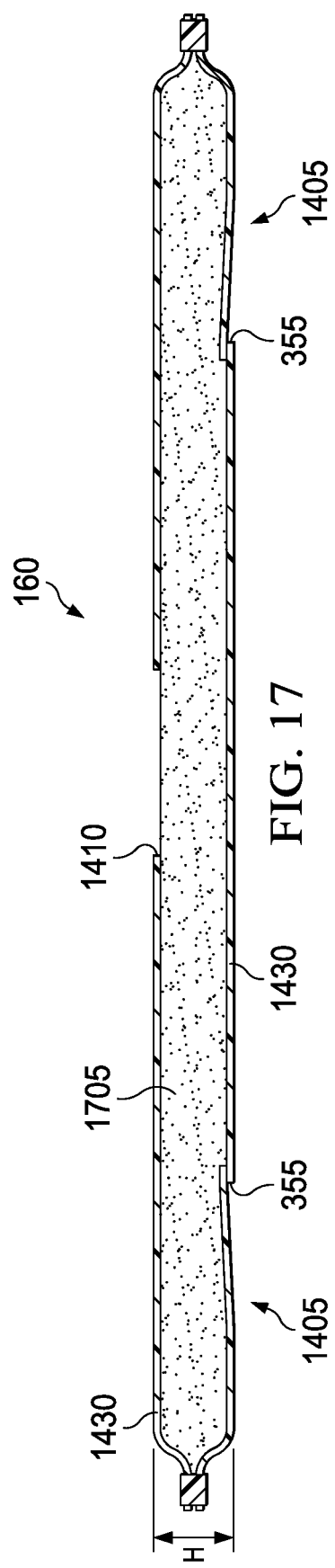
FIG. 17 is a longitudinal cross-section view of another exemplary bridge embodiment.

FIG. 17 is a longitudinal cross-section view of an alternate bridge 160 embodiment, similar to that of FIG. 14A but having the means of support (e.g. support layer) comprise a delivery manifold 1705. While FIG. 17 illustrates the use of foam delivery manifold 1705 as the support layer within the envelope 1430 for a bridge 160 configured similarly to that in FIG. 14A, any disclosed bridge 160 embodiments herein may use a delivery manifold 1705 as the support layer (e.g. substituting the delivery manifold 1705 in place of the plurality of supports). In some embodiments, the delivery manifold 1705 may structurally support the envelope 1430. For example, the delivery manifold 1705 may be configured to maintain an open fluid pathway within the envelope 1430 by maintaining space within the envelope 1430 and/or preventing complete collapse of the envelope 1430. In some embodiments, the delivery manifold 1705 may extend substantially the entire length and/or width of the envelope 1430, for example substantially filling the fluid pathway defined by the interior enclosed space of the envelope 1430. In some embodiments, the delivery manifold 1705 may provide effective manifolding that distributes or collects fluid and/or negative pressure within the fluid bridge 160. For example, the delivery manifold 1705 may receive negative pressure from the port 1410 and distribute negative pressure through multiple apertures 355 in the distal ends 1405 of the bridge 160, which may have the effect of drawing fluid from the plurality of distal ends 1405 towards the port 1410.

The delivery manifold 1705 may comprise any material capable of transferring negative pressure. For example, the delivery manifold 1705 may comprise materials open to pressure and fluid flow, particularly in the form of air and exudate. In some embodiments, the delivery manifold 1705 may comprise a foam material. For example, the delivery manifold 1705 may comprise open cell and/or reticulated foam, which may be polyurethane foam in some embodiments. In some embodiments, the foam of the delivery manifold may be hydrophobic. In some embodiments, the delivery manifold may comprise a GranuFoam® material from Kinetic Concepts, Inc. of San Antonio, Tex.

In some embodiments, the delivery manifold 1705 may comprise an open cell and/or reticulated foam having a density of about 2.6-8.0 lb/ft3, about 80-250 pores per inch, and/or pore size of about 80-300 micron. In some embodiments, the density of the foam of the delivery manifold 1705 may be about 3.9-4.8 lb/ft3. In some embodiments, the average pore size of the open cell foam of the delivery manifold 1705 may be about 133-200 micron. In some embodiments, the foam of the delivery manifold 1705 may have 120-150 pores per inch. For example, the foam of the delivery manifold 1705 may have 120-135 pores per inch. In some embodiments, the foam of the delivery manifold 1705 may have a 25% compression load deflection of at least 1.05 pounds per square inch and a 65% compression load deflection of at least 1.29 pounds per square inch. In some embodiments, the foam of the delivery manifold 1705 may have a 25% compression load deflection of at least 1.75 pounds per square inch and a 65% compression load deflection of at least 2.15 pounds per square inch. In some embodiments, the foam of the delivery manifold 1705 may have a 25% compression load deflection of about 1.05-1.75 pounds per square inch and a 65% compression load deflection of about 1.29-2.15 pounds per square inch.

In some embodiments, the foam of the delivery manifold 1705 may be formed by a felting process. The felted foam or felted foam layer may serve as a delivery manifold that may comprise interconnected pathways. Any suitable foam for felting may be used, including the example foams mentioned herein, such as GRANUFOAM™. A felted foam may undergo a thermoforming process to permanently compress the foam to increase the density of the foam. A felted foam may also be compared to other felted foams or compressed foams by comparing the firmness factor of the felted foam to the firmness factor of other compressed or uncompressed foams. A compressed or felted foam may have a firmness factor greater than 1. Felting is a thermoforming process that permanently compresses a material. For example, in order to create felted foam, such as felted polyurethane, the foam is heated to an optimum forming temperature during the polyurethane manufacturing process, and then it is compressed. The degree of compression controls the physical properties of the felted foam. For example, felted foam has an increased effective density and felting can affect fluid-to-foam interactions. For example, as the density increases, compressibility or collapse decreases. Therefore, foams which have different compressibility or collapse have different firmness values. The firmness of a felted foam is the felting ratio: original thickness/final thickness. In some example embodiments, a felted delivery manifold "firmness" value or degree or factor can range from about 2 to about 5, preferably about 3 to about 5. There is a general linear relationship between firmness level, density, pore size (or pores per inch) and compressibility under negative pressure. For example, foam found in a GRANUFOAM™ dressing that is felted to firmness 3 will not only show a three-fold density increase, but will only compress to about a third of its non-felted form. In some embodiments, the pre-felted foam for the delivery manifold 1705 may have 40-50 pores per inch, a density of 1.3-1.6 lb/ft3, an average pore size in a range of 400-600 micron, a 25% compression load deflection of at least 0.35 pounds per square inch, and/or a 65% compression load deflection of at least 0.43 pounds per square inch. In some embodiments, the pre-felted foam may have a thickness greater than 10 mm, for example 10-35 mm, 10-25 mm, 10-20 mm, or 15-20 mm. In some embodiments, the pre-felted foam may be felted to provide denser foam for the delivery manifold 1705. For example, the pre-felted foam may be felted to a felted firmness factor of 2-5. In some embodiments, the foam may be felted to a felted firmness factor of 3-5. Some embodiments may felt the foam to a felted firmness factor of 3.

Figure 18:
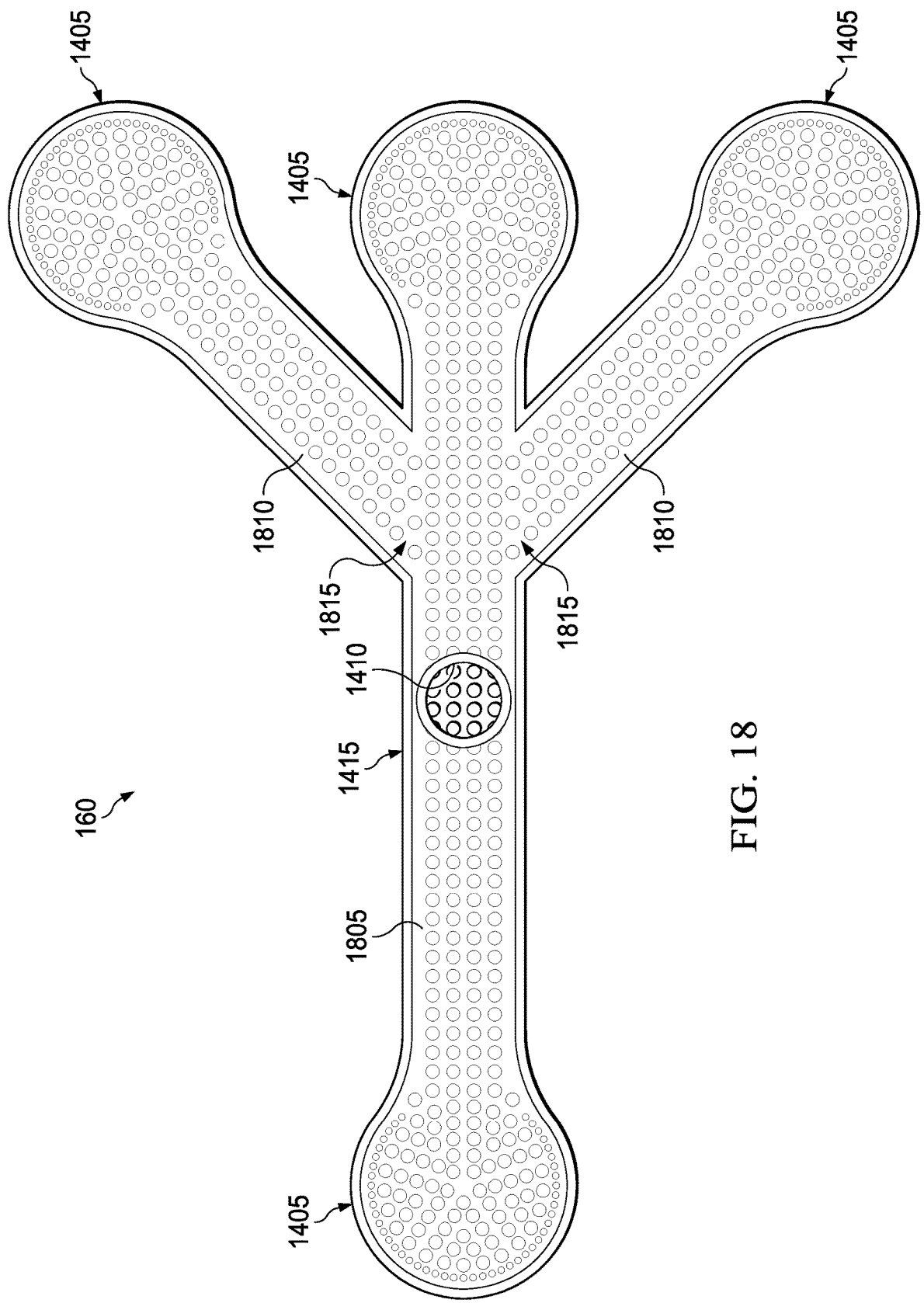
FIG. 18 is a plan view of another example of a bridge that may be associated with some example embodiments of the therapy system of FIG. 1, comprising more than two distal ends.

FIG. 18 is a plan view of another example of a bridge 160 that may be associated with some example embodiments of the therapy system of FIG. 1, comprising more than two distal ends 1405. The bridge 160 of FIG. 18 may be similar to that of FIG. 14A, but comprises four distal ends 1405. The fluid pathway may comprise a primary fluid pathway 1805, along with one or more branch fluid pathways 1810. In FIG. 18, the primary fluid pathway 1805 may comprise two distal ends 1405, and each branch fluid pathway 1810 may comprise one distal end 1405 and one proximal end 1815. The proximal end 1815 of each branch fluid pathway 1810 may be fluidly coupled to the primary fluid pathway 1805, thereby forming a continuous fluid pathway between the distal ends 1405. In FIG. 18, the port 1410 is located on the central portion 1415, which may be located in the primary fluid pathway 1805 between the two distal ends 1405 of the primary fluid pathway 1805. The port 1410 may be located on the first surface (e.g. not on the same surface as the apertures).

Figure 19:
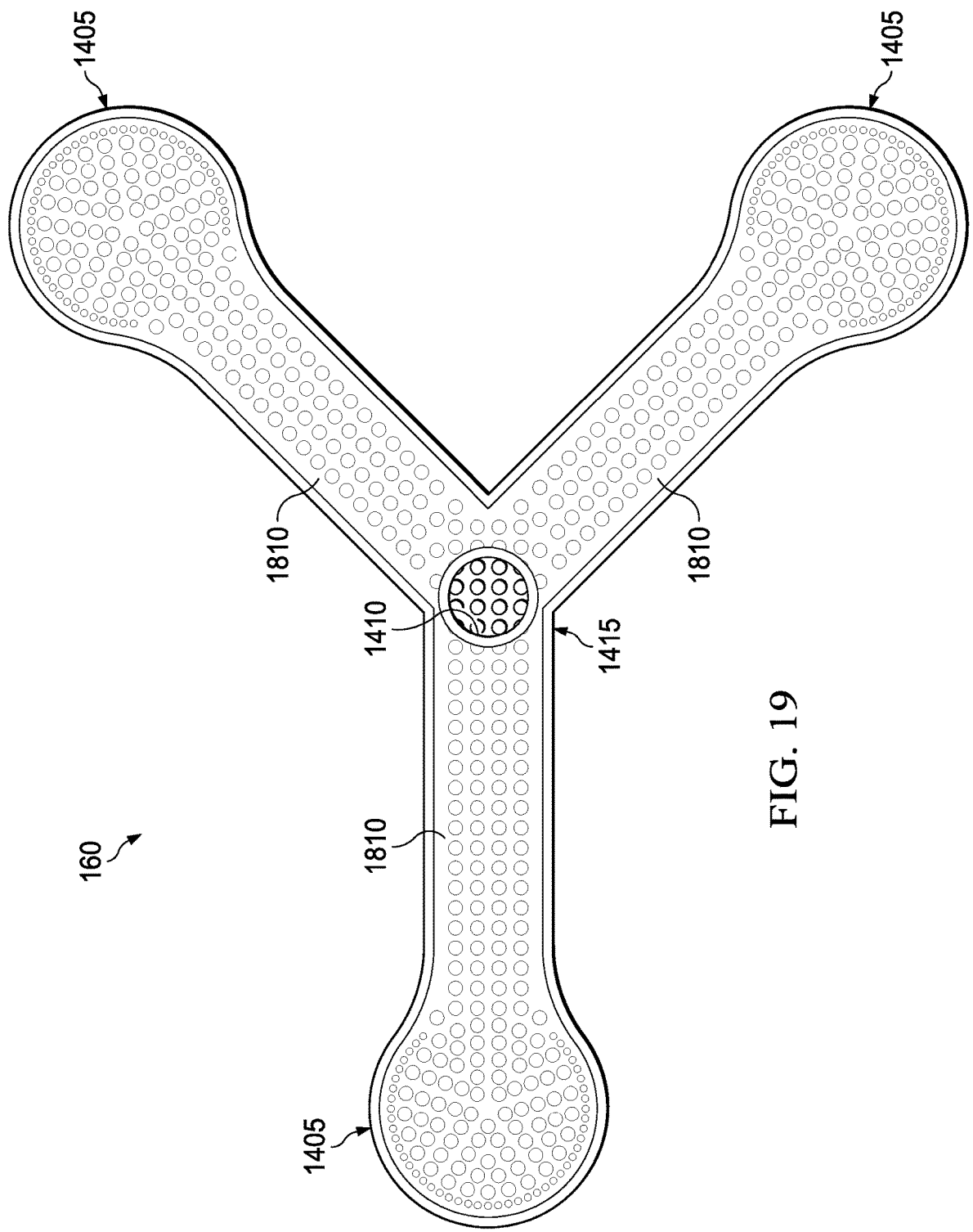
FIG. 19 is a plan view of another example of a bridge with a plurality of distal ends that may be associated with some example embodiments of the therapy system of FIG. 1.

FIG. 19 is a plan view of another example of a bridge 160 with a plurality of distal ends 1405 that may be associated with some example embodiments of the therapy system of FIG. 1, illustrating additional details associated with some embodiments. The bridge 160 of FIG. 19 may be similar to that of FIG. 18, but comprises three distal ends 1405. FIG. 19 comprises three branch fluid pathways 1810, each with a distal end 1405 and a proximal end 1815. The proximal ends 1815 of each of the three branch fluid pathways 1810 may be fluidly coupled to form a continuous fluid pathway. Stated another way, any one of the branches could be considered the primary fluid pathway (albeit with only one distal end and one proximal end), and the other branch fluid pathways may fluidly couple to it. In FIG. 19, each of the branch fluid pathways 1810 may be approximately equal in length. The port 1410 of FIG. 19 may be located in the central portion 1415 of the fluid pathway and/or may be located on the first surface. In some embodiments, the distal end apertures (not shown here, but located on the second surface) may all be equidistant from the port 1410.

Figure 20:
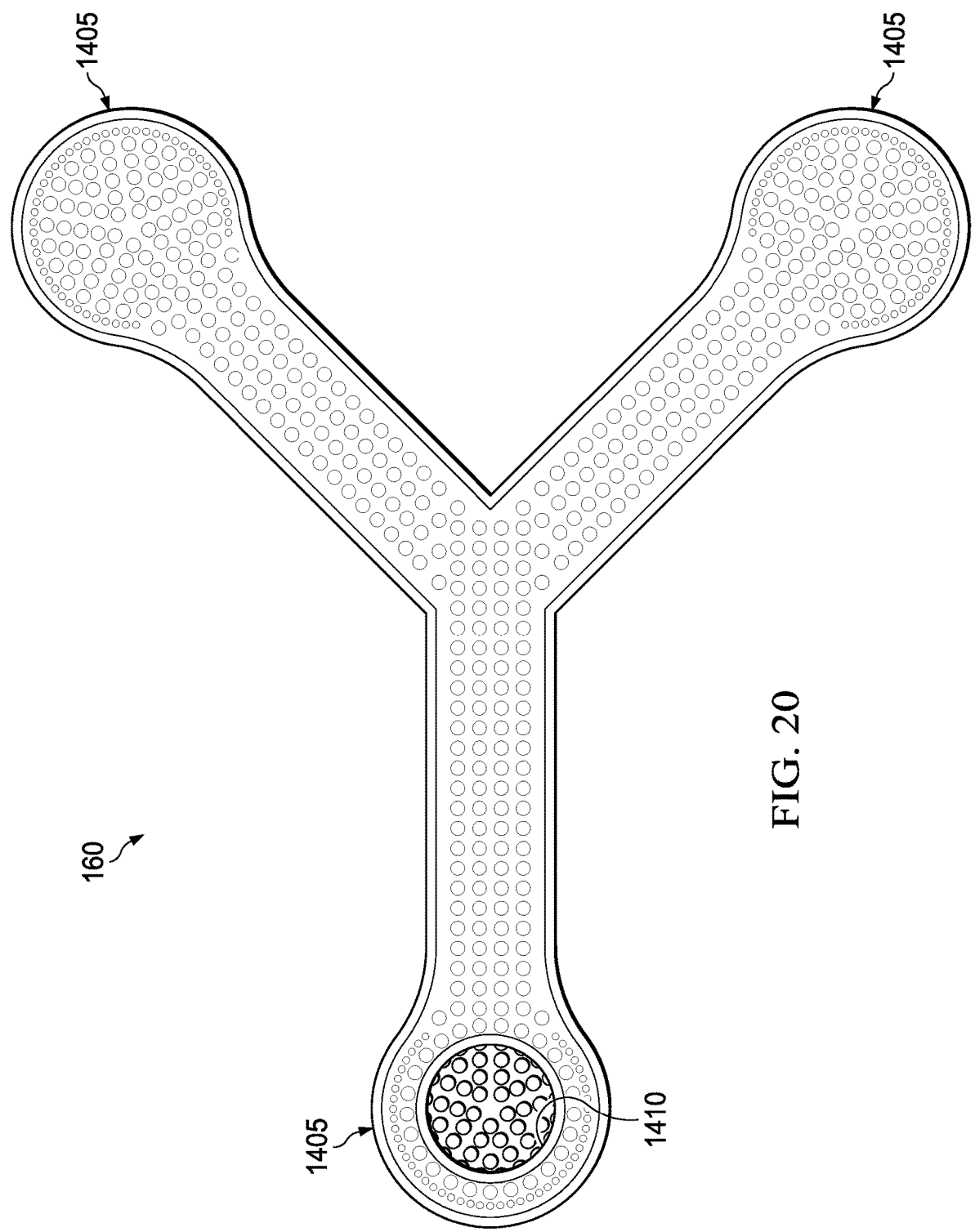
FIG. 20 is a plan view of another example of a bridge with a plurality of distal ends that may be associated with some example embodiments of the therapy system of FIG. 1.

FIG. 20 is a plan view of another example of a bridge 160 with a plurality of distal ends 1405 that may be associated with some example embodiments of the therapy system of FIG. 1, illustrating additional details that may be associated with some embodiments. The bridge 160 of FIG. 20 may be similar to that of FIG. 19, but the port 1410 may be located in one of the distal ends 1405 (e.g. instead of being located in the central portion). In the example of FIG. 20, one distal end 1405 may comprise the port 1410 (e.g. on the first surface), and the remaining distal ends 1405 may each comprise an aperture (not shown, but located on the second surface).

Figure 21:
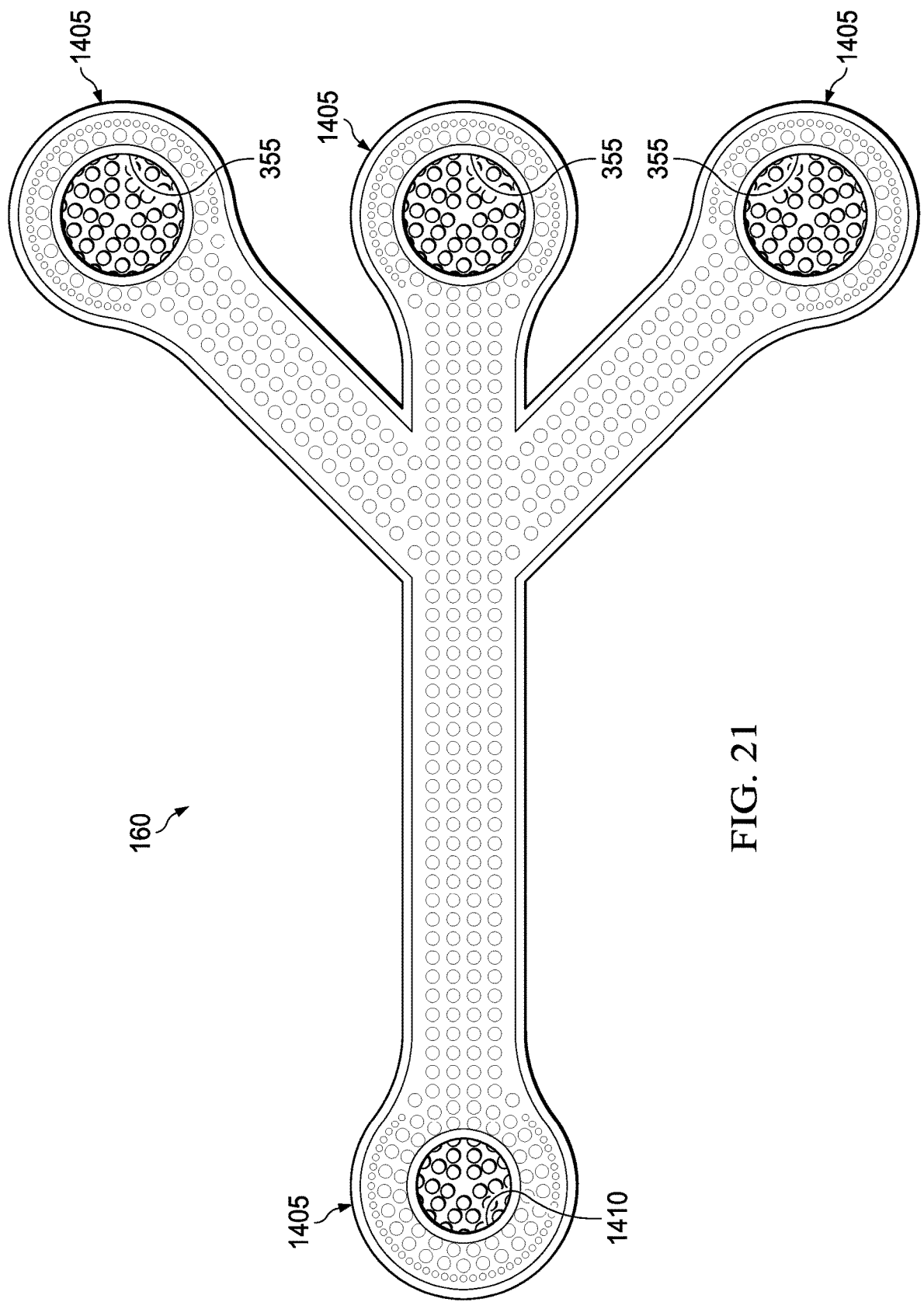
FIG. 21 is a plan view of another example of a bridge with a plurality of distal ends that may be associated with some example embodiments of the therapy system of FIG. 1.

FIG. 21 is a bottom plan view of another example of a bridge 160 with a plurality of distal ends 1405 that may be associated with some example embodiments of the therapy system of FIG. 1, illustrating additional details that may be associated with some embodiments. The bridge 160 of FIG. 21 may be similar to that of FIG. 18, except that the port 1410 may be located in one of the distal ends 1405 and on the same surface as the apertures 355 (e.g. the second surface). In FIG. 21, all of the other distal ends 1405 (without the port 1410) may each comprise an aperture 355. So as configured in FIG. 21, the bridge 160 may have three distal ends 1405 with apertures 355 configured to interact with (e.g. be in fluid communication with) tissue sites, and one distal end 1405 configured to interact with (e.g. be in fluid communication with) the negative-pressure source. In some embodiments, the distal ends 1405 may not be directly in fluid communication with the negative-pressure source and/or the tissue sites, but may serve as a branching connector (e.g. an intermediary fluid connector).

Figure 22:
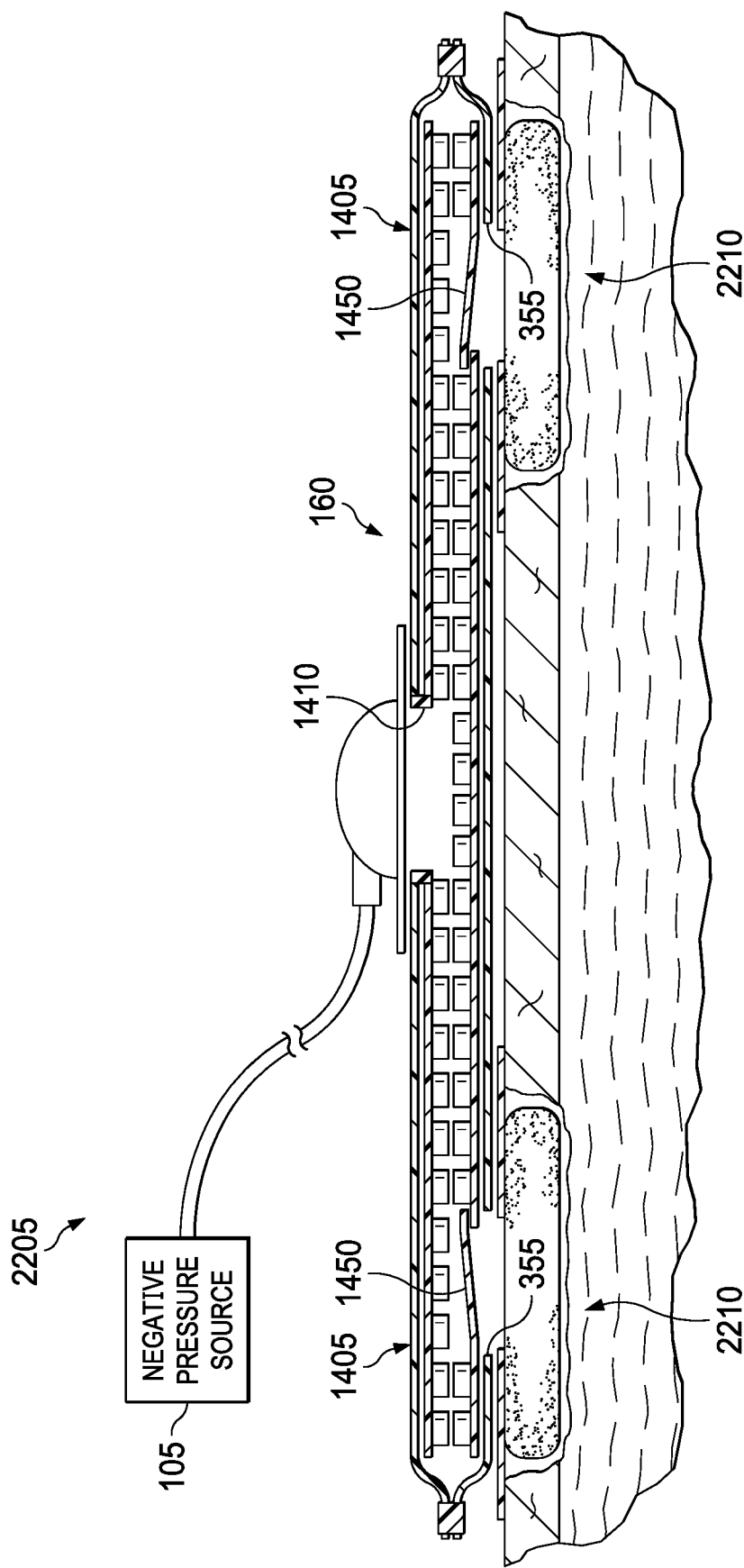
FIG. 22 is a schematic view of a system using the bridge of FIG. 14A to provide negative-pressure therapy to a plurality of tissue sites simultaneously with only one negative-pressure source.

FIG. 22 is a schematic view of a system 2205 for simultaneously treating a plurality of tissue sites 2210 with a single negative-pressure source 105. The system 2205 may comprise a fluid bridge 160 and a negative-pressure source 105. The fluid bridge 160 may comprise a plurality of distal ends 1405, with at least two of the distal ends 1405 each having an aperture 355 for interaction with one of the plurality of tissue sites 2210. For example, the fluid bridge 160 may be similar to that of FIG. 14A (although other bridge embodiments may be used in the system). The negative-pressure source 105 may be in fluid communication with the fluid bridge 160 at the port 1410. The bridge 160 may comprise one or more one-way valves 1450, configured to open when negative pressure is applied to the bridge 160 and to close in the absence of negative pressure. In use, the fluid bridge 160 may be applied to the patient so that the plurality of distal end apertures 355 fluidly communicate with the plurality of tissue sites 2210. The supports within the bridge 160 may allow the system 2205 to operate to effectively provide negative pressure even when at least a portion of the fluid bridge 160 is under compression. For example, the system 2205 may be used when at least a portion of the fluid bridge 160 is located under a patient's body (e.g. has at least a portion of the patient's body weight compressing it). In some embodiments, at least a portion of the fluid bridge 160 may be folded. For example, the primary fluid pathway and/or one or more branch fluid pathways may be folded to adjust the length of the bridge 160 and/or the position (e.g. lateral position) of the distal ends 1405 so that the fluid bridge 160 may effectively be adapted to interact with a plurality of tissue sites 2210 at various locations on the patient's body. The adaptability of the system 2205 (e.g. via folding) ensures that it can be used in a variety of wound scenarios having multiple tissue sites 2210 located at different positions on the patient's body. In some embodiments, the fold may be an accordion fold. In some embodiments, the fluid bridge 160 may be configured to maintain effective negative-pressure therapy (e.g. provide therapeutic levels of negative pressure at the distal ends 1405) when the fluid bridge 160 is folded and/or when at least a portion of the fluid bridge 160 is under compression. Typically, a single negative-pressure source 105 may be used with the bridge 160 to provide negative-pressure therapy to a plurality of tissue sites 2210.

Some embodiments may relate to methods of simultaneously applying negative pressure to a plurality of tissue sites using only a single negative-pressure source. For example, some method embodiments may use a bridge similar to one of the bridges of FIGS. 14A-21. Some method embodiments may comprise the steps of: providing a fluid bridge; applying two or more distal ends of the fluid bridge to a plurality of tissue sites; and applying negative pressure to a port of the fluid bridge, wherein a single negative-pressure source simultaneously applies negative-pressure to the plurality of tissue sites. In some embodiments, the plurality of tissue sites may be discrete, for example located separate and apart. Some method embodiments may further comprise the step of adjusting the fluid bridge to position the distal ends with respect to the plurality of tissue sites. The fluid bridge in some embodiments may comprise a primary pathway and one or more branch pathways. In some embodiments, adjusting the fluid bridge may comprise adjusting the length of one or more branch pathways. By way of example, adjusting the length of the one or more branch bridges may comprise folding the one or more branch bridges. The fold may be an accordion fold in some embodiments. In some embodiments, adjusting the fluid bridge may comprise adjusting the lateral position of one or more of the distal ends by folding the one or more branch pathways at an angle. In some method embodiments, the step of adjusting the fluid bridge may comprise adjusting the length of the primary pathway. By way of example, adjusting the length of the primary pathway may comprise folding the primary pathway. The fold may be an accordion fold in some embodiments. In some embodiments, adjusting the fluid bridge may comprise adjusting the lateral position of one or more of the distal ends by folding the primary pathway at an angle. Typically, the fluid pathway may remain open when folded. For example, the fluid bridge may be configured so that folding the fluid bridge does not significantly impact fluid flow therethrough and/or the fluid pathway remains open despite folding. Some embodiments may further comprise retaining the fold, for example using tape.

In some method embodiments, applying the distal ends to the plurality of tissue sites may comprise adhering the distal ends to the tissue sites and/or the tissue interfaces at the tissue sites. Some method embodiments may further comprise opening one or more one-way valves in the fluid bridge by application of negative pressure at the port. Some embodiments may further comprise preventing re-flux contamination to the tissue sites by closing the one or more one-way valves upon removal of negative pressure. In some embodiments, at least one of the tissue sites may be under compression. For example, some method embodiments may comprise positioning at least a portion of the fluid bridge underneath the patient. Given the configuration of the fluid bridge, the fluid bridge may maintain an open pathway sufficient to provide therapeutic negative pressure to the tissue sites, even when under compression and/or folded.

Some method embodiments relate to forming a fluid bridge for simultaneous application of negative pressure to a plurality of tissue sites using a single negative-pressure source. For example, method embodiments may comprise the steps of: providing a support layer (or manifold); encasing the support layer within an envelope, wherein the support layer supports the envelope to form an enclosed fluid pathway having a plurality of distal ends in fluid communication with a central portion; forming a port in a first surface of the envelope in proximity to the central portion; and forming a plurality of apertures in a second surface of the envelope in proximity to the distal ends. For example, each distal end may comprise one of the apertures. In some embodiments, the support layer may be configured to maintain an open pathway when under external compression and/or when under internal negative pressure and/or when folded. For example, the support layer may be a thermoformed support structure or a foam delivery manifold. The port may be configured to receive negative pressure, for example from a single negative-pressure source and introduce it into the fluid pathway of the bridge. The plurality of apertures may each be configured to fluidly interact with one of the plurality of tissue sites. For example, the apertures may allow fluid from the tissue sites to enter the fluid pathway when under negative pressure.

In some embodiments, the enclosed fluid pathway may comprise a primary pathway and one or more branch pathways. By way of example, providing a support layer may comprise forming the support layer to have a primary portion (e.g. relating to the primary fluid pathway) and one or more branch portions (e.g. relating to the branch fluid pathways). In some embodiments, providing the support layer may comprise the steps of: providing a first spacer layer with a first plurality of supports and a second spacer layer with a second plurality of supports; forming an opening in the first spacer layer; and forming a plurality of openings in the second spacer layer. In some embodiments, forming an opening in the first spacer layer may form the port recessed space, which may fluidly interact with and/or align with the port. In some embodiments, forming a plurality of openings in the second support layer may form the recessed spaces, which may be located in the distal ends to fluidly interact and/or align with the apertures. In some embodiments, providing the support layer may further comprise stacking the first spacer layer and the second spacer layer. For example, the first spacer layer and the second spacer layer may be stacked so that the first plurality of supports and the second plurality of supports are aligned and/or in stacked relationship.

In some method embodiments, the opening in the first spacer layer may be aligned with the port, and the plurality of openings in the second spacer layer may each be aligned with one of the plurality of apertures. In some embodiments, providing a first spacer layer and a second spacer layer may comprise thermoforming the first spacer layer and the second spacer layer. In some embodiments, providing a second spacer layer may comprise forming a one-way valve for each opening in the second spacer layer. For example, each one-way valve may be integral to the second spacer layer and may be configured to allow fluid flow into the fluid pathway (e.g. when there is negative pressure in the fluid pathway) but to prevent or restrict fluid flow out of the fluid pathway through the openings in the second spacer layer (e.g. when there is no substantial pressure differential between the fluid pathway and the tissue site). In some embodiments, forming a one-way valve in the second spacer layer may comprise stretching a portion of the second spacer layer film and perforating the second spacer layer film. For example, stretching the film may deform its thickness to about 60% of its original thickness (by application of a load), and perforation may occur after stretching. Stretching the film may make it more flexible, allowing the perforated area of the second spacer layer film to act as a valve (e.g. with respect to the opening formed by perforating the second spacer layer). In some embodiments, the deformation of the film material may be about 1-2 millimeters in height (e.g. during formation of the valve), and the valve may be shaped to suit the perforation (e.g. round, if the opening formed by the perforation is round).

The systems, apparatuses, and methods described herein may provide significant advantages. For example, some embodiments may allow a single negative-pressure source to provide negative-pressure therapy to multiple wound sites. Some embodiments may have a low-profile and/or be conformable, for improved comfort if positioned under a patient for example. Some embodiments may be configured to prevent occlusion, maintaining an open pathway for negative-pressure treatment so that the negative pressure may be provided even when the device is under compressive load (for example, if the patient is lying atop the device). Some embodiments allow for simplified adjustment of the bridge to adapt to the locations of multiple wounds (e.g. by folding). Some embodiments may improve access to certain wound sites. The configuration of some embodiments may reduce contamination, for example by preventing exudate from one wound from flowing into another wound.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 110, the container 115, or both may be eliminated or separated from other components for manufacture or sale. In other example configurations, the bridge 160 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. An apparatus for delivering negative pressure to a plurality of tissue sites, comprising:
    an envelope comprising a first surface and a second surface, the envelope being liquid impermeable; and
    a support layer disposed between the first surface and the second surface to form a fluid pathway, the support layer being liquid impermeable and the fluid pathway comprising:
        a central portion having a port in the envelope; and
        a plurality of distal ends in fluid communication with the central portion, each of the plurality of distal ends having an aperture in the envelope.

2. The apparatus of claim 1, wherein:
    the port is located on the first surface; and
    the aperture of each of the plurality of distal ends is located on the second surface.

3. The apparatus of claim 2, further comprising at least one one-way valve located between the port and the aperture of one of the plurality of distal ends and configured to allow fluid flow from the aperture toward the port.

4. The apparatus of claim 2, wherein each of the plurality of distal ends comprises a one-way valve in proximity to the aperture and configured to allow fluid flow from the aperture towards the port.

5. The apparatus of claim 4, wherein the support layer comprises a thermoformed support structure.

6. The apparatus of claim 4, wherein the support layer comprises a plurality of supports configured to support the envelope.

7. The apparatus of claim 6, wherein the plurality of supports are substantially co-extensive with the fluid pathway.

8. The apparatus of claim 6, wherein each of the plurality of supports comprises a hollow standoff which is sealed to maintain an internal pressure.

9. The apparatus of claim 6, wherein:
    the envelope further comprises a first layer and a second layer;
    the first layer comprises the first surface of the envelope, and the second layer comprises the second surface of the envelope;
    the first layer and the second layer are coupled to enclose the fluid pathway between the first layer and the second layer; and
    the plurality of supports are located between the first layer and the second layer.

10. The apparatus of claim 6, wherein the support layer comprises a spacer layer, and the plurality of supports extend from an inner surface of the spacer layer.

11. The apparatus of claim 6, wherein:
    the plurality of supports comprises a first plurality of supports and a second plurality of supports; and
    the first plurality of supports are in stacked relationship with the second plurality of supports.

12. The apparatus of claim 6, wherein:
    the support layer further comprises a first spacer layer and a second spacer layer; and
    the plurality of supports comprises a first plurality of supports extending inward from the first spacer layer and a second plurality of supports extending inward from the second spacer layer.

13. The apparatus of claim 12, wherein the fluid pathway further comprises a recessed space in each of the plurality of distal ends in fluid communication with the aperture, and each recessed space is formed by an opening in the second spacer layer.

14. The apparatus of claim 13, wherein the fluid pathway further comprises a port recessed space in fluid communication with the port, and the port recessed space is formed by an opening in the first spacer layer.

15. The apparatus of claim 14, wherein the one-way valve of each of the plurality of distal ends is integral to the second spacer layer.

16. The apparatus of claim 4, wherein the support layer comprises a foam delivery manifold.

17. The apparatus of claim 1, wherein the enclosed fluid pathway comprises a primary fluid pathway having two distal ends of the plurality of distal ends.

18. The apparatus of claim 17, wherein the enclosed fluid pathway further comprises one or more branch fluid pathways, each having one distal end of the plurality of distal ends and a proximal end in fluid communication with the primary fluid pathway.

19. The apparatus of claim 4, further comprising a plurality of release liners, wherein one of the plurality of release liners removably covers each aperture.

20. The apparatus of claim 19, wherein each of the plurality of release liners removably seals one of the apertures.

21. The apparatus of claim 20, wherein each of the plurality of distal ends further comprises adhesive located in proximity to the aperture.

22. The apparatus of claim 4, further comprising a regulator positioned between each of the plurality of distal ends and the central portion, wherein the regulator is configured to step-down pressure.

23. The apparatus of claim 4, wherein the envelope comprises a perforation forming a calibrated flow of less than about 5 cc/min located in proximity to each of the plurality of distal ends.

24. The apparatus of claim 23, wherein the envelope further comprises a bacterial filter over each calibrated flow.

* * * * *